US011338041B2

(12) United States Patent
Hanson et al.

(10) Patent No.: US 11,338,041 B2
(45) Date of Patent: May 24, 2022

(54) EXON SKIPPING OLIGOMER CONJUGATES FOR MUSCULAR DYSTROPHY

(71) Applicant: Sarepta Therapeutics, Inc., Cambridge, MA (US)

(72) Inventors: Gunnar J. Hanson, Cambridge, MA (US); Marco A. Passini, Cambridge, MA (US); Frederick Joseph Schnell, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/938,278

(22) Filed: Jul. 24, 2020

(65) Prior Publication Data

US 2021/0138079 A1 May 13, 2021

Related U.S. Application Data

(62) Division of application No. 15/993,287, filed on May 30, 2018, now Pat. No. 10,765,760.

(60) Provisional application No. 62/677,484, filed on May 29, 2018.

(51) Int. Cl.
| | | |
|---|---|---|
| C07H 21/04 | (2006.01) |
| A61K 47/68 | (2017.01) |
| A61K 9/00 | (2006.01) |
| C07K 14/47 | (2006.01) |
| C12N 15/113 | (2010.01) |
| C12N 15/62 | (2006.01) |

(52) U.S. Cl.
CPC ........ *A61K 47/6807* (2017.08); *A61K 9/0019* (2013.01); *C07K 14/4707* (2013.01); *C12N 15/113* (2013.01); *C12N 15/62* (2013.01); *C12N 2310/11* (2013.01); *C12N 2310/3233* (2013.01)

(58) Field of Classification Search
None
See application file for complete search history.

(56) References Cited

U.S. PATENT DOCUMENTS

| | | |
|---|---|---|
| 3,420,788 A | 1/1969 | Solms |
| 3,426,011 A | 2/1969 | Parmerter et al. |
| 3,453,257 A | 7/1969 | Permerter et al. |
| 3,453,259 A | 7/1969 | Parmerter et al. |
| 3,459,731 A | 8/1969 | Gramera et al. |
| 4,235,871 A | 11/1980 | Papahadjopoulos et al. |
| 4,737,323 A | 4/1988 | Martin et al. |
| 5,034,506 A | 7/1991 | Summerton et al. |
| 5,134,127 A | 7/1992 | Stella et al. |
| 5,142,047 A | 8/1992 | Summerton et al. |
| 5,166,315 A | 11/1992 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,539,082 A | 7/1996 | Nielsen et al. |
| 5,627,274 A | 5/1997 | Kole et al. |
| 5,665,593 A | 9/1997 | Kole et al. |
| 5,698,685 A | 12/1997 | Summerton et al. |
| 5,714,331 A | 2/1998 | Buchardt et al. |
| 5,719,262 A | 2/1998 | Buchardt et al. |
| 5,916,808 A | 6/1999 | Kole et al. |
| 5,976,879 A | 11/1999 | Kole et al. |
| 6,210,892 B1 | 4/2001 | Bennett et al. |
| 6,653,466 B2 | 11/2003 | Matsuo et al. |
| 6,653,467 B1 | 11/2003 | Matsuo et al. |
| 6,670,461 B1 | 12/2003 | Wengel et al. |
| 6,683,173 B2 | 1/2004 | Robert et al. |
| 6,692,911 B2 | 2/2004 | Pack et al. |
| 6,727,355 B2 | 4/2004 | Matsuo et al. |
| 6,794,499 B2 | 9/2004 | Wengel et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,070,807 B2 | 7/2006 | Mixson |
| 7,084,125 B2 | 8/2006 | Wengel |
| 7,125,994 B2 | 10/2006 | Kim et al. |
| 7,145,006 B2 | 12/2006 | Kim et al. |
| 7,163,695 B2 | 1/2007 | Mixson |
| 7,179,896 B2 | 2/2007 | Kim et al. |
| 7,211,668 B2 | 5/2007 | Kim et al. |
| 7,569,575 B2 | 8/2009 | Soerensen et al. |
| 7,572,582 B2 | 8/2009 | Wengel et al. |
| 8,076,476 B2 | 12/2011 | Reeves et al. |
| 8,084,601 B2 | 12/2011 | Popplewell et al. |
| 8,299,206 B2 | 10/2012 | Fox et al. |
| 9,161,948 B2 | 10/2015 | Hanson |

(Continued)

FOREIGN PATENT DOCUMENTS

| | | | |
|---|---|---|---|
| JP | 2000125448 A | 4/2000 |
| JP | 2000256547 A | 9/2000 |

(Continued)

OTHER PUBLICATIONS

Aartsma-Rus, A., et al., "Antisense-Induced Multiexon Skipping for Duchenne Muscular Dystrophy Makes More Sense," American Journal of Human Genetics 74(1):83-92, University of Chicago Press, United States (Jan. 2004).

Aartsma-Rus, A., et al., "Theoretic Applicability of Antisense-mediated Exon Skipping for Duchenne Muscular Dystrophy Mutations," Human Mutation 30(3):293-299, Wiley-Liss, United States (Mar. 2009).

Abes, R., et al., "Arginine rich Cell Penetrating Peptides: Design, Structure-activity, and Applications to Alter Pre mRNA Splicing by Steric block Oligonucleotides," Journal of Peptide Science 14(4):455-460 (Apr. 2008).

Akhtar, S. and Juliano, R.L., "Cellular Uptake and Intracellular Fate of Antisense Oligonucleotides," Trends in Cell Biology 2(5):139-144 (May 1992).

(Continued)

*Primary Examiner* — Kimberly Chong
(74) *Attorney, Agent, or Firm* — Sterne, Kessler, Goldstein & Fox P.L.L.C.

(57) ABSTRACT

Antisense oligomer conjugates complementary to a selected target site in the human dystrophin gene to induce exon 52 skipping are described.

22 Claims, 26 Drawing Sheets

Specification includes a Sequence Listing.

(56) References Cited

U.S. PATENT DOCUMENTS

| | | |
|---|---|---|
| 10,758,629 B2 | 9/2020 | Bestwick et al. |
| 11,000,600 B2 | 5/2021 | Passini et al. |
| 2008/0249052 A1 | 10/2008 | Duan et al. |
| 2012/0289457 A1 | 11/2012 | Hanson |
| 2013/0211062 A1 | 8/2013 | Watanabe et al. |
| 2014/0330006 A1 | 11/2014 | Hanson |
| 2017/0204413 A1 | 7/2017 | Popplewell et al. |
| 2019/0365918 A1 | 12/2019 | Bestwick et al. |
| 2021/0138078 A1 | 5/2021 | Bestwick et al. |
| 2021/0338830 A1 | 11/2021 | Passini et al. |

FOREIGN PATENT DOCUMENTS

| | | |
|---|---|---|
| WO | WO-9402595 A1 | 2/1994 |
| WO | WO-9610390 A1 | 4/1996 |
| WO | WO-9610391 A1 | 4/1996 |
| WO | WO-9610392 A1 | 4/1996 |
| WO | WO-9614057 A1 | 5/1996 |
| WO | WO-0224906 A1 | 3/2002 |
| WO | WO-2004043977 A2 | 5/2004 |
| WO | WO-2004048570 A1 | 6/2004 |
| WO | WO-2004083432 A1 | 9/2004 |
| WO | WO-2004083446 A2 | 9/2004 |
| WO | WO-2006000057 A1 | 1/2006 |
| WO | WO-2006112705 A2 | 10/2006 |
| WO | WO-2007058894 A2 | 5/2007 |
| WO | WO-2007133105 A1 | 11/2007 |
| WO | WO-2009008725 A2 | 1/2009 |
| WO | WO-2009054725 A2 | 4/2009 |
| WO | WO-2009064471 A1 | 5/2009 |
| WO | WO-2009127230 A1 | 10/2009 |
| WO | WO-2009139630 A2 | 11/2009 |
| WO | WO-2010048586 A1 | 4/2010 |
| WO | WO-2010050801 A1 | 5/2010 |
| WO | WO-2010050802 A2 | 5/2010 |
| WO | WO-2010064146 A2 | 6/2010 |
| WO | WO-2010115993 A1 | 10/2010 |
| WO | WO-2010123369 A1 | 10/2010 |
| WO | WO-2011005761 A1 | 1/2011 |
| WO | WO-2011034072 A1 | 3/2011 |
| WO | WO-2011057350 A1 | 5/2011 |
| WO | WO-2012029986 A1 | 3/2012 |
| WO | WO-2012039448 A1 | 3/2012 |
| WO | WO-2012109296 A1 | 8/2012 |
| WO | WO-2013053928 A1 | 4/2013 |
| WO | WO-2013100190 A1 | 7/2013 |
| WO | WO-2013112053 A1 | 8/2013 |
| WO | WO-2013127858 A1 | 9/2013 |
| WO | WO-2014007620 A2 | 1/2014 |
| WO | WO-2014010250 A1 | 1/2014 |
| WO | WO-2014012081 A2 | 1/2014 |
| WO | WO-2014100714 A1 | 6/2014 |
| WO | WO-2014153220 A2 | 9/2014 |
| WO | WO-2014153240 A2 | 9/2014 |
| WO | WO-2015107425 A2 | 7/2015 |
| WO | WO-2015108046 A1 | 7/2015 |
| WO | WO-2015108047 A1 | 7/2015 |
| WO | WO-2015108048 A1 | 7/2015 |
| WO | WO-2015137409 A1 | 9/2015 |
| WO | WO-2015194520 A1 | 12/2015 |
| WO | WO-2016070166 A2 | 5/2016 |
| WO | WO-2017015555 A1 | 1/2017 |
| WO | WO-2017015575 A1 | 1/2017 |
| WO | WO-2017049407 A1 | 3/2017 |
| WO | WO-2017062862 A2 | 4/2017 |
| WO | WO-2017192664 A1 | 11/2017 |
| WO | WO-2017192679 A1 | 11/2017 |

OTHER PUBLICATIONS

Akhtar, S., "Delivery Strategies for Antisense Oligonucleotide Therapeutics," CRC Press, 320 pages (Jun. 1995).

Alter, J., et al., "Systemic Delivery of Morpholino Oligonucleotide Restores Dystrophin Expression Bodywide and Improves Dystrophic Pathology," Nature Medicine 12(2):175-177, Nature Publishing Company, United States (Feb. 2006).

Anderson, W.F., "Human Gene Therapy," Science 256(5058):808-813, American Association for the Advancement of Science, United States (May 1992).

Arechavala-Gomeza, V., et al., "Comparative Analysis of Antisense Oligonucleotide Sequences for Targeted Skipping of Exon 51 During Dystrophin Pre-mRNA Splicing in Human Muscle," Human Gene Therapy 18(9):798-810, Liebert, United States (Sep. 2007).

Barton-Davis, E.R., et al., "Aminoglycoside Antibiotics Restore Dystrophin Function to Skeletal Muscles of Mdx Mice," Journal of Clinical Investigation, 104(4):375-381, American Society for Clinical Investigation, United States (Aug. 1999).

Benner, S.A. and Sismour, A.M., "Synthetic Biology," Nature Reviews. Genetics 6(7):553-543, Nature Pub. Group, England (Jul. 2005).

Berge, S.M., et al., "Pharmaceutical Salts," Journal of Pharmaceutical Sciences 66(1): 1-19, Wiley, United States (Jan. 1977).

Bestas, B., et al., "Splice-correcting Oligonucleotides Restore BTK Function in X-linked Agammaglobulinemia Model," The Journal of Clinical Investigation 124(9):4067-4081, American Society for Clinical Investigation, United States (Sep. 2014).

Brigham, K.L., et al., "In Vivo Transfection of Murine Lungs With a Functioning Prokaryotic Gene Using a Liposome Vehicle," The American Journal of the Medical Sciences 298(4):278-281, Elsevier, United States (Oct. 1989).

Brown, S.C., et al., "Dystrophic Phenotype Induced in Vitro by Antibody Blockade of Muscle Alpha-dystroglycan-laminin Interaction," Journal of Cell Science 112(Pt 2):209-216, Company of Biologists, England (Jan. 1999).

Chiu, Y.L. and Rana, T.M., "SiRNA Function in RNAi: A Chemical Modification Analysis," RNA 9(9):1034-1048, Cold Spring Harbor Laboratory Press, United States (Sep. 2003).

Cirak, S., et al., "Exon Skipping and Dystrophin Restoration in Patients With Duchenne Muscular Dystrophy After Systemic Phosphorodiamidate Morpholino Oligomer Treatment: An Open-label, Phase 2, Dose-escalation Study," Lancet 378(9791):595-605, Elsevier, England (Aug. 2011).

Collins, C.A. and Morgan, J.E., "Duchenne's Muscular Dystrophy: Animal Models Used to Investigate Pathogenesis and Develop Therapeutic Strategies," International Journal of Experimental Pathology 84(4):165-172, Wiley, England (Aug. 2003).

U.S. Appl. No. 61/096,073, filed Sep. 11, 2008.

U.S. Appl. No. 61/164,978, filed Mar. 31, 2009.

Dellorusso, C., et al., "Functional Correction of Adult Mdx Mouse Muscle Using Gutted Adenoviral Vectors Expressing Full-length Dystrophin," Proceedings of the National Academy of Sciences of the United States of America 99(20):12979-12984, National Academy of Sciences, United States (Oct. 2002).

Dordunoo, S.K., et al., "Preformulation Studies on Solid Dispersions Containing Triamterene or Temazepam in Polyethylene Glycols or Gelucire 44/14 for Liquid Filling of Hard Gelatin Capsules," Drug Development and Industrial Pharmacy 17(12):1685-1713 (Oct. 2008).

Dunckley, M.G., et al., "Modification of Splicing in the Dystrophin Gene in Cultured Mdx Muscle Cells by Antisense Oligoribonucleotides," Human Molecular Genetics 7(7):1083-1090, IRL Press, England (Jul. 1998).

Dunckley, M.G., et al., "Modulation of Splicing in the DMD Gene by Antisense Oligoribonucleotides," Nucleosides & Nucleotides 16(7-9):1665-1668 (Jul.-Sep. 1997).

Egholm, M., et al., "PNA Hybridizes to Complementary Oligonucleotides Obeying the Watson-crick Hydrogen-bonding Rules," Nature 365(6446):566-568, Nature Publishing Group, England (Oct. 1993).

Emerich, D.F., et al., "Biocompatibility of Poly (DL-lactide-co-glycolide) Microspheres Implanted Into the Brain," Cell Transplantation 8(1):47-58, SAGE Publishing, United States (Jan.-Feb. 1999).

Errington, S.J., et al., "Target Selection for Antisense Oligonucleotide Induced Exon Skipping in the Dystrophin Gene," The Journal of Gene Medicine 5(6):518-527, John Wiley & Sons, England (Jun. 2003).

(56) References Cited

OTHER PUBLICATIONS

Fletcher, S., et al., "Dystrophin Isoform Induction in Vivo by Antisense-mediated Alternative Splicing," Molecular Therapy 18(6):1218-1223, Cell Press, United States (Jun. 2010).

Friedmann, T., "Progress Toward Human Gene Therapy," Science 244(4910):1275-1280, American Association for the Advancement of Science, United States (Jun. 1989).

Goemans, N.M., et al., "Systemic Administration of PRO051 in Duchenne's Muscular Dystrophy," The New England Journal of Medicine 364(16):1513-1522, Massachusetts Medical Society, United States (Apr. 2011).

Goyenvalle, A., et al., "Rescue of Dystrophic Muscle Through U7 Snrna-mediated Exon Skipping," Science 306(5702):1796-1799, American Association for the Advancement of Science, United States (Dec. 2004).

Singh, S.K., et al., "LNA (locked nucleic acids): Synthesis and High-affinity Nucleic Acid Recognition," Chemical Communications 29(4):455-456 (1998).

Gregorevic, P., et al., "rAAV6-microdystrophin Preserves Muscle Function and Extends Lifespan in Severely Dystrophic Mice," Nature Medicine 12(7):787-789, Nature Publishing Company, United States (Jul. 2006).

Gurvich, O.L., et al., "DMD Exon 1 Truncating Point Mutations: Amelioration of Phenotype by Alternative Translation Initiation in Exon 6," Human Mutation 30(4):633-640, Wiley-Liss, United States (Apr. 2009).

Han, G., et al., "Hexose Enhances Oligonucleotide Delivery and Exon Skipping in Dystrophin-deficient Mdx Mice," Nature Communications 7:10981, Nature Pub. Group, England (Mar. 2016).

Hazinski, T.A., et al., "Localization and Induced Expression of Fusion Genes in the Rat Lung," American Journal of Respiratory Cell and Molecular Biology 4(3):206-209, American Thoracic Society, United States (Mar. 1991).

Ezzat, K., et al., "Self-Assembly into Nanoparticles Is Essential for Receptor Mediated Uptake of Therapeutic Antisense Oligonucleotides," Nano Letters 15:4364-4373, ACS Publications, United States (2015).

Henry, A.A. and Romesberg, F.E., "Beyond A, C, G and T: Augmenting Nature's Alphabet," Current Opinion in Chemical Biology 7(6):723-733, Elsevier, England (Dec. 2003).

Hirao, I., "Unnatural Base Pair Systems for DNA/RNA-based Biotechnology," Current Opinion in Chemical Biology 10(6):622-627, Elsevier, England (Dec. 2006).

Ishiwata, H., et al., "Physical-chemistry Characteristics and Biodistribution of Poly(Ethylene Glycol)-coated Liposomes Using Poly(Oxyethylene) Cholesteryl Ether," Chemical & Pharmaceutical Bulletin 43(6):1005-1011, Pharmaceutical Society of Japan, Japan (Jun. 1995).

Iyer, R.P., et al., "The Automated Synthesis of Sulfur-Containing Oligodeoxyribonucleotides Using 3H-1,2-Benzodithiol-3-one 1,1-Dioxide as a Sulfur-Transfer Reagent," The Journal of Organic Chemistry 55(15):4693-4699 (1990).

Jearawiriyapaisarn, N., et al., "Long-term Improvement in Mdx Cardiomyopathy After Therapy With Peptide-conjugated Morpholino Oligomers," Cardiovascular Research 85(3):444-453, Oxford Journals, England (Feb. 2010).

Jearawiriyapaisarn, N., et al., "Sustained Dystrophin Expression Induced by Peptide-conjugated Morpholino Oligomers in the Muscles of Mdx Mice," Molecular Therapy 16(9):1624-1629, Cell Press, United States (Sep. 2008).

Kawano, R., et al., "Transduction of Full-length Dystrophin to Multiple Skeletal Muscles Improves Motor Performance and Life Span in Utrophin/dystrophin Double Knockout Mice," Molecular Therapy 16(5):825-831, Cell Press, United States (May 2008).

Kinali, M., et al., "Local Restoration of Dystrophin Expression With the Morpholino Oligomer AVI-4658 in Duchenne Muscular Dystrophy: a Single-blind, Placebo-controlled, Dose-escalation, Proof-of-concept Study," The Lancet Neurology 8(10):918-928, Lancet Pub. Group, England (Oct. 2009).

Kool, E.T., "Replacing the Nucleobases in DNA with Designer Molecules," Accounts of Chemical Research 35(11):936-943, American Chemical Society, United States (Nov. 2002).

Koshkin, A.A., et al., "LNA (Locked Nucleic Acids): Synthesis of the Adenine, Cytosine, Guanine, 5-methylcytosine, Thymine and Uracil Bicyclonucleoside Monomers, Oligomerisation and Unprecedented Nucleic Acid Recognition," Tetrahedron 54:3607-3630, Pergamon Press, England(1998). (Exhibit No. 2007 filed in interferences 106008, 106013, 106007 on Nov. 18, 2014).

Krueger, A.T., et al., "Synthesis and Properties of Size-expanded DNAs: Toward Designed, Functional Genetic Systems," Accounts of Chemical Research 40(2):141-150, American Chemical Society, United States (Feb. 2007).

Lasic, D.D. and Needham, D., "The "Stealth" Liposome: A Prototypical Biomaterial," Chemical Reviews 95(8):2601-2628 (1995).

Lasic, D.D. and Papahadjopoulos, D., "Liposomes Revisited," Science 267(5202):1275-1276, American Association for the Advancement of Science, United States (Mar. 1995).

Jarver, P., et al., "A Chemical View of Oligonucleotides for Exon Skipping and Related Drug Applications," Nucleic Acid Therapeutics 24:37-47, Mary Ann Liebert, United States (2014).

Lebleu, B., et al., "Cell Penetrating Peptide Conjugates of Steric Block Oligonucleotides," Advanced Drug Delivery Reviews 60(4-5):517-529, Elsevier Science Publishers, Netherlands (Mar. 2008).

Limbach, P.A., et al., "Summary: the Modified Nucleosides of RNA," Nucleic Acids Research 22(12):2183-2196, Oxford University Press, England (Jun. 1994).

Liu, Y., et al., "Cationic Liposome-mediated Intravenous Gene Delivery," The Journal of Biological Chemistry 270(42):24864-24870, American Society for Biochemistry and Molecular Biology, United States (Oct. 1995).

Lu, Q.L., et al., "Functional Amounts of Dystrophin Produced by Skipping the Mutated Exon in the mdx Dystrophic Mouse," Nature Medicine 9(8):1009-1014, Nature Publishing Company, United States (Aug. 2003).

Mann, C.J., et al., "Improved Antisense Oligonucleotide Induced Exon Skipping in the mdx Mouse Model of Muscular Dystrophy," The Journal of Gene Medicine 4(6):644-654, John Wiley & Sons, England (Nov.-Dec. 2002).

Marshall, N.B., et al., "Arginine-rich Cell-penetrating Peptides Facilitate Delivery of Antisense Oligomers Into Murine Leukocytes and Alter Pre-mrna Splicing," Journal of Immunological Methods 325(1-2):114-126, Elsevier, Netherlands (Aug. 2007).

Martin, P., "New Access to 2'-O-alkylated Ribonucleosides and Properties of 2'-O-alkylated Oligoribonucleotides," Helvetica Chimica Acta 78(2):486-504 (Jan. 1995).

Matsuo, M., et al., "Exon Skipping During Splicing of Dystrophin mRNA Precursor Due to an Intraexon Deletion in the Dystrophin Gene of Duchenne Muscular Dystrophy Kobe," The Journal of Clinical Investigation 87(6):2127-2131, American Society for Clinical Investigation, United States (Jun. 1991).

Mcclorey, G., et al., "Antisense Oligonucleotide-induced Exon Skipping Restores Dystrophin Expression in Vitro in a Canine Model of DMD," Gene Therapy 13(19):1373-1381, Nature Publishing Group, England (Oct. 2006).

Mcdonald, C.M., et al., "The 6-minute Walk Test in Duchenne/becker Muscular Dystrophy: Longitudinal Observations," Muscle & Nerve 42(6):966-974, John Wiley & Sons, United States (Dec. 2010).

Monaco, A.P., et al., "An Explanation for the Phenotypic Differences Between Patients Bearing Partial Deletions of the DMD Locus," Genomics 2(1):90-95, Academic Press, United States (Jan. 1988).

Moulton, H.M., et al., "Cell-penetrating Peptide-morpholino Conjugates Alter Pre-mRNA Splicing of DMD (Duchenne Muscular Dystrophy) and Inhibit Murine Coronavirus Replication in Vivo," Biochemical Society Transactions 35(Pt 4):826-828, Portland Press, England (Aug. 2007).

Heemskerk, H., et al., "In vivo comparison of 2'-O-methyl phosphorothioate and morpholino antisense oligonucleotides for Duchenne muscular dystrophy exon skipping," The Journal of Gene Medicine 11:257-266, Wiley, United States (2009).

(56) References Cited

OTHER PUBLICATIONS

Nabel, E.G., et al., "Site-specific Gene Expression in Vivo by Direct Gene Transfer Into the Arterial Wall," Science 249(4974):1285-1288, American Association for the Advancement of Science, United States (Sep. 1990).
New RRC, "Liposomes: A practical approach," IRL Press, Oxford University Press, New York, pp. 33-104 (1990).
Nielsen, P.E., et al., "Sequence-Selective Recognition of DNA by Strand Displacement with a Thymine-Substituted Polyamide," Science 254(5037):1497-1500, American Association for the Advancement of Science, United States (Dec. 1991).
Obika, S., et al., "Stability and Structural Features of the Duplexes Containing Nucleoside Analogues With a Fixed N-type Conformation, 2'-O,4'- C-methyleneribonucleosides ," Tetrahedron Letters 39(1998):5401-5404 (Jul. 1998).
Obika, S., et al., "Synthesis and Properties of 3'-amino-2',4'-BNA, a Bridged Nucleic Acid with a N3'→P5' Phosphoramidate Linkage," Bioorganic Medicinal Chemistry 16(20):9230-9237, Elsevier Science, England (Oct. 2008).
Obika, S., et al., "Synthesis of 2'-O,4'-C-methyleneuridine and -cytidine. Novel Bicyclic Nucleosides having a Fixed C3, -endo Sugar Puckering," Tetrahedron Letters 38(50):8735-8738 (Dec. 1997).
Oku, N., et al., "Real-time Analysis of Liposomal Trafficking in Tumor-bearing Mice by Use of Positron Emission Tomography," Biochimica et Biophysica acta 1238(1):86-90, Elsevier Pub. Co., Netherlands (Aug. 1995).
Peacock, H., et al., "Nucleobase and Ribose Modifications Control Immunostimulation by a MicroRNA-122-mimetic RNA," Journal of the American Chemical Society 133(24):9200-9203, American Chemical Society, United States (Jun. 2011).
*University of Western Australia v. Academisch Ziekenhuis Leiden*, Declaration of Matthew J.A. Wood, Patent Interference Nos. 106,007, 106,008 and 106,013, 184 pages, dated Nov. 18, 2014 (Exhibit No. 2081 filed in interferences 106008, 106013, 106007 on Nov. 18, 2014).
Pramono, Z.A., et al., "Induction of Exon Skipping of the Dystrophin Transcript in Lymphoblastoid Cells by Transfecting an Antisense Oligodeoxynucleotide Complementary to an Exon Recognition Sequence," Biochemical and Biophysical Research Communications 226(2):445-449, Elsevier, United States (Sep. 1996).
Reay, D.P., et al., "Full-length Dystrophin Gene Transfer to the Mdx Mouse in Utero," Gene Therapy 15(7):531-536, Nature Publishing Group, England (Apr. 2008).
*University of Western Australia v. Academisch Ziekenhuis Leiden*, Decision—Motions—37 CFR § 41.125{a) Substitute), filed in Patent Interference No. 106007, May 12, 2016, pp. 1-53 {Doc 476).
Rosenberg, S.A., "Immunotherapy and Gene Therapy of Cancer," Cancer Research 51(18 Suppl):5074S-5079S, American Association for Cancer Research, United States (Sep. 1991).
Rosenfeld, M.A., et al., "Adenovirus-mediated Transfer of a Recombinant alpha 1-antitrypsin Gene to the Lung Epithelium in Vivo," Science 252(5004):431-434, American Association for the Advancement of Science, United States (Apr. 1991).
Rosenfeld, M.A., et al., "In Vivo Transfer of the Human Cystic Fibrosis Transmembrane Conductance Regulator Gene to the Airway Epithelium," Cell 68(1):143-155, Cell Press, United States (Jan. 1992).
Schroeder, U., et al., "Diffusion Enhancement of Drugs by Loaded Nanoparticles in Vitro," Progress in Neuro-psychopharmacology & Biological Psychiatry 23(5):941-949, Pergamon Press, England (Jul. 1999).
Sharp, P.S., et al., "Physiological Characterization of Muscle Strength With Variable Levels of Dystrophin Restoration in Mdx Mice Following Local Antisense Therapy," Molecular Therapy 19(1):165-171, Cell Press, United States (Jan. 2011 ).
Sheen, P.C., et al., "Bioavailability of a Poorly Water-soluble Drug From Tablet and Solid Dispersion in Humans," Journal of Pharmaceutical Sciences 80(7):712-714, Elsevier, United States (Jul. 1991).
Sierakowska, H., et al., "Repair of Thalassemic Human Beta-globin mRNA in Mammalian Cells by Antisense Oligonucleotides," Proceedings of the National Academy of Sciences of the United States of America 93(23):12840-12844, National Academy of Sciences, United States (Nov. 1996).
Wu, B., et al., "Targeted skipping of human dystrophin exons in transgenic mouse model systemically for antisense drug development," *PloS one*, 65:e19906 (2011).
Summerton, J. and Weller, D., "Morpholino Antisense Oligomers: Design, Preparation, and Properties," Antisense & Nucleic Acid Drug Development 7(3):187-195, Mary Ann Liebert, Inc., United States (Jun. 1997).
Takeshima, Y., et al., "Modulation of in Vitro Splicing of the Upstream Intron by Modifying an Intra-exon Sequence Which Is Deleted From the Dystrophin Gene in Dystrophin Kobe," The Journal of Clinical Investigation 95(2):515-520, American Society for Clinical Investigation, United States (Feb. 1995).
van Deutekom et al., "Local Dystrophin Restoration with Antisense Oligonucleotide PRO051," N. Engl. J. Med., vol. 357, No. 26, pp. 2677-2686 (Dec. 2007), Exhibit No. 1213 filed in Interferences 106,007 and 106,008 on Feb. 17, 2015.
Van Deutekom, J.C., et al., "Antisense-induced Exon Skipping Restores Dystrophin Expression in DMD Patient Derived Muscle Cells," Human Molecular Genetics 10(15):1547-1554, IRL Press, England (Jul. 2001).
Van Putten, M, et al., "The Effects of Low Levels of Dystrophin on Mouse Muscle Function and Pathology," PLoS ONE,7(2):e31937, Public Library of Science, United States (Feb. 2012).
Van Uden, W., et al., "Cyclodextrins as a Useful Tool for Bioconversions in Plant Cell Biotechnology," Plant Cell, Tissue and Organ Culture 38(2-3):103-113, Kluwer Academic Publisher, Netherland (Sep. 1994).
Wang, C.Y. and Huang, L., "pH-sensitive Immunoliposomes Mediate Target-cell-specific Delivery and Controlled Expression of a Foreign Gene in Mouse," Proceedings of the National Academy of Sciences of the United States of America 84(22):7851-7855, National Academy of Sciences, United States (Nov. 1987).
Welch, E.M., et al., "PTC124 Targets Genetic Disorders Caused by Nonsense Mutations ," Nature 447(7140):87-91, Nature Publishing Group, England (May 2007).
Wengel, J., "Synthesis of 3'-C- and 4'-C-Branched Oligodeoxynucleotides and the Development of Locked Nucleic Acid (LNA)," Accounts of Chemical Research 32(4):301-310 (1999).
Wenz, D., "Cyclodextrins as Building Blocks for Supramolecular Structures and Functional Units," Angewandte Chemie International Edition in English 33(8):803-822 (May 1994).
Wilton, S.D., et al., "Antisense Oligonucleotide-induced Exon Skipping Across the Human Dystrophin Gene Transcript," Molecular Therapy 15(7):1288-1296, Cell Press, United States (Jul. 2007), (Exhibit No. 2121 filed in interferences 106,007 and 106,008 on Feb. 17, 2015.
Wilton, S.D., et al., "Specific Removal of the Nonsense Mutation From the Mdx Dystrophin mRNA Using Antisense Oligonucleotides," Neuromuscular Disorders 9(5):330-338, Pergamon Press, England (Jul. 1999).
Wolff, J.A., et al., "Direct Gene Transfer into Mouse Muscle in Vivo," Science 247(4949 Pt1):1465-1468, American Association for the Advancement of Science, United States (Mar. 1990).
Wu, B., et al., "Effective Rescue of Dystrophin Improves Cardiac Function in Dystrophin-deficient Mice by a Modified Morpholino Oligomer," Proceedings of the National Academy of Sciences of the United States of America 105(39):14814-14819, National Academy of Sciences, United States (Sep. 2008).
Wu, B., et al., "Long-term Rescue of Dystrophin Expression and Improvement in Muscle Pathology and Function in Dystrophic mdx Mice by Peptide-conjugated Morpholino," The American Journal of Pathology 181(2):392-400, Elsevier, United States (Aug. 2012).
Wu, B., et al., "One-year Treatment of Morpholino Antisense Oligomer Improves Skeletal and Cardiac Muscle Functions in Dystrophic Mdx Mice," Molecular Therapy 19(3):576-583, Cell Press, United States (Mar. 2011).

(56) References Cited

OTHER PUBLICATIONS

Wu, G.Y. and Wu, C.H., "Receptor-mediated Gene Delivery and Expression in Vivo," The Journal of Biological Chemistry 263(29):14621-14624, American Society for Biochemistry and Molecular Biology, United States (Oct. 1988).
Wu, R.P., et al., "Cell-penetrating Peptides as Transporters for Morpholino Oligomers: Effects of Amino Acid Composition on Intracellular Delivery and Cytotoxicity," Nucleic Acids Research 35(15):5182-5191, Oxford University Press, England (Aug. 2007).
Yamada, T., et al., "Synthesis of 2'-O-[2-(N-methylcarbamoyl)ethyl]ribonucleosides Using Oxa-michael Reaction and Chemical and Biological Properties of Oligonucleotide Derivatives Incorporating These Modified Ribonucleosides," The Journal of Organic Chemistry 76(9):3042-3053, American Chemical Society, United States (May 2011).
Yin, H., et al., "Cell-penetrating Peptide-conjugated Antisense Oligonucleotides Restore Systemic Muscle and Cardiac Dystrophin Expression and Function," Human Molecular Genetics 17(24):3909-3918, IRL Press, England (Dec. 2008).
Yin, H., et al., "Pip5 Transduction Peptides Direct High Efficiency Oligonucleotide-mediated Dystrophin Exon Skipping in Heart and Phenotypic Correction in mdx Mice," Molecular Therapy 19(7):1295-1303, Cell Press, United States (Jul. 2011).
Yokota T et al., "Efficacy of Systematic Morpholino Exon-Skipping in Duchenne Dystrophy Dogs," Annals of Neurology, 65(6):667-676, Wiley-Liss, United States (Jun. 2009), Exhibit No. 1214 filed in Interferences 106,007 and 106,008 on Feb. 17, 2015.
Yoo, B.H., et al., "2'-O-methyl-modified Phosphorothioate Antisense Oligonucleotides Have Reduced Non-specific Effects in Vitro," Nucleic Acids Research 32(6):2008-2016, Oxford University Press, England (Apr. 2004).
Youngblood, D.S., et al., "Stability of Cell-Penetrating Peptide-Morpholino Oligomer Conjugates in Human Serum and in Cells," Bioconjugate Chemistry 18(1):50-60, American Chemical Society, United States (Jan.-Feb. 2007).
Yue, Y., et al., "C-terminal-truncated Microdystrophin Recruits Dystrobrevin and Syntrophin to the Dystrophin-associated Glycoprotein Complex and Reduces Muscular Dystrophy in Symptomatic Utrophin/dystrophin Double-knockout Mice," Molecular Therapy 14(1):79-87, Cell Press, United States (Jul. 2006).
Betts, C., et al., "Pip6-PMO, A New Generation of Peptide-oligonucleotide Conjugates With Improved Cardiac Exon Skipping Activity for DMD Treatment," Molecular Therapy—Nucleic Acids e38: 1-13, Nature Publishing Group, United Kingdom (2012).
Godfrey, C., et al., "How much dystrophin is enough: the physiological consequences of different levels of dystrophin in the mdx mouse," Human Molecular Genetics 24:4225-4237, Oxford University Press, United Kingdom (2015).
Sazani, P., et al., "AVI-5038: Initial Efficacy and Safety Evaluation in Cynomolgus Moneleys," AVI BioPharma, Inc., 1 page.
Moulton, H., et al., "Morpholinos and their peptide conjugates: Therapeutic promise and challenge for Duchenne muscular dystrophy," Biochimia et Biophysica Acta 1798: 296-2303, Elsevier, Netherlands (2010).

Coenen-Stass, A., et al., "Identification of novel, therapy-responsive protein biomarkers in a mouse model of Duchenne muscular dystrophy by aptamer-based serum proteomics," Scientific Reports 5: 1-10, Nature, United Kingdom (2015).
Fletcher, S., et al., "Morpholino Oligomer-Mediated Exon Skipping Averts the Onset of Dystrophic Pathology in the mdx Mouse," Molecular Therapy 15:1587-1592, The American Society of Gene Therapy, United States (2007).
Burki, U., et al., "Development and Application of an Ultrasensitive Hybridization-Based ELISA Method for the Determination of Peptide-Conjugated Phosphorodiamidate Morpholino Oligonucleotides," Nucleic Acid Therapeutics 25: 275-284, Mary Ann Liebert, United States (2015).
Lu-Nguyen, N., et al., "Combination Antisense Treatment for Destructive Exon Skipping of Myostatin and Open Reading Frame Rescue of Dystrophin in Neonatal mdx Mice," Molecular Therapy 23:1341-1348, The American Society of Gene & Cell Therapy, United States (2015).
Betts, C., et al., Prevention of exercised induced cardiomyopathy following Pip-PMO treatment in dystrophic mdx mice, Scientific Reports 5: 1-9, Nature, United Kingdom (2015).
Jarver, P., et al., "Peptide-mediated Cell and In Vivo Delivery of Antisense Oligonucleotides and siRNA," Molecular Therapy—Nucleic Acids 1:1-27, American Society of Gene & Cell Therapy, United Kingdom (2012).
Office Action dated Apr. 24, 2019, in U.S. Appl. No. 15/993,267, Bestwick et al., filed May 30, 2018, 14 pages.
Genbank, "RP43-026J01, complete sequence," Accession No. CT485784.2, accessed at https://www.ncbi.nlm.nih.gov/nuccore/CT485784.2, accessed on Feb. 21, 2020, 43 pages.
Mitrpant; C et al., "Rational Design of Antisense Oligomer to Induce Dystrophin Exon Skipping," Mol Ther 17(8):1418-26, American Society of Gene & Cell Therapy, United States (2009).
Veltrop; M. et al., "A Dystrophic Duchenne Mouse Model for Testing Human Antisense Oligonucleotides," PLOS One 13(2):e0193289, Public Library of Science, United States (Feb. 2018).
Office Action dated Mar. 18, 2019, in U.S. Appl. No. 15/993,267, Bestwick et al., filed May 30, 2018, 13 pages.
Office Action dated Oct. 29, 2019, in U.S. Appl. No. 15/993,267, Bestwick et al., filed May 30, 2018, 9 pages.
Koo, T., et al., "Clinical Trials Using Antisense Oligonucleotides in Duchenne Muscular Dystrophy," Human Gene Therapy 24:479-488, Mary Ann Liebert, Inc, United States (2013).
Office Action dated Jan. 7, 2020, in U.S. Appl. No. 16/001,310, Passini, M. et al., filed Jun. 6, 2018, 20 pages.
Office Action dated Sep. 5, 2018, in U.S. Appl. No. 16/001,310, Passini, et al., filed Jun. 6, 2018, 20 pages.
Office Action dated Mar. 19, 2019, in U.S. Appl. No. 16/001,310, Passini, et al., filed Jun. 6, 2018, 25 pages.
Notice of Allowance dated Jan. 6, 2021, in U.S. Appl. No. 16/001,310, Passini et al., filed Jun. 6, 2018.
Office Action dated Aug. 27, 2021, in U.S. Appl. No. 17/245,735, Passini, et al., filed Apr. 30, 2021, 14 pages.
Notice of Allowance dated Dec. 8, 2021, in U.S. Appl. No. 17/245,735, Passini, et al., filed Apr. 30, 2021.
Notice of Allowance dated Apr. 22, 2020, in U.S. Appl. No. 15/993,267, Bestwick et al., filed May 30, 2018.

b) Exon 50 Deletion Disrupts Reading Frame    Nonfunctional, Unstable Dystrophin Figure 5C
60 Days
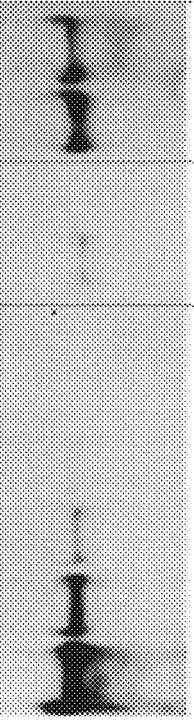
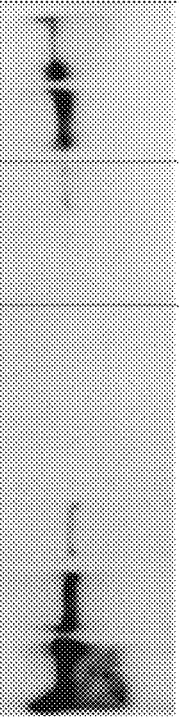
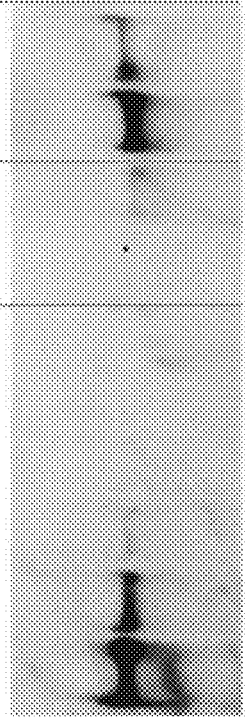
Figure 5D
90 Days

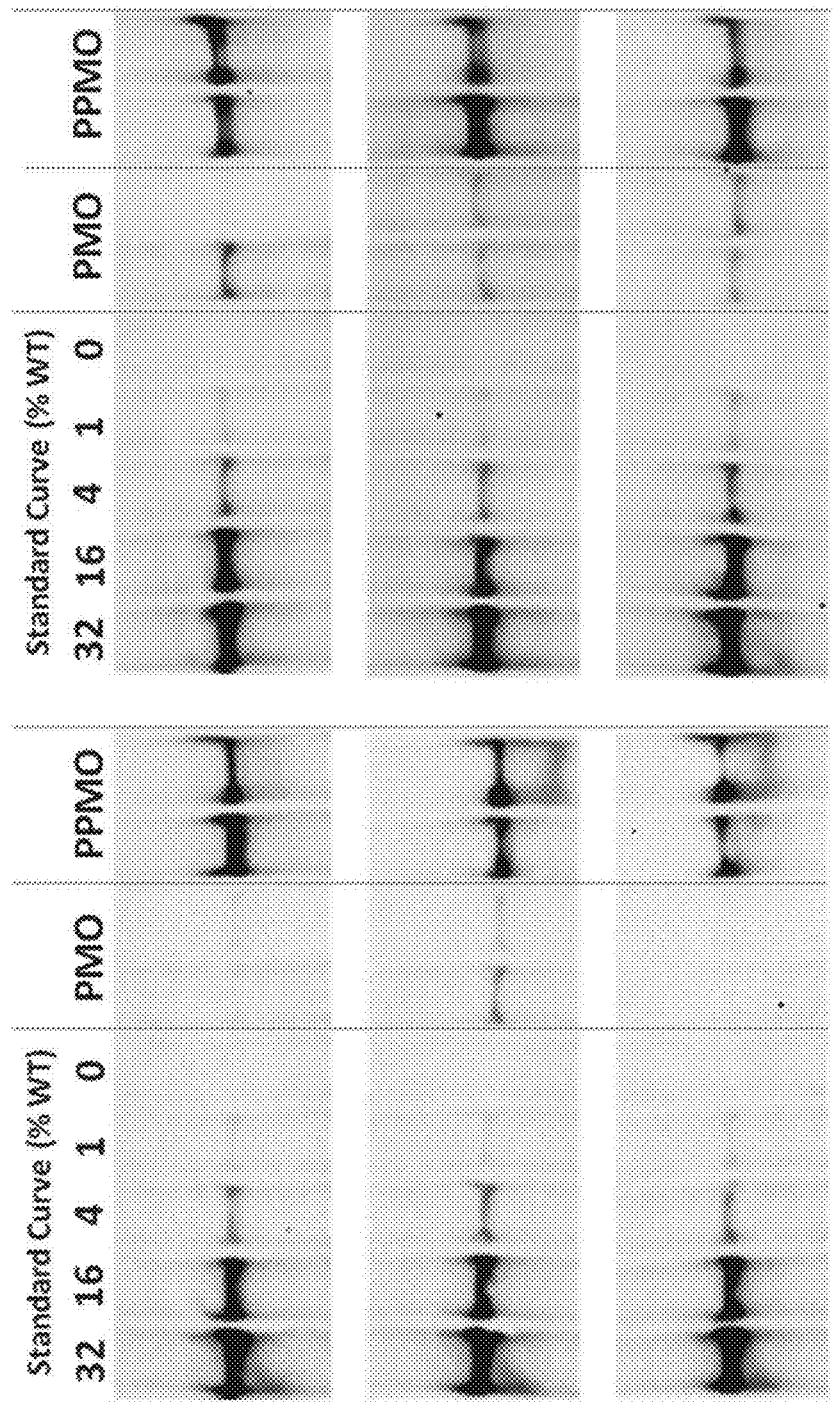

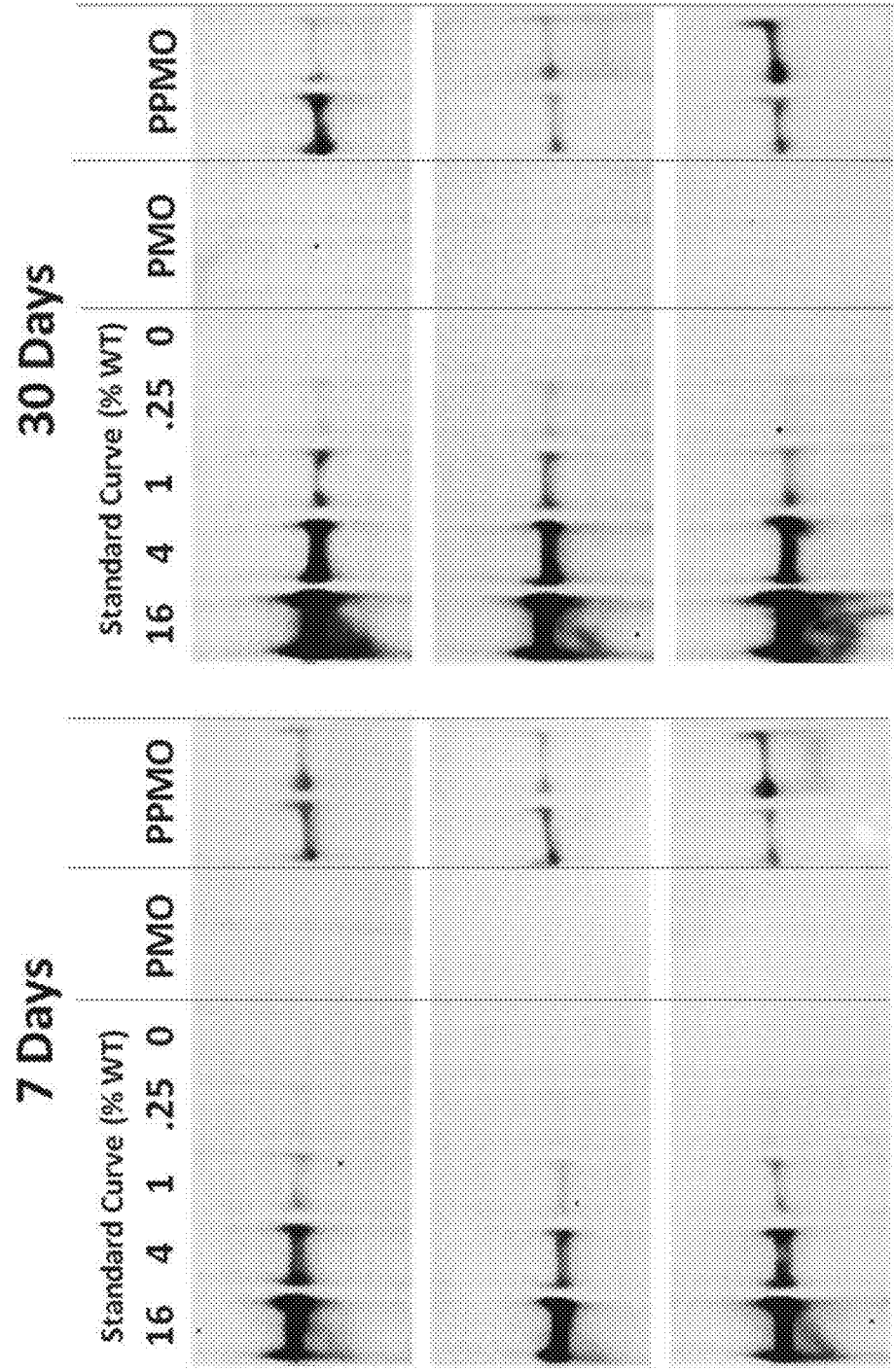

| Cycle No.: Subunit (SU) | Pre-coupling Treatment | | | | Coupling Cycle | | Post-Coupling Treatment | |
|---|---|---|---|---|---|---|---|---|
| | 1 | 2 | 3 | 4 | | | 1 | 2 |
| | 30% TFE/DCM Wash | CYTFA Solution[1] | Neutralization Solution | DCM Wash | Quantity SU (g) NEM (L) DMI (L) | RT Coupling Time (Hrs.) | DCM Wash | 30% TFE/DCM Wash |
| 1:DPG | 5.5L | a) 5.5L b) 5.5L, 122ml | 3x5.5L | 5.5L | 536.7g; 195 ml NEM; 3.2L DMI | 5 | 5.5L | 2x5.5L |
| 2:T | 7.0L | a) 7L b) 7L, 158ml | 3x7L | 2x7L | 468.2g and 195ml NEM 3.2L DMI | 4.25 | 7L | 2x7L |
| 3:T | 8L | a) 8L b) 8L, 182ml | 3x8L | 2x8L | 536.7g; 195ml NEM; 3.4L DMI | 4.25 | 8L | 2x8L |
| 4:DPG | 9L | a) 9L b) 9L, 206ml | 3x9L | 2x9L | 536.7g; 195ml NEM; 3.6L DMI | 4.25 | 9L | 2x9L |
| 5:C | 9.5L | a) 9.5L b) 9.5L, 220ml | 3x9.5L | 2x9.5L | 555.2g; 195ml NEM; 3.4L DMI | 4.25 | 9.5L | 2x9.5L |
| 6:C | 10L | a) 10L b) 10L, 232ml | 3x10L | 2x10L | 555.2g; 195ml NEM; 3.45L DMI | 4.25 | 10L | 2x10L |
| 7:T | 11L | a) 11L b) 11L, 256ml | 3x11L | 2x11L | 536.7g; 195ml NEM; 3.57L | 4.25 | 11L | 2x11L |

[1] ml indicates the amount of 1:1 NEM/DCM

Figure 18

| Cycle No.: Subunit (SU) | Pre-coupling Treatment | | | | Coupling Cycle | | Post-Coupling Treatment | |
|---|---|---|---|---|---|---|---|---|
| | 1 | 2 | 3 | 4 | | | 1 | 2 |
| | 30% TFE/DCM Wash | CYTFA Solution[1] | Neutralization Solution | DCM Wash | Quantity SU (g) NEM (L) DMI (L) DMI | RT Coupling Time (Hrs.) | DCM Wash | 30% TFE/DCM Wash |
| 8:C | 11L | a) 11L b) 11L, 256ml | 3x11L | 2x11L | 555.2g; 195ml NEM; 3.64L DMI | 4.25 | 11L | 2x11L |
| 9:C | 11.5L | a) 11.5L b) 11.5L, 268ml | 3x11.5L | 2x 11.5L | 468.2g; 195ml NEM; 3.72L DMI | 4.25 | 11.5L | 2x11.5L |
| 10:DPG | 12L | a) 12L b) 12L, 280ml | 3x12L | 2x12L | 536.7g; 195ml NEM; 3.96L DMI | 4.25 | 12L | 2x12L |
| 11:DPG | 13.5L | a) 13.5L b) 13.5L, 204ml | 3x13.5L | 2x 13.5L | 721.7g; 253ml NEM; 4.02L DMI | 4.25 | 13.5L | 2x13.5L |
| 12:T | 13.5L | a) 13.5L b) 13.5L, 204ml | 3x13.5L | 2x 13.5L | 721.7g; 253ml NEM; 4.02L DMI | 4.25 | 13.5L | 2x13.5L |
| 13:T | 14L | a) 14L b) 14L, 216ml | 3x14L | 2x14L | 941.9g; 253ml NEM; 4.02L DMI | 4.25 | 14L | 2x14L |
| 14:C | 14.5L | a) 14.5L b) 14.5L, 228ml | 3x14.5L | 2x 14.5L | 941.9g; 253ml NEM; 4.1L DMI | 4.25 | 14.5L | 2x14.5L |
| 15:T | 15.5L | a) 15.5L b) 15.5L, | 3x15.5L | 2x 15.5L | 721.7g; 253ml | 4.25 | 15.5L | 2x15.5L |

Figure 18 (continued)

| Cycle No.: Subunit (SU) | Pre-coupling Treatment | | | | Coupling Cycle | | Post-Coupling Treatment | |
|---|---|---|---|---|---|---|---|---|
| | 1 | 2 | 3 | 4 | | | 1 | 2 |
| | 30% TFE/DCM Wash | CYTFA Solution[1] | Neutralization Solution | DCM Wash | Quantity SU (g) NEM (L) DMI (L) | RT Coupling Time (Hrs.) | DCM Wash | 30% TFE/DCM Wash |
| | | 254ml | | | NEM; 4.26L DMI | | | |
| 16:DPG | 15.5L | a) 15.5L b) 15.5L, 254ml | 3x15.5L | 2x 15.5L | 721.7g; 253ml NEM; 4.26L DMI | 4.25 | 15.5L | 2x15.5L |
| 17:A | 16L | a) 16L b) 16L, 366ml | 3x16L | 2x16L | 941.9g; 253ml NEM; 4.4L DMI | 4.75 | 16L | 2x16L |
| 18:A | 16.5L | a) 16.5L b) 16.5L, 378ml | 3x16.5L | 2x 16.5L | 721.7g; 253ml NEM; 4.4L DMI | 4.25 | 16.5L | 2x16.5L |
| 19: DPG | 16.5L | a) 16.5L b) 16.5L, 378ml | 3x16.5L | 2x 16.5L | 608.7g; 253ml NEM; 4.57L DMI | 4.25 | 16.5L | 2x16.5L |
| 20:DPG | 17L | a) 17L b) 17L, 390ml | 3x17L | 2x17L | 941.9g; 253ml NEM; 4.57L DMI | 4.75 | 17L | 2x17L |
| 21:T | 17L | a) 17L b) 17L, 390ml | 3x17L | 2x17L | 1159.2g; 311ml NEM; 4.72L DMI | 4.25 | 17L | 2x17L |
| 22: DPG | 17.5L | a) 17.5L b) 17.5L, 402ml | 3x17.5L | 2x 17.5L | 858.7g; 311ml NEM; 4.72L DMI | 4.75 | 17.5L | 2x17.5L |

Figure 18 (continued)

| Cycle No.: Subunit (SU) | Pre-coupling Treatment | | | | Coupling Cycle | | Post-Coupling Treatment | |
|---|---|---|---|---|---|---|---|---|
| | 1 | 2 | 3 | 4 | | | 1 | 2 |
| | 30% TFE/DCM Wash | CYTFA Solution[1] | Neutralization Solution | DCM Wash | Quantity SU (g) NEM (L) DMI (L) | RT Coupling Time (Hrs.) | DCM Wash | 30% TFE/DCM Wash |
| 23:T | 17.5L | a) 17.5L b) 17.5L, 402ml | 3x17.5L | 2x 17.5L | 888.3g; 311ml NEM; 4.88L DMI | 4.25 | 17.5L | 2x17.5L |
| 24:T | 18L | a) 18L b) 18L, 414ml | 3x18L | 2x18L | 749.1g; 311ml NEM; 4.95L DMI | 4.25 | 18L | 2x18L |
| 25:C | 18L | a) 18L b) 18L, 414ml | 3x18L | 2x18L | 749.1g; 311ml NEM; 5.1L DMI | 4.25 | 18L | 2x18L |

Cynomolgus Dosing Schedule

| Group | Compound | Dose (mg/kg) | Number per group | Delivery Strategy |
|---|---|---|---|---|
| 1 | PPMO#1 | 20 | 3 | |
| 2 | PPMO#1 | 40 | 3 | |
| 3 | PPMO#1 | 80 | 3 | 1 2 3 4 Weeks ●—●—●—●—[SAC] |
| 4 | PPMO#1 | 160 | 3 | Once weekly dosing, 4 total doses |
| 5 | PMO#1 | 40 | 3 | Animals are sacrificed 48 hours after last dose, on day 22 |
| 6 | Saline | 0 | 2 | |
| 7 | PPMO#1 | 40 | 2 | 1　　　　　30 days ●————[SAC]　Single dose on day 1 with 4 week recovery |
| 8 | PPMO#1 | 40 | 2 | 1　　　　　　　　60 days ●————————[SAC]　Single dose on day 1 with 8 week recovery |

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:

```
<223> OTHER INFORMATION: Synthetic

<400> SEQUENCE: 1
ctgttccaaa tcctgcattg ttgcc                                             25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ggccaaacct cggcttacct gaaat                                             25

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Arg Arg Arg Arg Arg Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Arg Arg Arg Arg Arg Arg Gly
1               5

<210> SEQ ID NO 5
<211> LENGTH: 20
<212> TYPE: DNA
<213> ORGANISM: Artificial Sequence
<220> FEATURE:
<223> OTHER INFORMATION: Human exon 50 binding forward primer

<400> SEQUENCE: 5
ctctgagtgg aaggcggtaa                                                   20

<210> SEQ ID NO 6
<211> LENGTH: 20
<212> TYPE: DNA
<213> ORGANISM: Artificial Sequence
<220> FEATURE:
<223> OTHER INFORMATION: Human exon 53 binding forward primer

<400> SEQUENCE: 6
acctgctcag cttcttcctt                                                   20

<210> SEQ ID NO 7
<211> LENGTH: 21
<212> TYPE: DNA
<213> ORGANISM: Artificial Sequence
<220> FEATURE:
<223> OTHER INFORMATION: Mouse exon 23 binding forward primer

<400> SEQUENCE: 7
cacatctttg atggtgtgag g                                                 21
```

```
<210> SEQ ID NO 8
<211> LENGTH: 22
<212> TYPE: DNA
<213> ORGANISM: Artificial Sequence
<220> FEATURE:
<223> OTHER INFORMATION: Mouse exon 23 binding reverse primer

<400> SEQUENCE: 8
caacttcagc catccatttc tg                                              22

<210> SEQ ID NO 9
<211> LENGTH: 25
<212> TYPE: DNA
<213> ORGANISM: Artificial Sequence
<220> FEATURE:
<223> OTHER INFORMATION: PMO-G

<400> SEQUENCE: 9
gttgcctccg gttctgaagg tgttc                                           25

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ctccaacatc aaggaagatg gcatttctag                                      30
```

EXON SKIPPING OLIGOMER CONJUGATES FOR MUSCULAR DYSTROPHY

REFERENCE TO A SEQUENCE LISTING SUBMITTED ELECTRONICALLY VIA EFS-WEB

The content of the electronically submitted sequence listing in ASCII text file (Name: 4140_0200004_Seq-Listing_ST25; Size: 2,254 bytes; and Date of Creation: Jul. 23, 2020) is herein incorporated by reference in its entirety.

FIELD OF THE DISCLOSURE

The present disclosure relates to novel antisense oligomer conjugates suitable for exon 52 skipping in the human dystrophin gene and pharmaceutical compositions thereof. The disclosure also provides methods for inducing exon 52 skipping using the novel antisense oligomers and antisense oligomer conjugates, methods for producing dystrophin in a subject having a mutation of the dystrophin gene that is amenable to exon 52 skipping, and methods for treating a subject having a mutation of the dystrophin gene that is amenable to exon 52 skipping.

BACKGROUND OF THE DISCLOSURE

Antisense technologies are being developed using a range of chemistries to affect gene expression at a variety of different levels (transcription, splicing, stability, translation). Much of that research has focused on the use of antisense compounds to correct or compensate for abnormal or disease-associated genes in a wide range of indications. Antisense molecules are able to inhibit gene expression with specificity, and because of this, many research efforts concerning oligomers as modulators of gene expression have focused on inhibiting the expression of targeted genes or the function of cis-acting elements. The antisense oligomers are typically directed against RNA, either the sense strand (e.g., mRNA), or minus-strand in the case of some viral RNA targets. To achieve a desired effect of specific gene down-regulation, the oligomers generally either promote the decay of the targeted mRNA, block translation of the mRNA or block the function of cis-acting RNA elements, thereby effectively preventing either de novo synthesis of the target protein or replication of the viral RNA.

However, such techniques are not useful where the object is to up-regulate production of the native protein or compensate for mutations that induce premature termination of translation, such as nonsense or frame-shifting mutations. In these cases, the defective gene transcript should not be subjected to targeted degradation or steric inhibition, so the antisense oligomer chemistry should not promote target mRNA decay or block translation.

In a variety of genetic diseases, the effects of mutations on the eventual expression of a gene can be modulated through a process of targeted exon skipping during the splicing process. The splicing process is directed by complex multi-component machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short, semi-conserved RNA segments to which various nuclear splicing factors that are then involved in the splicing reactions bind. By changing the way the splicing machinery reads or recognizes the motifs involved in pre-mRNA processing, it is possible to create differentially spliced mRNA molecules. It has now been recognized that the majority of human genes are alternatively spliced during normal gene expression, although the mechanisms involved have not been identified. Bennett et al. (U.S. Pat. No. 6,210,892) describe antisense modulation of wild-type cellular mRNA processing using antisense oligomer analogs that do not induce RNAse H-mediated cleavage of the target RNA. This finds utility in being able to generate alternatively spliced mRNAs that lack specific exons (see, e.g., as described by Sazani, Kole, et al. 2007 for the generation of soluble TNF superfamily receptors that lack exons encoding membrane spanning domains).

In cases where a normally functional protein is prematurely terminated because of mutations therein, a means for restoring some functional protein production through antisense technology has been shown to be possible through intervention during the splicing processes, and that if exons associated with disease-causing mutations can be specifically deleted from some genes, a shortened protein product can sometimes be produced that has similar biological properties of the native protein or has sufficient biological activity to ameliorate the disease caused by mutations associated with the exon (see e.g., Sierakowska, Sambade et al. 1996; Wilton, Lloyd et al. 1999; van Deutekom, Bremmer-Bout et al. 2001; Lu, Mann et al. 2003; Aartsma-Rus, Janson et al. 2004). Kole et al. (U.S. Pat. Nos. 5,627,274; 5,916,808; 5,976,879; and 5,665,593) disclose methods of combating aberrant splicing using modified antisense oligomer analogs that do not promote decay of the targeted pre-mRNA. Bennett et al. (U.S. Pat. No. 6,210,892) describe antisense modulation of wild-type cellular mRNA processing also using antisense oligomer analogs that do not induce RNAse H-mediated cleavage of the target RNA.

The process of targeted exon skipping is likely to be particularly useful in long genes where there are many exons and introns, where there is redundancy in the genetic constitution of the exons or where a protein is able to function without one or more particular exons. Efforts to redirect gene processing for the treatment of genetic diseases associated with truncations caused by mutations in various genes have focused on the use of antisense oligomers that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD.

A less severe form of muscular dystrophy, Becker muscular dystrophy (BMD) has been found to arise where a mutation, typically a deletion of one or more exons, results in a correct reading frame along the entire dystrophin transcript, such that translation of mRNA into protein is not prematurely terminated. If the joining of the upstream and downstream exons in the processing of a mutated dystrophin pre-mRNA maintains the correct reading frame of the gene, the result is an mRNA coding for a protein with a short internal deletion that retains some activity, resulting in a Becker phenotype.

For many years it has been known that deletions of an exon or exons which do not alter the reading frame of a dystrophin protein would give rise to a BMD phenotype, whereas an exon deletion that causes a frame-shift will give rise to DMD (Monaco, Bertelson et al. 1988). In general, dystrophin mutations including point mutations and exon deletions that change the reading frame and thus interrupt proper protein translation result in DMD. It should also be noted that some BMD and DMD patients have exon deletions covering multiple exons.

Modulation of mutant dystrophin pre-mRNA splicing with antisense oligoribonucleotides has been reported both in vitro and in vivo (see e.g., Matsuo, Masumura et al. 1991; Takeshima, Nishio et al. 1995; Pramono, Takeshima et al. 1996; Dunckley, Eperon et al. 1997; Dunckley, Manoharan et al. 1998; Wilton, Lloyd et al. 1999; Mann, Honeyman et al. 2002; Errington, Mann et al. 2003).

Antisense oligomers have been specifically designed to target specific regions of the pre-mRNA, typically exons to induce the skipping of a mutation of the DMD gene thereby restoring these out-of-frame mutations in-frame to enable the production of internally shortened, yet functional dystrophin protein. Such antisense oligomers have been known to target completely within the exon (so called exon internal sequences) or at a splice donor or splice acceptor junction that crosses from the exon into a portion of the intron.

The discovery and development of such antisense oligomers for DMD has been an area of prior research. These developments include those from: (1) the University of Western Australia and Sarepta Therapeutics (assignee of this application): WO 2006/000057; WO 2010/048586; WO 2011/057350; WO 2014/100714; WO 2014/153240; WO 2014/153220; (2) Academisch Ziekenhuis Leiden/Prosensa Technologies (now BioMarin Pharmaceutical): WO 02/24906; WO 2004/083432; WO 2004/083446; WO 2006/112705; WO 2007/133105; WO 2009/139630; WO 2009/054725; WO 2010/050801; WO 2010/050802; WO 2010/123369; WO 2013/112053; WO 2014/007620; (3) Carolinas Medical Center: WO 2012/109296; (4) Royal Holloway: patents and applications claiming the benefit of, and including, US Serial Nos. 61/096,073 and 61/164,978; such as U.S. Pat. No. 8,084,601 and US 2017-0204413 (4) JCR Pharmaceuticals and Matsuo: U.S. Pat. No. 6,653,466; patents and applications claiming the benefit of, and including, JP 2000-125448, such as U.S. Pat. No. 6,653,467; patents and applications claiming the benefit of, and including, JP 2000-256547, such as U.S. Pat. No. 6,727,355; WO 2004/048570; (5) Nippon Shinyaku: WO 2012/029986; WO 2013/100190; WO 2015/137409; WO 2015/194520; and (6) Association Institut de Myologie/Universite Pierre et Marie Curie/Universitat Bern/Centre national de la Recherche Scientifique/Synthena AG: WO 2010/115993; WO 2013/053928.

The discovery and development of antisense oligomers conjugated to cell-penetrating peptides for DMD has also been an area of research (see PCT Publication No. WO 2010/048586; Wu, B. et al., The American Journal of Pathology, Vol. 181 (2): 392-400, 2012; Wu, R. et al., Nucleic Acids Research, Vol. 35 (15): 5182-5191, 2007; Mulders, S. et al., 19$^{th}$ International Congress of the World Muscle Society, Poster Presentation Berlin, October 2014; Bestas, B. et al., The Journal of Clinical Investigation, doi: 10.1172/JCI76175, 2014; Jearawiriyapaisarn, N. et al., Molecular Therapy, Vol. 16(9): 1624-1629, 2008; Jearawiriyapaisarn, N. et al., Cardiovascular Research, Vol. 85: 444-453, 2010; Moulton, H. M. et al., Biochemical Society Transactions, Vol. 35 (4): 826-828, 2007; Yin, H. et al., Molecular Therapy, Vol. 19 (7): 1295-1303, 2011; Abes, R. et al., J Pept. Sci., Vol. 14: 455-460, 2008; Lebleu, B. et al., Advanced Drug Delivery Reviews, Vol. 60: 517-529, 2008; McClorey, G. et al., Gene Therapy, Vol. 13: 1373-1381, 2006; Alter, J. et al., Nature Medicine, Vol. 12 (2): 175-177, 2006; and Youngblood, D. et al., American Chemical Society, Bioconjugate Chem., 2007, 18 (1), pp 50-60).

Cell-penetrating peptides (CPP), for example, an arginine-rich peptide transport moiety, may be effective to enhance penetration of, for example, an antisense oligomer conjugated to the CPP, into a cell.

Despite these efforts, there remains a need for improved antisense oligomers that target exon 52 and corresponding pharmaceutical compositions that are potentially useful for therapeutic methods for producing dystrophin and treating DMD.

SUMMARY OF THE DISCLOSURE

The antisense oligomer conjugates provided herein include an antisense oligomer moiety conjugated to a CPP. In one aspect, the disclosure provides antisense oligomer conjugates comprising:

an antisense oligomer of 25 subunits in length capable of binding a selected target to induce exon skipping in the human dystrophin gene, wherein the antisense oligomer comprises a sequence of bases that is complementary to an exon 52 target region of the dystrophin pre-mRNA designated as an annealing site; and a cell-penetrating peptide (CPP) conjugated to the antisense oligomer by a linker moiety.

In some embodiments, the annealing site is H52A(−01+24).

In some embodiments, the bases of the antisense oligomer are linked to morpholino ring structures, wherein the morpholino ring structures are joined by phosphorous-containing intersubunit linkages joining a morpholino nitrogen of one ring structure to a 5' exocyclic carbon of an adjacent ring structure. In certain embodiments, the cell-penetrating peptide is six arginine units ("$R_6$") and the linker moiety is a glycine. In some embodiments, the antisense oligomer comprises a sequence of bases designated as SEQ ID NO: 1.

In another aspect, the disclosure provides antisense oligomers of 25 subunits in length capable of binding a selected target to induce exon skipping in the human dystrophin gene, wherein the antisense oligomer comprises a sequence of bases that is complementary to an exon 52 target region of the dystrophin pre-mRNA designated as an annealing site.

In some embodiments, the annealing site is H52A(−01+24).

In some embodiments, the bases of the antisense oligomer are linked to morpholino ring structures, wherein the morpholino ring structures are joined by phosphorous-containing intersubunit linkages joining a morpholino nitrogen of one ring structure to a 5' exocyclic carbon of an adjacent ring structure. In some embodiments, the antisense oligomer comprises a sequence of bases designated as SEQ ID NO: 1.

In various aspects, the disclosure provides antisense oligomer conjugates which may be according to Formula (I):

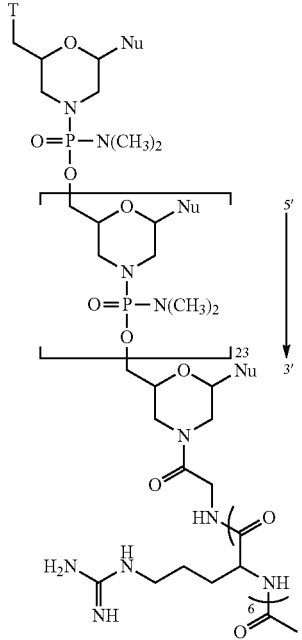

(I)

or a pharmaceutically acceptable salt thereof, wherein:
each Nu is a nucleobase which taken together form a targeting sequence; and
T is a moiety selected from:

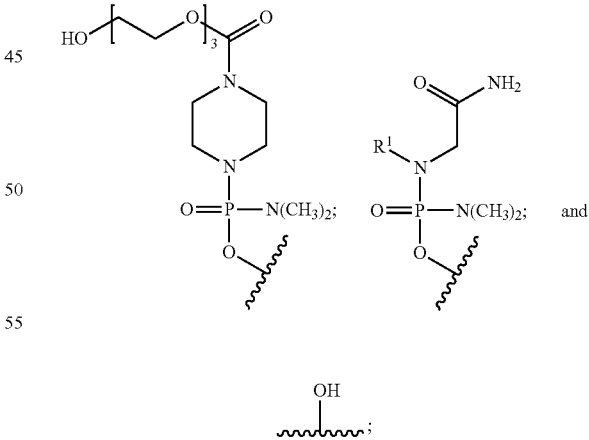

$R^1$ is $C_1$-$C_6$ alkyl;

wherein the targeting sequence is complementary to an exon 52 annealing site in the dystrophin pre-mRNA designated as H52A(−01+24).

In another aspect, the disclosure provides antisense oligomer conjugates of Formula (V):

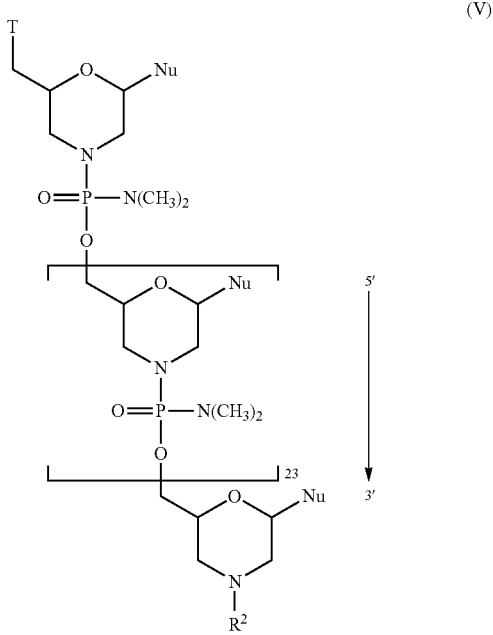

(V)

or a pharmaceutically acceptable salt thereof, wherein:
each Nu is a nucleobase which taken together form a targeting sequence;
T is a moiety selected from:

$R^1$ is $C_1$-$C_6$ alkyl; and
$R^2$ is selected from H or acetyl, wherein the targeting sequence is complementary to an exon 52 annealing site in the dystrophin pre-mRNA designated as H52A(−01+24).

In another aspect, the disclosure provides antisense oligomer conjugates of Formula (IVA):

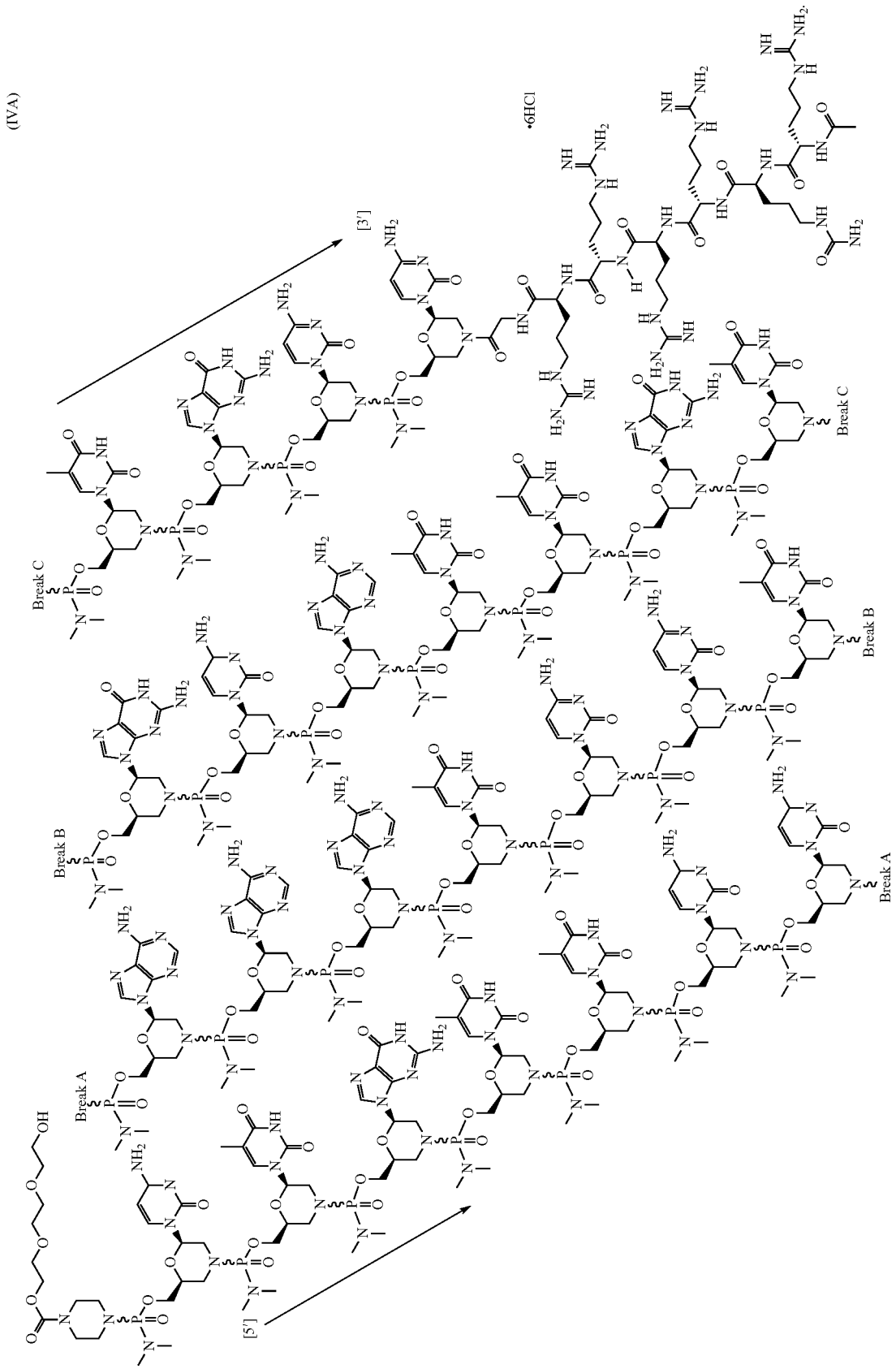

In another aspect, the disclosure provides pharmaceutical compositions that include the antisense oligomers or antisense oligomer conjugates of the disclosure, and a pharmaceutically acceptable carrier. In some embodiments, the pharmaceutically acceptable carrier is a saline solution that includes a phosphate buffer.

In another aspect, the disclosure provides a method for treating Duchenne muscular dystrophy (DMD) in a subject in need thereof wherein the subject has a mutation of the dystrophin gene that is amenable to exon 52 skipping, the method comprising administering to the subject an antisense oligomer or antisense oligomer conjugate of the disclosure. The disclosure also addresses the use of antisense oligomers or antisense oligomer conjugates of the disclosure, for the manufacture of a medicament for treatment of Duchenne muscular dystrophy (DMD) in a subject in need thereof wherein the subject has a mutation of the dystrophin gene that is amenable to exon 52 skipping.

In another aspect, the disclosure provides a method of restoring an mRNA reading frame to induce dystrophin production in a subject having a mutation of the dystrophin gene that is amenable to exon 52 skipping, the method comprising administering to the subject an antisense oligomer or an antisense oligomer conjugate of the disclosure. In another aspect, the disclosure provides a method of excluding exon 52 from dystrophin pre-mRNA during mRNA processing in a subject having a mutation of the dystrophin gene that is amenable to exon 52 skipping, the method comprising administering to the subject an antisense oligomer or an antisense oligomer conjugate of the disclosure. In another aspect, the disclosure provides a method of binding exon 52 of dystrophin pre-mRNA in a subject having a mutation of the dystrophin gene that is amenable to exon 52 skipping, the method comprising administering to the subject an antisense oligomer or an antisense oligomer conjugate of the disclosure.

In another aspect, the disclosure provides an antisense oligomer or an antisense oligomer conjugate of the disclosure herein for use in therapy. In certain embodiments, the disclosure provides an antisense oligomer or an antisense oligomer conjugate of the disclosure for use in the treatment of Duchenne muscular dystrophy. In certain embodiments, the disclosure provides an antisense oligomer or an antisense oligomer conjugate of the disclosure for use in the manufacture of a medicament for use in therapy. In certain embodiments, the disclosure provides an antisense oligomer or an antisense oligomer conjugate of the disclosure for use in the manufacture of a medicament for the treatment of Duchenne muscular dystrophy.

In another aspect, the disclosure also provides kits for treating Duchenne muscular dystrophy (DMD) in a subject in need thereof wherein the subject has a mutation of the dystrophin gene that is amenable to exon 52 skipping, which kits comprise at least an antisense oligomer or an antisense oligomer conjugate of the present disclosure, packaged in a suitable container and instructions for its use.

These and other objects and features will be more fully understood when the following detailed description of the disclosure is read in conjunction with the figures.

BRIEF DESCRIPTION OF THE FIGURES

FIGS. 5A-5D provide representative images of Western Blot analysis measuring dystrophin protein in the quadriceps of mdx mice treated with PMO (PMO 4225) or PPMO (PPMO4225) for different time points [7 days (5A), 30 days (5B), 60 days (5C), and 90 days (5D)].

FIGS. 7A-7D provide representative images of Western Blot analysis measuring dystrophin protein in the diaphragm of mdx mice treated with PMO (PMO 4225) or PPMO (PPMO4225) for different time points [7 days (7A), 30 days (7B), 60 days (7C) and 90 days (7D)].

FIG. 9A-9D provide representative images of Western Blot analysis measuring dystrophin protein in the heart of mdx mice treated with PMO (PMO 4225) or PPMO (PPMO4225) for different time points [7 days (9A), 30 days (9B), 60 days (9C) and 90 days (9D)].

FIG. 18 shows the coupling cycles performed by PMO Synthesis Method B.

FIG. 20 provides a dosing schedule for intravenous injection of PPMO #1, PMO #1 (from Example 3), or saline into intact muscle tissues of cynomolgus monkeys.

DETAILED DESCRIPTION OF THE DISCLOSURE

Figure 1:
FIG. 1 depicts a section of normal dystrophin pre-mRNA and mature mRNA.

Embodiments of the present disclosure relate generally to improved antisense oligomers and antisense oligomer conjugates, and methods of use thereof, which are specifically designed to induce exon skipping in the human dystrophin gene. Dystrophin plays a vital role in muscle function, and various muscle-related diseases are characterized by mutated forms of this gene. Hence, in certain embodiments, the improved antisense oligomers and antisense oligomer conjugates described herein induce exon skipping in mutated forms of the human dystrophin gene, such as the mutated dystrophin genes found in Duchenne muscular dystrophy (DMD) and Becker muscular dystrophy (BMD).

Due to aberrant mRNA splicing events caused by mutations, these mutated human dystrophin genes either express defective dystrophin protein or express no measurable dystrophin at all, a condition that leads to various forms of muscular dystrophy. To remedy this condition, the antisense oligomers and antisense oligomer conjugates of the present disclosure hybridize to selected regions of a pre-processed mRNA of a mutated human dystrophin gene, induce exon skipping and differential splicing in that otherwise aberrantly spliced dystrophin mRNA, and thereby allow muscle cells to produce an mRNA transcript that encodes a functional dystrophin protein. In certain embodiments, the resulting dystrophin protein is not necessarily the "wild-type" form of dystrophin, but is rather a truncated, yet functional, form of dystrophin.

By increasing the levels of functional dystrophin protein in muscle cells, these and related embodiments are useful in the prophylaxis and treatment of muscular dystrophy, especially those forms of muscular dystrophy, such as DMD and BMD, that are characterized by the expression of defective dystrophin proteins due to aberrant mRNA splicing. The specific antisense oligomers and antisense oligomer conjugates described herein further provide improved dystrophin-exon-specific targeting over other oligomers, and thereby offer significant and practical advantages over alternate methods of treating relevant forms of muscular dystrophy.

Thus, the disclosure relates to antisense oligomer conjugates comprising: an antisense oligomer of 25 subunits in length capable of binding a selected target to induce exon skipping in the human dystrophin gene, wherein the antisense oligomer comprises a sequence of bases that is complementary to an exon 52 target region of the dystrophin pre-mRNA designated as an annealing site; and a cell-penetrating peptide (CPP) conjugated to the antisense oligomer by a linker moiety.

The disclosure also relates to antisense oligomers of 25 subunits in length capable of binding a selected target to induce exon skipping in the human dystrophin gene, wherein the antisense oligomer comprises a sequence of bases that is complementary to an exon 52 target region of the dystrophin pre-mRNA designated as an annealing site.

In some embodiments of the antisense oligomers and the antisense oligomer conjugates of the disclosure, the annealing site is H52A(-01+24).

In some embodiments, the bases of the antisense oligomer are linked to morpholino ring structures, wherein the morpholino ring structures are joined by phosphorous-containing intersubunit linkages joining a morpholino nitrogen of one ring structure to a 5' exocyclic carbon of an adjacent ring structure. In certain embodiments, the cell-penetrating peptide is $R_6$ and the linker moiety is a glycine. In some embodiments, the antisense oligomer comprises the sequence of bases designated as SEQ ID NO: 1, wherein each thymine base (T) is optionally a uracil base (U).

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

I. Definitions

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group includes one to six carbon atoms, i.e., $C_1$ to $C_6$ alkyl. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, sec-butyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo, or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

"Amenable to exon 52 skipping" as used herein with regard to a subject or patient is intended to include subjects and patients having one or more mutations in the dystrophin gene which, absent the skipping of exon 52 of the dystrophin pre-mRNA, causes the reading frame to be out-of-frame thereby disrupting translation of the pre-mRNA leading to an inability of the subject or patient to produce functional or semi-functional dystrophin. Examples of mutations in the dystrophin gene that are amenable to exon 52 skipping include, e.g., deletion of: exons 2 to 51, exons 8 to 51, exons 20 to 51, exons 22 to 51, exon 51, exon 53, exons 53 to 55, exons 53 to 57, exons 53 to 59, exons 53 to 60, exons 53 to 67, exons 53 to 69, exons 53 to 75, and exons 53 to 78. Determining whether a patient has a mutation in the dystrophin gene that is amenable to exon skipping is well within the purview of one of skill in the art (see, e.g., Aartsma-Rus et al. (2009) Hum Mutat. 30:293-299; Gurvich et al., Hum Mutat. 2009; 30(4) 633-640; and Fletcher et al. (2010) Molecular Therapy 18(6) 1218-1223.).

The term "oligomer" as used herein refers to a sequence of subunits connected by intersubunit linkages. In certain instances, the term "oligomer" is used in reference to an "antisense oligomer." For "antisense oligomers," each subunit consists of: (i) a ribose sugar or a derivative thereof; and (ii) a nucleobase bound thereto, such that the order of the base-pairing moieties forms a base sequence that is complementary to a target sequence in a nucleic acid (typically an RNA) by Watson-Crick base pairing, to form a nucleic acid:oligomer heteroduplex within the target sequence with the proviso that either the subunit, the intersubunit linkage, or both are not naturally occurring. In certain embodiments, the antisense oligomer is a PMO. In other embodiments, the antisense oligomer is a 2'-O-methyl phosphorothioate. In other embodiments, the antisense oligomer of the disclosure is a peptide nucleic acid (PNA), a locked nucleic acid (LNA), or a bridged nucleic acid (BNA) such as 2'-O,4'-C-ethylene-bridged nucleic acid (ENA). Additional exemplary embodiments are described herein.

The terms "complementary" and "complementarity" refer to two or more oligomers (i.e., each comprising a nucleobase sequence) that are related with one another by Watson-Crick base-pairing rules. For example, the nucleobase sequence "T-G-A (5'→3')," is complementary to the nucleobase sequence "A-C-T (3'→5')." Complementarity may be "partial," in which less than all of the nucleobases of a given nucleobase sequence are matched to the other nucleobase sequence according to base pairing rules. For example, in some embodiments, complementarity between a given nucleobase sequence and the other nucleobase sequence may be about 70%, about 75%, about 80%, about 85%, about 90% or about 95%. Or, there may be "complete" or "perfect" (100%) complementarity between a given nucleobase sequence and the other nucleobase sequence to continue the example. The degree of complementarity between nucleobase sequences has significant effects on the efficiency and strength of hybridization between the sequences.

The terms "effective amount" and "therapeutically effective amount" are used interchangeably herein and refer to an amount of therapeutic compound, such as an antisense oligomer, administered to a mammalian subject, either as a single dose or as part of a series of doses, which is effective to produce a desired therapeutic effect. For an antisense oligomer, this effect is typically brought about by inhibiting translation or natural splice-processing of a selected target sequence, or producing a clinically meaningful amount of dystrophin (statistical significance).

In some embodiments, an effective amount is at least 10 mg/kg, or at least 20 mg/kg of a composition including an antisense oligomer for a period of time to treat the subject. In some embodiments, an effective amount is at least 20 mg/kg of a composition including an antisense oligomer to increase the number of dystrophin-positive fibers in a subject to at least 20% of normal. In certain embodiments, an effective amount is 10 mg/kg, or at least at least 20 mg/kg of a composition including an antisense oligomer to stabilize, maintain, or improve walking distance from a 20% deficit, for example in a 6 MWT, in a patient, relative to a healthy peer. In various embodiments, an effective amount is at least 10 mg/kg to about 30 mg/kg, at least 20 mg/kg to about 30 mg/kg, about 25 mg/kg to about 30 mg/kg, or about 30 mg/kg to about 50 mg/kg. In some embodiments, an effective amount is about 10 mg/kg, about 20 mg/kg, about 30 mg/kg, or about 50 mg/kg. In another aspect, an effective amount is at least about 10 mg/kg, about 20 mg/kg, about 25 mg/kg, about 30 mg/kg, or about 30 mg/kg to about 50 mg/kg, for at least 24 weeks, at least 36 weeks, or at least 48 weeks, to thereby increase the number of dystrophin-positive fibers in a subject to at least 20%, about 30%, about 40%, about 50%, about 60%, about 70%, about 80%, about 90%, about 95% of normal, and stabilize or improve walking distance from a 20% deficit, for example in a 6 MWT, in the patient relative to a healthy peer. In some embodiments, treatment increases the number of dystrophin-positive fibers to 20-60%, or 30-50% of normal in the patient.

By "enhance" or "enhancing," or "increase" or "increasing," or "stimulate" or "stimulating," refers generally to the ability of one or more antisense oligomers or antisense oligomer conjugates or pharmaceutical compositions of any of the foregoing to produce or cause a greater physiological response (i.e., downstream effects) in a cell or a subject, as compared to the response caused by either no antisense oligomer, no antisense oligomer conjugate, or a control compound. A greater physiological response may include increased expression of a functional form of a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%. The percentage of muscle fibers that express a functional dystrophin can also be measured, including increased dystrophin expression in about 1%, 2%, 5%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibers. For instance, it has been shown that around 40% of muscle function improvement can occur if 25-30% of fibers express dystrophin (see, e.g., DelloRusso et al, Proc Natl Acad Sci USA 99: 12979-12984, 2002). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times, including all integers and decimal points in between and above 1), e.g., 1.5, 1.6, 1.7, 1.8, etc.) the amount produced by the absence of an agent (no antisense oligomer or antisense oligomer conjugate) or a control compound.

As used herein, the terms "function" and "functional" and the like refer to a biological, enzymatic, or therapeutic function.

A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (see, e.g., Brown et al., Journal of Cell Science. 112:209-216, 1999). Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, Int J Exp Pathol 84: 165-172, 2003). These and other animal models can be used to measure the functional activity of various dystrophin proteins. Included are truncated forms of dystrophin, such as those forms that are produced following the administration of certain of the exon-skipping antisense oligomers or antisense oligomer conjugates of the present disclosure.

The terms "mismatch" or "mismatches" refer to one or more nucleobases (whether contiguous or separate) in an oligomer nucleobase sequence that are not matched to a target pre-mRNA according to base pairing rules. While perfect complementarity is often desired, some embodiments can include one or more but preferably 6, 5, 4, 3, 2, or 1 mismatches with respect to the target pre-mRNA. Variations at any location within the oligomer are included. In certain embodiments, antisense oligomers and antisense oligomer conjugates of the disclosure include variations in nucleobase sequence near the termini variations in the interior, and if present are typically within about 6, 5, 4, 3, 2, or 1 subunits of the 5' and/or 3' terminus.

Figure 2:
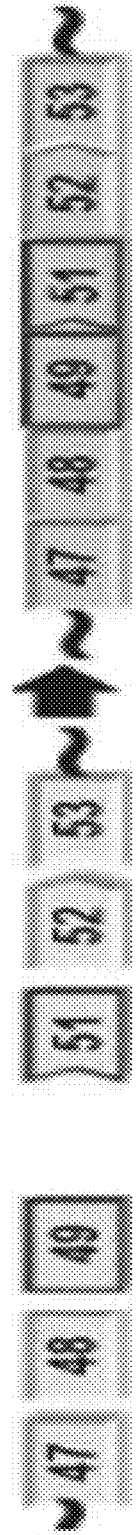
FIG. 2 depicts a section of abnormal dystrophin pre-mRNA (example of DMD) and resulting nonfunctional, unstable dystrophin.

The terms "morpholino," "morpholino oligomer," and "PMO" refer to a phosphorodiamidate morpholino oligomer of the following general structure:

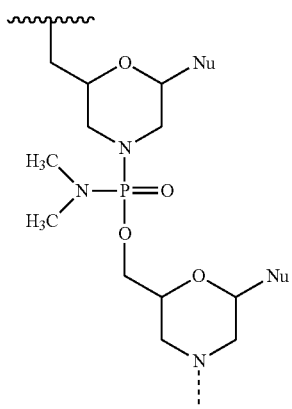

and as described in FIG. 2 of Summerton, J., et al., *Antisense & Nucleic Acid Drug Development*, 7: 187-195 (1997). Morpholinos as described herein include all stereoisomers and tautomers of the foregoing general structure. The synthesis, structures, and binding characteristics of morpholino oligomers are detailed in U.S. Pat. Nos. 5,698,685; 5,217,866; 5,142,047; 5,034,506; 5,166,315; 5,521,063; 5,506,337; 8,076,476; and 8,299,206; all of which are incorporated herein by reference.

In certain embodiments, a morpholino is conjugated at the 5' or 3' end of the oligomer with a "tail" moiety to increase its stability and/or solubility. Exemplary tails include:

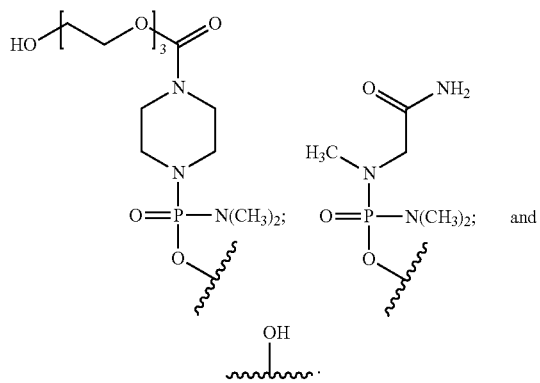

Of the above exemplary tail moieties, "TEG" or "EG3" refers to the following tail moiety:

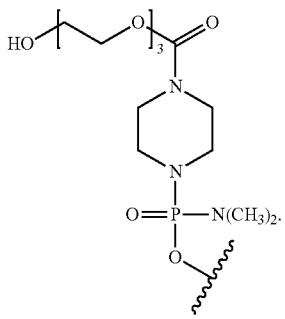

Of the above exemplary tail moieties, "GT" refers to the following tail moiety:

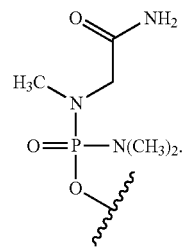

As used herein, the terms "-G-$R_6$" and "-G-$R_6$-Ac" are used interchangeably and refer to a peptide moiety conjugated to an antisense oligomer of the disclosure. In various embodiments, "G" represents a glycine residue conjugated to "$R_6$" by an amide bond, and each "R" represents an arginine residue conjugated together by amide bonds such that "$R_6$" means six (6) arginine residues conjugated together by amide bonds. The arginine residues can have any stereo configuration, for example, the arginine residues can be L-arginine residues, D-arginine residues, or a mixture of D- and L-arginine residues. In certain embodiments, "-G-R$_6$" or "-G-R$_6$-Ac" is conjugated to the morpholine ring nitrogen of the 3' most morpholino subunit of a PMO antisense oligomer of the disclosure. In some embodiments, "-G-R$_6$" or "-G-R$_6$-Ac" is conjugated to the 3' end of an antisense oligomer of the disclosure and is of the following formula:

Rana, R N A, 2003, 9, 1034-1048; Limbach et al. Nucleic Acids Research, 1994, 22, 2183-2196; and Revankar and Rao, Comprehensive Natural Products Chemistry, vol. 7, 313; are also contemplated, the contents of which are incorporated herein by reference.

Further examples of base pairing moieties include, but are not limited to, expanded-size nucleobases in which one or more benzene rings has been added. Nucleic acid base replacements described in: the Glen Research catalog

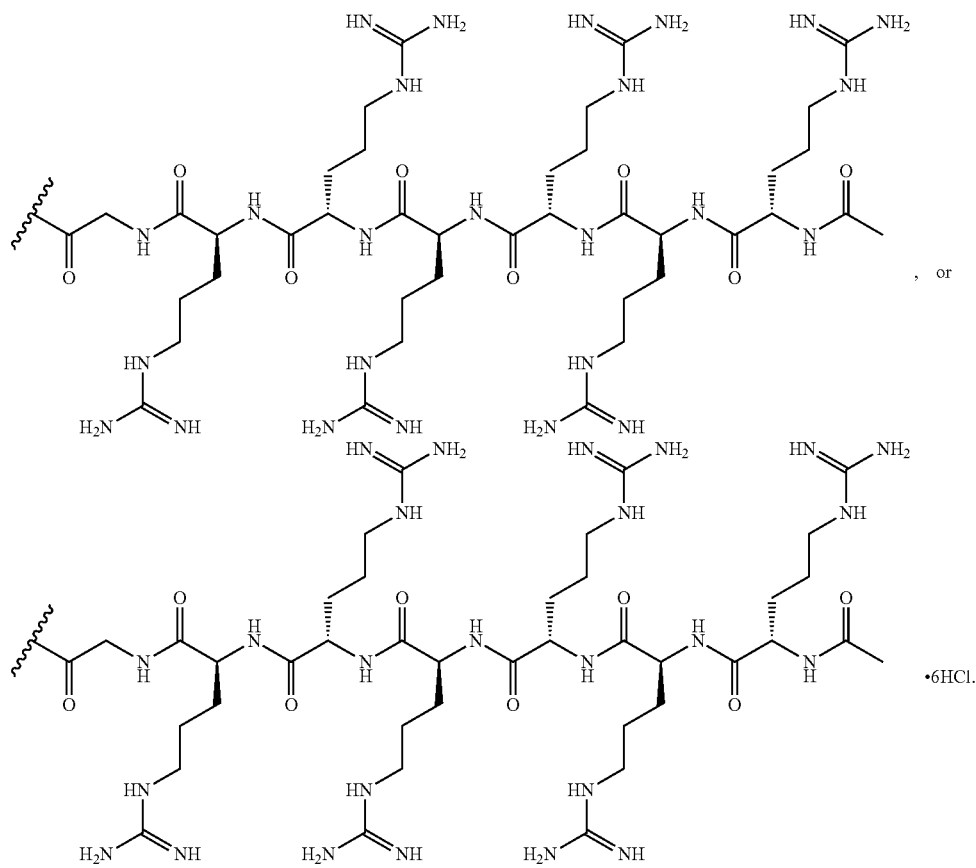

, or

•6HCl.

The terms "nucleobase" (Nu), "base pairing moiety" or "base" are used interchangeably to refer to a purine or pyrimidine base found in naturally occurring, or "native" DNA or RNA (e.g., uracil, thymine, adenine, cytosine, and guanine), as well as analogs of these naturally occurring purines and pyrimidines. These analogs may confer improved properties, such as binding affinity, to the oligomer. Exemplary analogs include hypoxanthine (the base component of inosine); 2,6-diaminopurine; 5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine (inosine) having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in: Chiu and (www.glenresearch.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; and Hirao, I., Curr. Opin. Chem. Biol., 2006, 10, 622-627; the contents of which are incorporated herein by reference, are contemplated as useful in the antisense oligomers and antisense oligomer conjugates described herein. Examples of expanded-size nucleobases include those shown below, as well as tautomeric forms thereof.

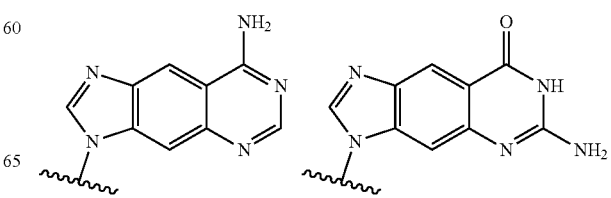

-continued

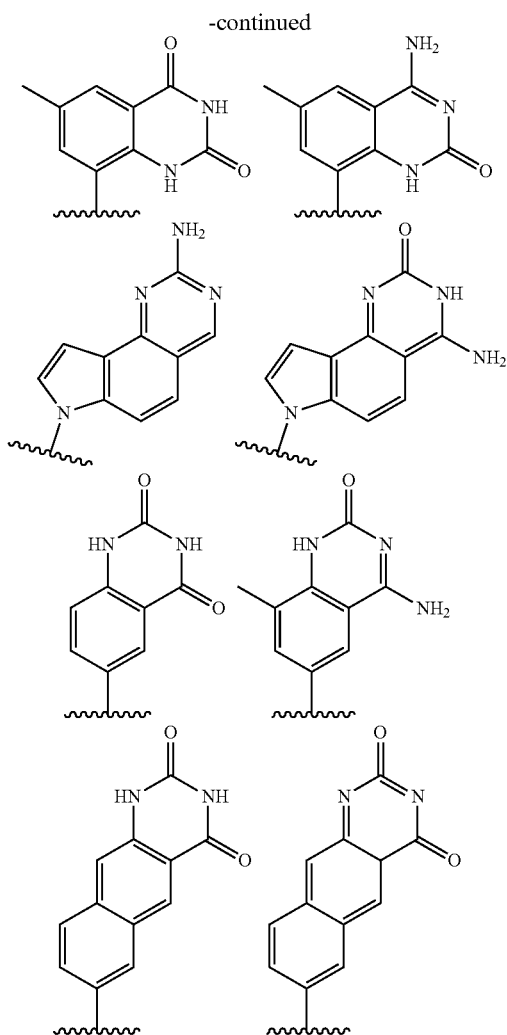

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For clarity, structures of the disclosure including, for example, Formula (IV), are continuous from 5' to 3', and, for the convenience of depicting the entire structure in a compact form, various illustration breaks labeled "BREAK A," "BREAK B," and "BREAK C" have been included. As would be understood by the skilled artisan, for example, each indication of "BREAK A" shows a continuation of the illustration of the structure at these points. The skilled artisan understands that the same is true for each instance of "BREAK B" and for "BREAK C" in the structures above. None of the illustration breaks, however, are intended to indicate, nor would the skilled artisan understand them to mean, an actual discontinuation of the structure above.

As used herein, a set of brackets used within a structural formula indicate that the structural feature between the brackets is repeated. In some embodiments, the brackets used can be "[" and "]," and in certain embodiments, brackets used to indicate repeating structural features can be "("and")." In some embodiments, the number of repeat iterations of the structural feature between the brackets is the number indicated outside the brackets such as 2, 3, 4, 5, 6, 7, and so forth. In various embodiments, the number of repeat iterations of the structural feature between the brackets is indicated by a variable indicated outside the brackets such as "Z".

As used herein, a straight bond or a squiggly bond drawn to a chiral carbon or phosphorous atom within a structural formula indicates that the stereochemistry of the chiral carbon or phosphorous is undefined and is intended to include all forms of the chiral center and/or mixtures thereof. Examples of such illustrations are depicted below.

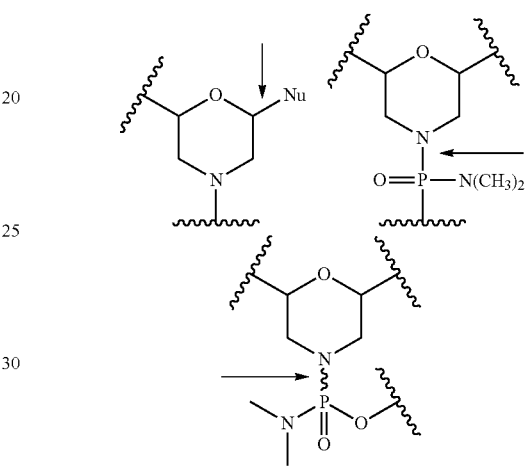

The phrase "pharmaceutically acceptable" means the substance or composition must be compatible, chemically and/or toxicologically, with the other ingredients comprising a formulation, and/or the subject being treated therewith.

The phrase "pharmaceutically-acceptable carrier" as used herein means a non-toxic, inert solid, semi-solid or liquid filler, diluent, encapsulating material, or formulation auxiliary of any type. Some examples of materials which can serve as pharmaceutically acceptable carriers are: sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening agents; flavoring agents; perfuming agents; preservatives; and antioxidants; according to the judgment of the formulator.

The term "restoration" with respect to dystrophin synthesis or production refers generally to the production of a dystrophin protein including truncated forms of dystrophin in a patient with muscular dystrophy following treatment with an antisense oligomer or antisense oligomer conjugate described herein. In some embodiments, treatment results in an increase in novel dystrophin production in a patient by 1%, 5%, 10%, 20%, 30%, 40%, 50%, 60%, 70%, 80%, 90%, or 100% (including all integers in between). In some embodiments, treatment increases the number of dystrophin-positive fibers to at least about 20%, about 30%, about 40%, about 50%, about 60%, about 70%, about 80%, about 90%, or about 95% to 100% of normal in the subject. In other embodiments, treatment increases the number of dystrophin-positive fibers to about 20% to about 60%, or about 30% to about 50%, of normal in the subject. The percent of dystrophin-positive fibers in a patient following treatment can be determined by a muscle biopsy using known techniques. For example, a muscle biopsy may be taken from a suitable muscle, such as the biceps brachii muscle in a patient.

Analysis of the percentage of positive dystrophin fibers may be performed pre-treatment and/or post-treatment or at time points throughout the course of treatment. In some embodiments, a post-treatment biopsy is taken from the contralateral muscle from the pre-treatment biopsy. Pre- and post-treatment dystrophin expression analysis may be performed using any suitable assay for dystrophin. In some embodiments, immunohistochemical detection is performed on tissue sections from the muscle biopsy using an antibody that is a marker for dystrophin, such as a monoclonal or a polyclonal antibody. For example, the MANDYS106 antibody can be used which is a highly sensitive marker for dystrophin. Any suitable secondary antibody may be used.

In some embodiments, the percent dystrophin-positive fibers are calculated by dividing the number of positive fibers by the total fibers counted. Normal muscle samples have 100% dystrophin-positive fibers. Therefore, the percent dystrophin-positive fibers can be expressed as a percentage of normal. To control for the presence of trace levels of dystrophin in the pretreatment muscle, as well as revertant fibers, a baseline can be set using sections of pre-treatment muscles from a patient when counting dystrophin-positive fibers in post-treatment muscles. This may be used as a threshold for counting dystrophin-positive fibers in sections of post-treatment muscle in that patient. In other embodiments, antibody-stained tissue sections can also be used for dystrophin quantification using Bioquant image analysis software (Bioquant Image Analysis Corporation, Nashville, Tenn.). The total dystrophin fluorescence signal intensity can be reported as a percentage of normal. In addition, Western blot analysis with monoclonal or polyclonal anti-dystrophin antibodies can be used to determine the percentage of dystrophin positive fibers. For example, the anti-dystrophin antibody NCL-Dys1 from Leica Biosystems may be used. The percentage of dystrophin-positive fibers can also be analyzed by determining the expression of the components of the sarcoglycan complex ($\beta,\gamma$) and/or neuronal NOS.

In some embodiments, treatment with an antisense oligomer or an antisense oligomer conjugate of the disclosure slows or reduces the progressive respiratory muscle dysfunction and/or failure in patients with DMD that would be expected without treatment. In some embodiments, treatment with an antisense oligomer or antisense oligomer conjugate of the disclosure may reduce or eliminate the need for ventilation assistance that would be expected without treatment. In some embodiments, measurements of respiratory function for tracking the course of the disease, as well as the evaluation of potential therapeutic interventions include maximum inspiratory pressure (MIP), maximum expiratory pressure (MEP), and forced vital capacity (FVC). MIP and MEP measure the level of pressure a person can generate during inhalation and exhalation, respectively, and are sensitive measures of respiratory muscle strength. MIP is a measure of diaphragm muscle weakness.

In some embodiments, MEP may decline before changes in other pulmonary function tests, including MIP and FVC. In certain embodiments, MEP may be an early indicator of respiratory dysfunction. In certain embodiments, FVC may be used to measure the total volume of air expelled during forced exhalation after maximum inspiration. In patients with DMD, FVC increases concomitantly with physical growth until the early teens. However, as growth slows or is stunted by disease progression, and muscle weakness progresses, the vital capacity enters a descending phase and declines at an average rate of about 8 to 8.5 percent per year after 10 to 12 years of age. In certain embodiments, MIP percent predicted (MIP adjusted for weight), MEP percent predicted (MEP adjusted for age), and FVC percent predicted (FVC adjusted for age and height) are supportive analyses.

The terms "subject" and "patient" as used herein include any animal that exhibits a symptom, or is at risk for exhibiting a symptom, which can be treated with an antisense oligomer or an antisense oligomer conjugate of the disclosure, such as a subject (or patient) that has or is at risk for having DMD or BMD, or any of the symptoms associated with these conditions (e.g., muscle fiber loss). Suitable subjects (or patients) include laboratory animals (such as mouse, rat, rabbit, or guinea pig), farm animals, and domestic animals or pets (such as a cat or dog). Non-human primates and, preferably, human patients (or subjects), are included. Also included are methods of producing dystrophin in a subject (or patient) having a mutation of the dystrophin gene that is amenable to exon 51 skipping.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phase "targeting sequence" refers to a sequence of nucleobases of an oligomer that is complementary to a sequence of nucleotides in a target pre-mRNA. In some embodiments of the disclosure, the sequence of nucleotides in the target pre-mRNA is an exon 52 annealing site in the dystrophin pre-mRNA designated as H52A(−01+24).

"Treatment" of a subject (e.g. a mammal, such as a human) or a cell is any type of intervention used in an attempt to alter the natural course of the subject or cell. Treatment includes, but is not limited to, administration of an oligomer or a pharmaceutical composition thereof, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

In some embodiments, treatment with an antisense oligomer or an antisense oligomer conjugate of the disclosure increases novel dystrophin production, delays disease progression, slows or reduces the loss of ambulation, reduces muscle inflammation, reduces muscle damage, improves muscle function, reduces loss of pulmonary function, and/or enhances muscle regeneration that than would be expected without treatment. In some embodiments, treatment maintains, delays, or slows disease progression. In some embodiments, treatment maintains ambulation or reduces the loss of ambulation. In some embodiments, treatment maintains pulmonary function or reduces loss of pulmonary function. In some embodiments, treatment maintains or increases a stable walking distance in a patient, as measured by, for example, the 6 Minute Walk Test (6MWT). In some embodiments, treatment maintains or reduces the time to walk/run 10 meters (i.e., the 10 meter walk/run test). In some embodiments, treatment maintains or reduces the time to stand from supine (i.e, time to stand test). In some embodiments, treatment maintains or reduces the time to climb four standard stairs (i.e., the four-stair climb test). In some embodiments, treatment maintains or reduces muscle inflammation in the patient, as measured by, for example, MRI (e.g., MRI of the leg muscles). In some embodiments, MM measures T2 and/or fat fraction to identify muscle degeneration. MRI can identify changes in muscle structure and composition caused by inflammation, edema, muscle damage, and fat infiltration.

In some embodiments, treatment with an antisense oligomer or an antisense oligomer conjugate of the disclosure increases novel dystrophin production and slows or reduces the loss of ambulation that would be expected without treatment. For example, treatment may stabilize, maintain, improve or increase walking ability (e.g., stabilization of ambulation) in the subject. In some embodiments, treatment maintains or increases a stable walking distance in a patient, as measured by, for example, the 6 Minute Walk Test (6MWT), described by McDonald, et al. (Muscle Nerve, 2010; 42:966-74, herein incorporated by reference). A change in the 6 Minute Walk Distance (6MWD) may be expressed as an absolute value, a percentage change or a change in the %-predicted value. In some embodiments, treatment maintains or improves a stable walking distance in a 6MWT from a 20% deficit in the subject relative to a healthy peer. The performance of a DMD patient in the 6MWT relative to the typical performance of a healthy peer can be determined by calculating a %-predicted value. For example, the %-predicted 6MWD may be calculated using the following equation for males: 196.72+(39.81×age)−(1.36×age$^2$)+(132.28×height in meters). For females, the %-predicted 6MWD may be calculated using the following equation: 188.61+(51.50×age)−(1.86×age$^2$)+(86.10×height in meters) (Henricson et al. PLoS Curr., 2012, version 2, herein incorporated by reference). In some embodiments, treatment with an antisense oligomer increases the stable walking distance in the patient from baseline to greater than 3, 5, 6, 7, 8, 9, 10, 15, 20, 25, 30, or 50 meters (including all integers in between).

Loss of muscle function in patients with DMD may occur against the background of normal childhood growth and development. Indeed, younger children with DMD may show an increase in distance walked during 6MWT over the course of about 1 year despite progressive muscular impairment. In some embodiments, the 6MWD from patients with DMD is compared to typically developing control subjects and to existing normative data from age and sex matched subjects. In some embodiments, normal growth and development can be accounted for using an age and height based equation fitted to normative data. Such an equation can be used to convert 6MWD to a percent-predicted (%-predicted) value in subjects with DMD. In certain embodiments, analysis of %-predicted 6MWD data represents a method to account for normal growth and development, and may show that gains in function at early ages (e.g., less than or equal to age 7) represent stable rather than improving abilities in patients with DMD (Henricson et al. PLoS Curr., 2012, version 2, herein incorporated by reference).

An antisense molecule nomenclature system was proposed and published to distinguish between the different antisense molecules (see Mann et al., (2002) J Gen Med 4, 644-654). This nomenclature became especially relevant when testing several slightly different antisense molecules, all directed at the same target region, as shown below:

H #A/D(x:y).

The first letter designates the species (e.g. H: human, M: murine, C: canine). "#" designates target dystrophin exon number. "A/D" indicates acceptor or donor splice site at the beginning and end of the exon, respectively. (x y) represents the annealing coordinates where "−" or "+" indicate intronic or exonic sequences respectively. For example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense molecule. Entirely exonic annealing coordinates that would be represented by A(+65+85), that is the site between the 65th and 85th nucleotide from the start of that exon.

II. Antisense Oligomers

A. Antisense Oligomers and Antisense Oligomer Conjugates Designed to Induce Exon 52 Skipping In certain embodiments, antisense oligomers and antisense oligomer conjugates of the disclosure are complementary to an exon 52 target region of the dystrophin gene and induce exon 52 skipping. In particular, the disclosure relates to antisense oligomers and antisense oligomer conjugates complementary to an exon 52 target region of the dystrophin pre-mRNA designated as an annealing site. In some embodiments, the annealing site is H52A(−01+24).

Antisense oligomers and antisense oligomer conjugates of the disclosure target dystrophin pre-mRNA and induces skipping of exon 52, so it is excluded or skipped from the mature, spliced mRNA transcript. By skipping exon 52, the disrupted reading frame is restored to an in-frame mutation. While DMD is comprised of various genetic subtypes, antisense oligomers and antisense oligomer conjugates of the disclosure were specifically designed to skip exon 52 of dystrophin pre-mRNA. DMD mutations amenable to skipping exon 52 comprise a subgroup of DMD patients (8%).

The nucleobase sequence of an antisense oligomer or an antisense oligomer conjugate that induces exon 52 skipping is designed to be complementary to a specific target sequence within exon 52 of dystrophin pre-mRNA. In some embodiments, an antisense oligomer or an antisense oligomer of the antisense oligomer conjugate is a PMO wherein each morpholino ring of the PMO is linked to a nucleobase including, for example, nucleobases found in DNA (adenine, cytosine, guanine, and thymine).

B. Oligomer Chemistry Features

The antisense oligomers and antisense oligomer conjugates of the disclosure can employ a variety of antisense oligomer chemistries. Examples of oligomer chemistries include, without limitation, morpholino oligomers, phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate subunits, 2'-O-[2-(N-methylcarbamoyl)ethyl] modified oligomers, including combinations of any of the foregoing. Phosphorothioate and 2'-O-Me-modified chemistries can be combined to generate a 2'O-Me-phosphorothioate backbone. See, e.g., PCT Publication Nos. WO/2013/112053 and WO/2009/008725, which are hereby incorporated by reference in their entireties. Exemplary embodiments of oligomer chemistries of the disclosure are further described below.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA is depicted below.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766; 7,211,668; 7,022,851; 7,125,994; 7,145,006; and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

2. Locked Nucleic Acids (LNAs)

Antisense oligomers and antisense oligomer conjugates may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Koshkin et al., Tetrahedron (1998) 54:3607; Jesper Wengel, Accounts of Chem. Research (1999) 32:301; Obika, et al., Tetrahedron Letters (1997) 38:8735; Obika, et al., Tetrahedron Letters (1998) 39:5401; and Obika, et al., Bioorganic Medicinal Chemistry (2008) 16:9230, which are hereby incorporated by reference in their entirety. A non-limiting example of an LNA is depicted below.

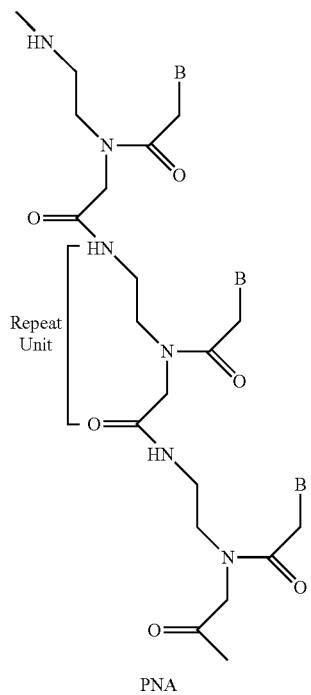

PNA

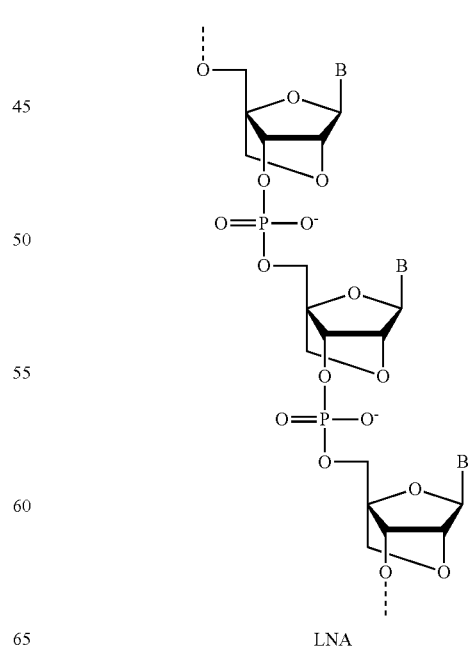

LNA

Antisense oligomers and antisense oligomer conjugates of the disclosure may incorporate one or more LNAs; in some cases, the antisense oligomers and antisense oligomer conjugates may be entirely composed of LNAs. Methods for the synthesis of individual LNA nucleoside subunits and their incorporation into oligomers are described, for example, in U.S. Pat. Nos. 7,572,582; 7,569,575; 7,084,125; 7,060,809; 7,053,207; 7,034,133; 6,794,499; and 6,670,461; each of which is incorporated by reference in its entirety. Typical intersubunit linkers include phosphodiester and phosphorothioate moieties; alternatively, non-phosphorous containing linkers may be employed. Further embodiments include an LNA containing antisense oligomer or antisense oligomer conjugate where each LNA subunit is separated by a DNA subunit. Certain antisense oligomers and antisense oligomer conjugates are composed of alternating LNA and DNA subunits where the intersubunit linker is phosphorothioate.

2'O,4'C-ethylene-bridged nucleic acids (ENAs) are another member of the class of BNAs. A non-limiting example is depicted below.

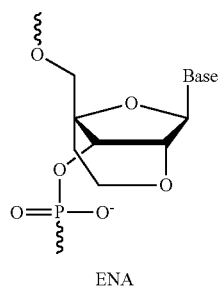

ENA

ENA oligomers and their preparation are described in Obika et al., *Tetrahedron Lett* (1997) 38 (50): 8735, which is hereby incorporated by reference in its entirety. Antisense oligomers and antisense oligomer conjugates of the disclosure may incorporate one or more ENA subunits.

3. Unlocked Nucleic Acid (UNA)

Antisense oligomers and antisense oligomer conjugates may also contain unlocked nucleic acid (UNA) subunits. UNAs and UNA oligomers are an analogue of RNA in which the C2'-C3' bond of the subunit has been cleaved. Whereas LNA is conformationally restricted (relative to DNA and RNA), UNA is very flexible. UNAs are disclosed, for example, in WO 2016/070166. A non-limiting example of an UNA is depicted below.

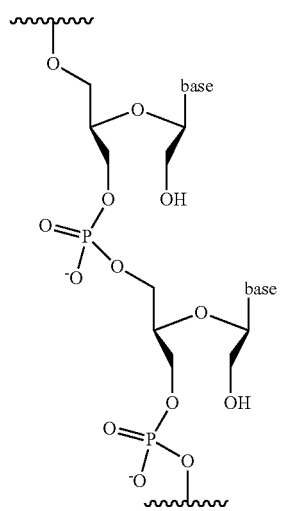

Typical intersubunit linkers include phosphodiester and phosphorothioate moieties; alternatively, non-phosphorous containing linkers may be employed.

4. Phosphorothioates

"Phosphorothioates" (or S-oligos) are a variant of normal DNA in which one of the nonbridging oxygens is replaced by a sulfur. A non-limiting example of a phosphorothioate is depicted below.

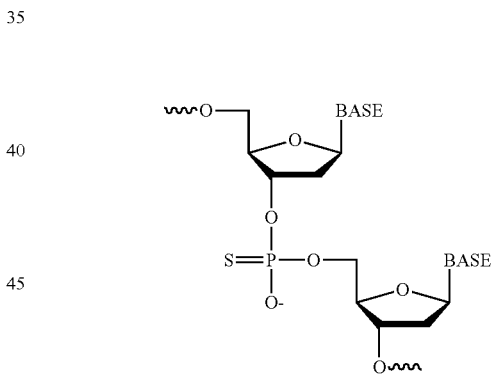

The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which is hereby incorporated by reference in its entirety). The latter methods avoid the problem of elemental sulfur's insolubility in most organic solvents and the toxicity of carbon disulfide. The TETD and BDTD methods also yield higher purity phosphorothioates.

5. Triclyclo-DNAs and Tricyclo-Phosphorothioate Subunits

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in International Patent Application Publication No. WO 2010/115993, which is hereby incorporated by reference in its entirety. Antisense oligomers and antisense oligomer conjugates of the disclosure may incorporate one or more tricycle-DNA subunits; in some cases, the antisense oligomers and antisense oligomer conjugates may be entirely composed of tricycle-DNA subunits.

Tricyclo-phosphorothioate subunits are tricyclo-DNA subunits with phosphorothioate intersubunit linkages. Tricyclo-phosphorothioate subunits and their synthesis are described in International Patent Application Publication No. WO 2013/053928, which is hereby incorporated by reference in its entirety. Antisense oligomers and antisense oligomer conjugates of the disclosure may incorporate one or more tricycle-DNA subunits; in some cases, the antisense oligomers and antisense oligomer conjugates may be entirely composed of tricycle-DNA subunits. A non-limiting example of a tricycle-DNA/tricycle-phophothioate subunit is depicted below.

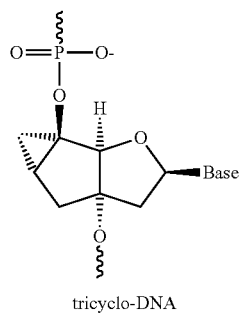

tricyclo-DNA

6. 2' 0-Methyl, 2' O-MOE, and 2'-F Oligomers

"2'-O-Me oligomer" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligomers (PTOs) for further stabilization. 2'O-Me oligomers (phosphodiester or phosphothioate) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer is depicted below.

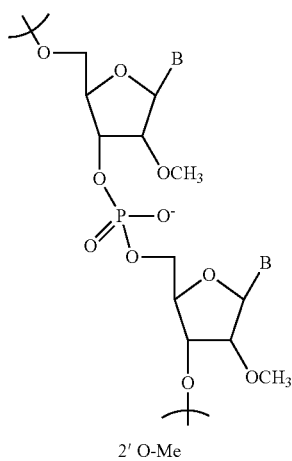

2' O-Me

2' O-Methoxyethyl Oligomers (2'-0 MOE) carry a methoxyethyl group at the 2'-OH residue of the ribose molecule and are discussed in Martin et al., Helv. Chim. Acta, 78, 486-504, 1995, which is hereby incorporated by reference in its entirety. A non-limiting example of a 2'O MOE subunit is depicted below.

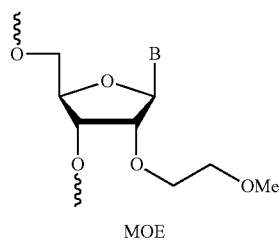

MOE

2'-Fluoro (2'-F) oligomers have a fluoro radical in at the 2' position in place of the 2'OH. A non-limiting example of a 2'-F oligomer is depicted below.

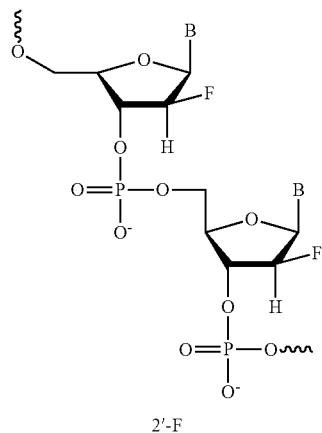

2'-F

2'-fluoro oligomers are further described in WO 2004/043977, which is hereby incorporated by reference in its entirety.

2'O-Methyl, 2'O-MOE, and 2'-F oligomers may also comprise one or more phosphorothioate (PS) linkages as depicted below.
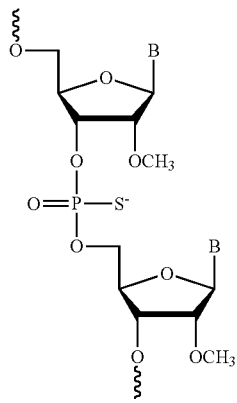
2'O-Methyl PS
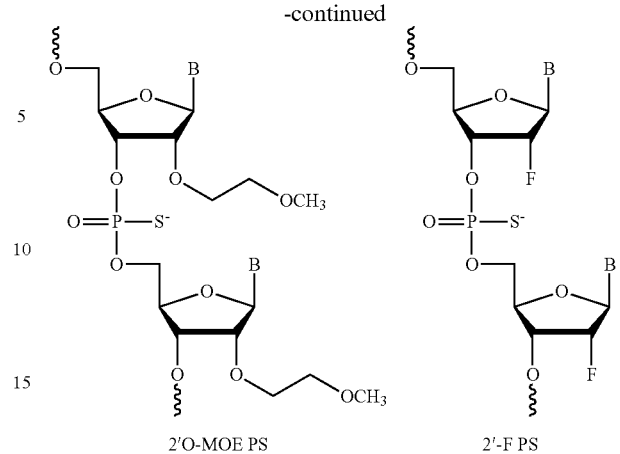
2'O-MOE PS
2'-F PS
Additionally, 2'O-Methyl, O-MOE, and 2'-F oligomers may comprise PS intersubunit linkages throughout the oligomer, for example, as in the 2'O-methyl PS oligomer drisapersen depicted below.
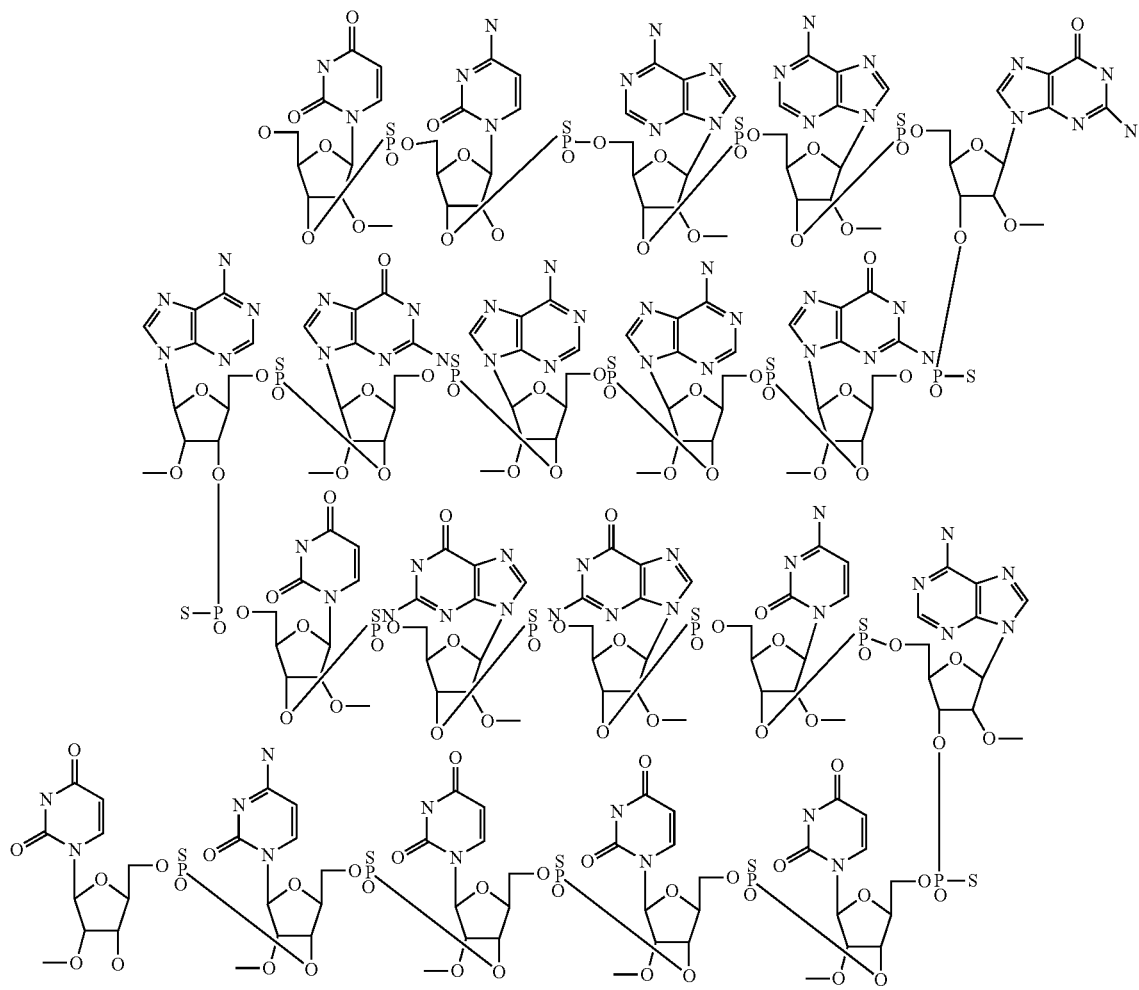

Alternatively, 2' O-Methyl, 2' O-MOE, and/or 2'-F oligomers may comprise PS linkages at the ends of the oligomer, as depicted below.

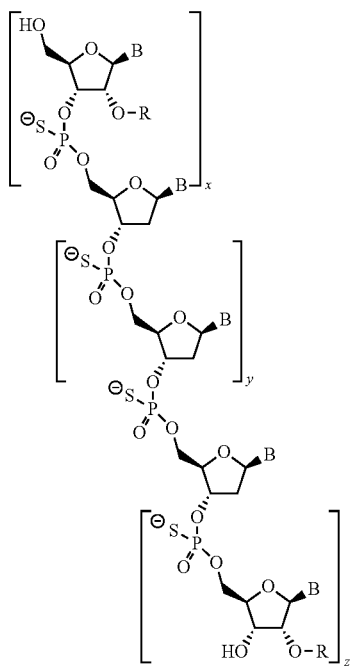

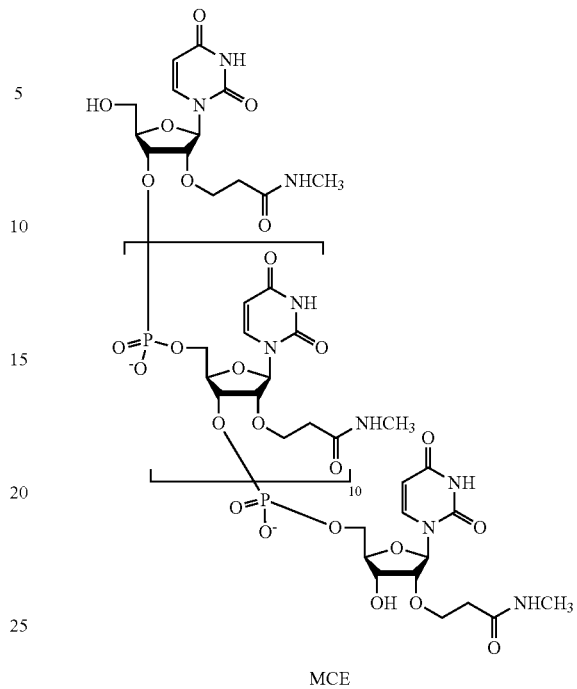

MCE

MCEs and their synthesis are described in Yamada et al., *J. Org. Chem.* (2011) 76(9):3042-53, which is hereby incorporated by reference in its entirety. Antisense oligomers and antisense oligomer conjugates of the disclosure may incorporate one or more MCE subunits.

where:

R is $CH_2CH_2OCH_3$ (methoxyethyl or MOE); and x, y, and z denote the number of nucleotides contained within each of the designated 5'-wing, central gap, and 3'-wing regions, respectively.

Antisense oligormers and antisense oligomer conjugates of the disclosure may incorporate one or more 2' O-Methyl, 2' O-MOE, and 2'-F subunits and may utilize any of the intersubunit linkages described here. In some instances, an antisense oligomer or and antisense oligomer conjugate of the disclosure may be composed of entirely 2'O-Methyl, 2' O-MOE, or 2-F subunits. One embodiment of an antisense oligomer or an antisense oligomer conjugate of the disclosure is composed entirely of 2'O-ethyl subunits.

7. 2'-O-[2-(N-methylcarbamoyl)ethyl] Oligomers (MCEs)

MCEs are another example of 2'O modified ribonucleosides useful in the antisense oligomers and antisense oligomer conjugates of the disclosure. Here, the 2'OH is derivatized to a 2-(N-methylcarbamoyl)ethyl moiety to increase nuclease resistance. A non-limiting example of an MCE oligomer is depicted below.

8. 2'-O-NMA Oligomers

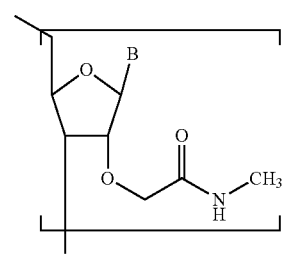

9. Stereo Specific Oligomers

Stereo specific oligomers are those in which the stereo chemistry of each phosphorous-containing linkage is fixed by the method of synthesis such that a substantially stereo-pure oligomer is produced. A non-limiting example of a stereo specific oligomer is depicted below.

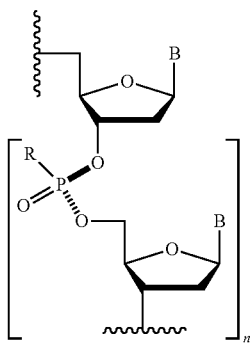

In the above example, each phosphorous of the oligomer has the same stereo configuration. Additional examples include the oligomers described above. For example, LNAs, ENAs, Tricyclo-DNAs, MCEs, 2' O-Methyl, 2' O-MOE, 2'-F, and morpholino-based oligomers can be prepared with stereo-specific phosphorous-containing internucleoside linkages such as, for example, phosphorothioate, phosphodiester, phosphoramidate, phosphorodiamidate, or other phosphorous-containing internucleoside linkages. Stereo specific oligomers, methods of preparation, chiral controlled synthesis, chiral design, and chiral auxiliaries for use in preparation of such oligomers are detailed, for example, in WO2017192664, WO2017192679, WO2017062862, WO2017015575, WO2017015555, WO2015107425, WO2015108048, WO2015108046, WO2015108047, WO2012039448, WO2010064146, WO2011034072, WO2014010250, WO2014012081, WO20130127858, and WO2011005761, each of which is hereby incorporated by reference in its entirety.

Figures 7C, 7D:
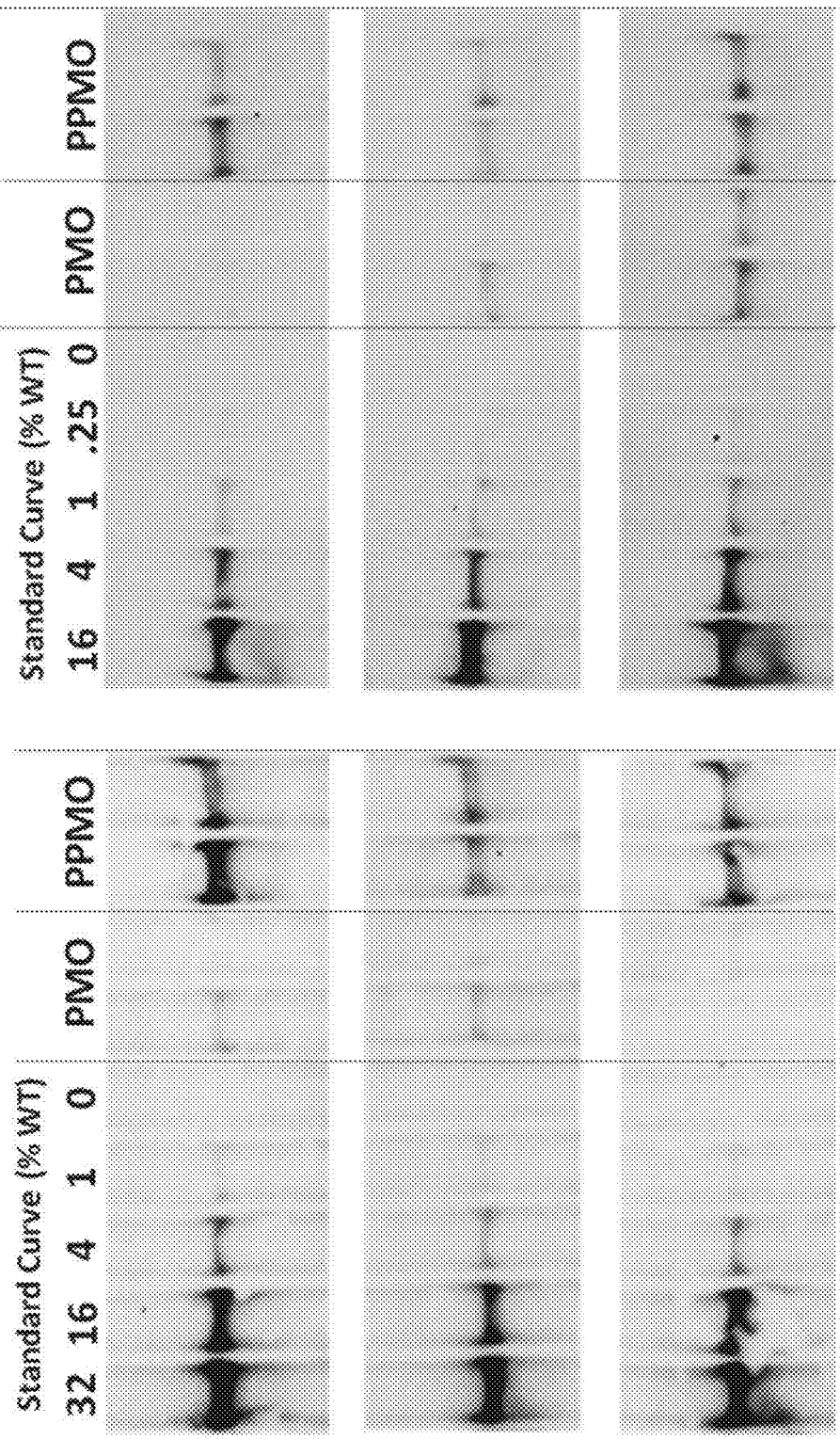
Figure 8A:
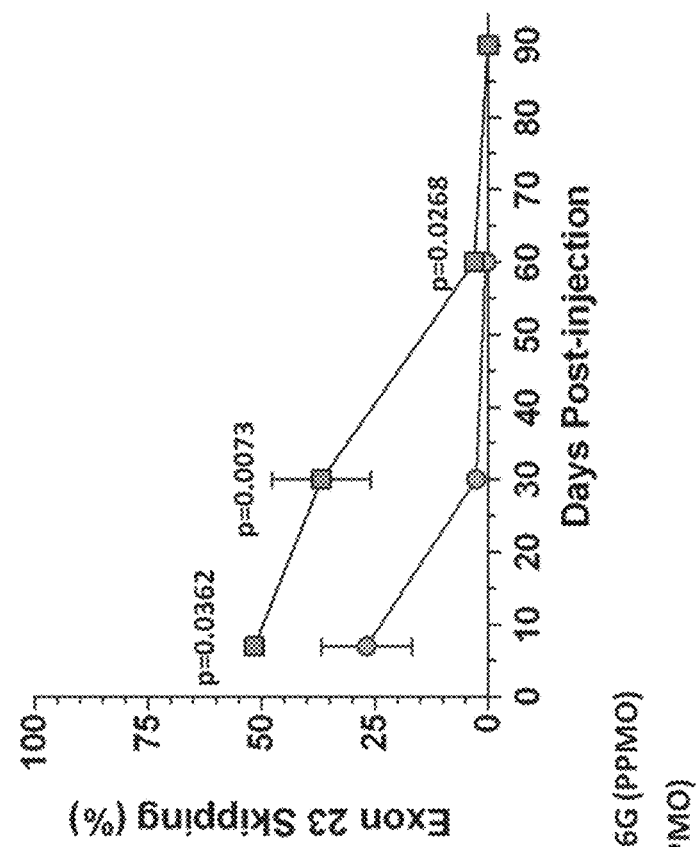
FIG. 8A provides a line graph depicting the percentage of wild-type dystrophin induced by PMO (PMO 4225) or PPMO (PPMO4225) in the diaphragm of mdx mice over 90 days post-injection, as determined by Western Blot analysis.
Figure 8B:
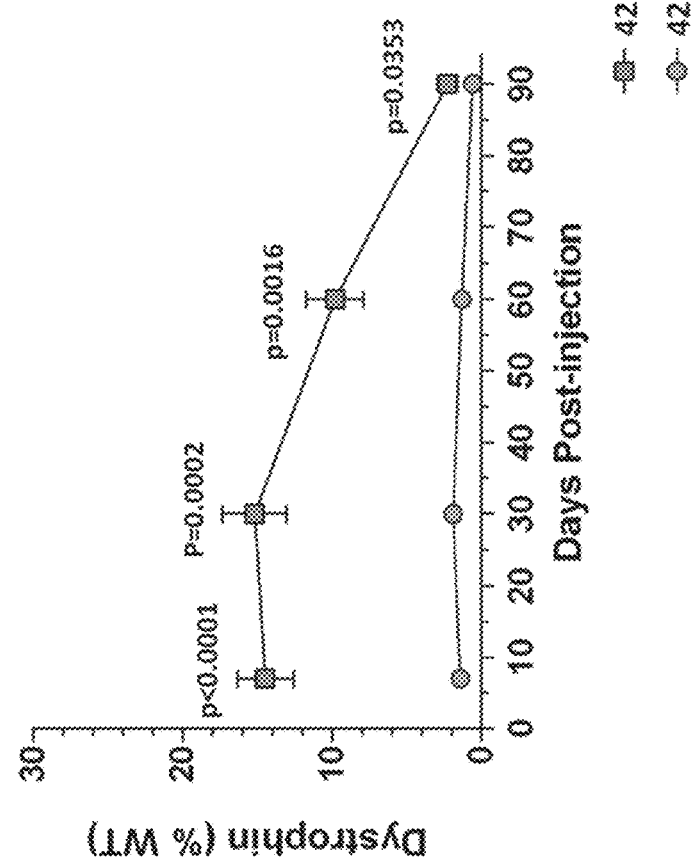
FIG. 8B provides a line graph depicting the percentage of exon 23 skipping induced by PMO (PMO 4225) or PPMO (PPMO4225) in the diaphragm of mdx mice over 90 days post-injection, as determined by RT-PCR.
Figure 9C:
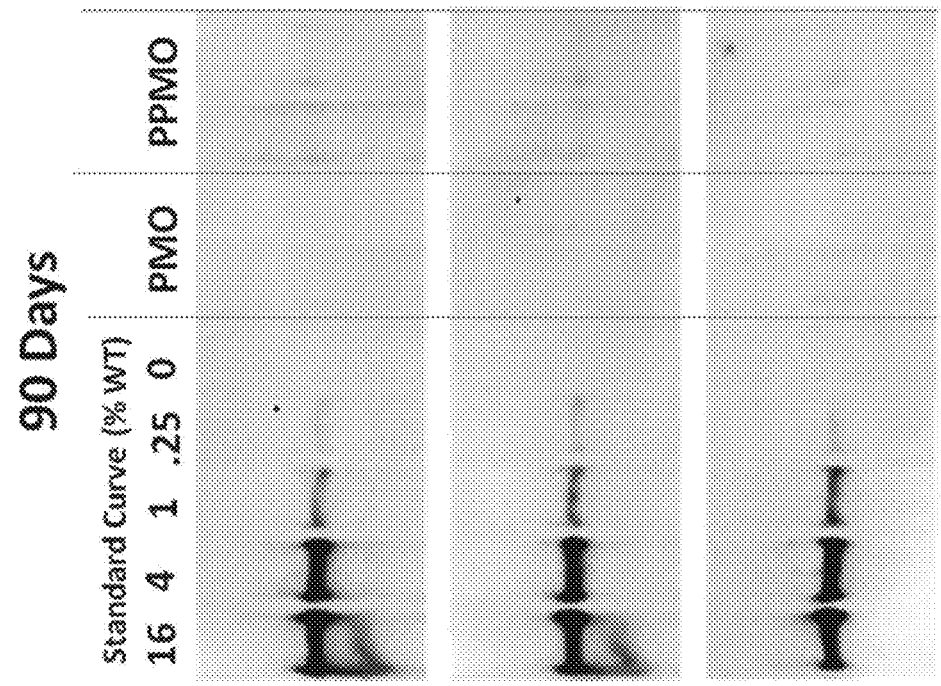
Figure 9D:
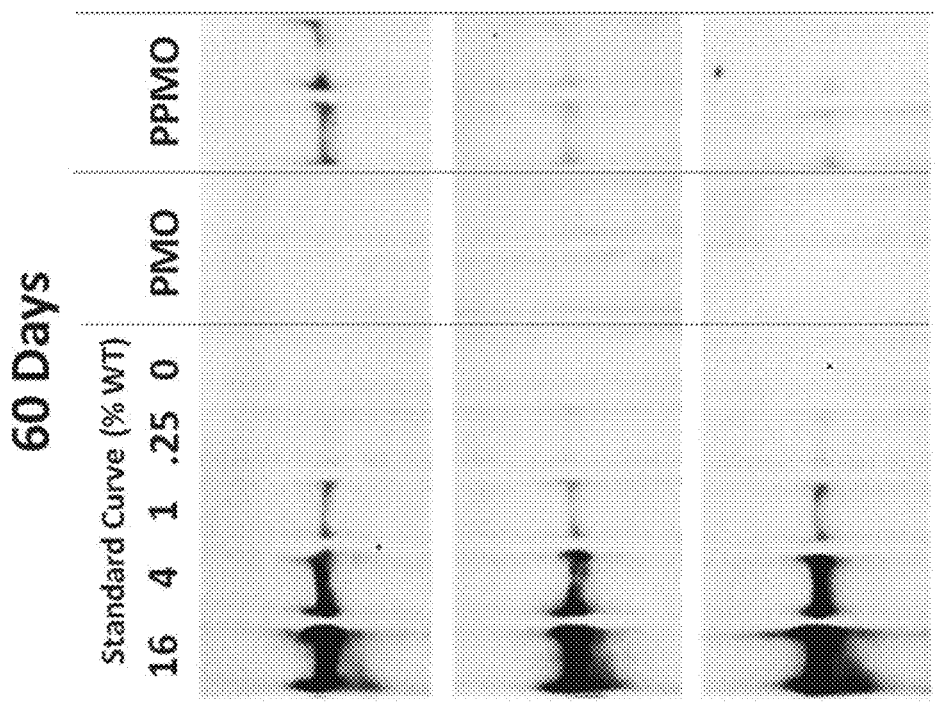
Figure 10B:
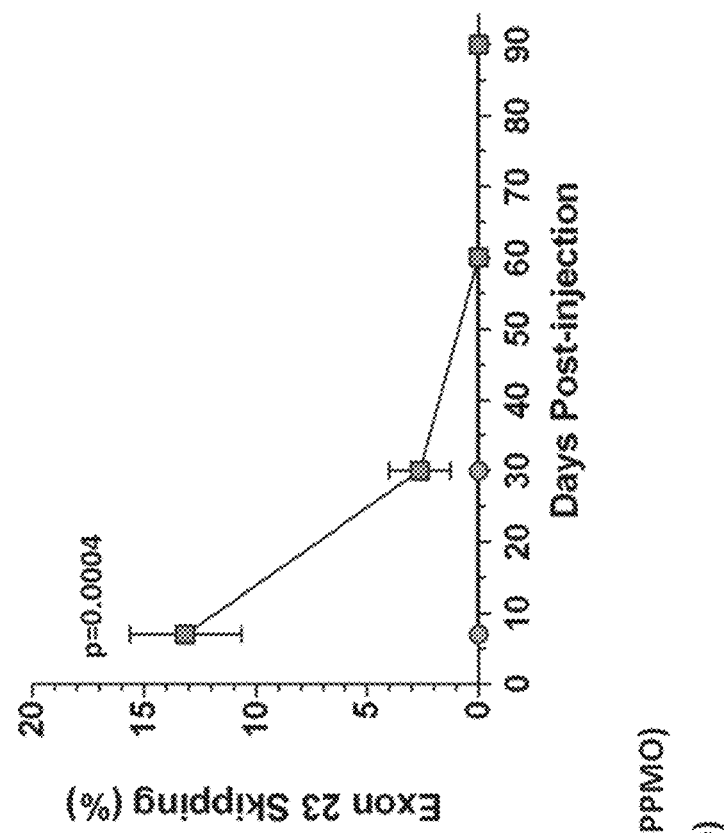
FIG. 10B provides a line graph depicting the percentage of exon 23 skipping induced by PMO (PMO 4225) or PPMO (PPMO4225) in the heart of mdx mice over 90 days post-injection, as determined by RT-PCR.
Figure 10A:
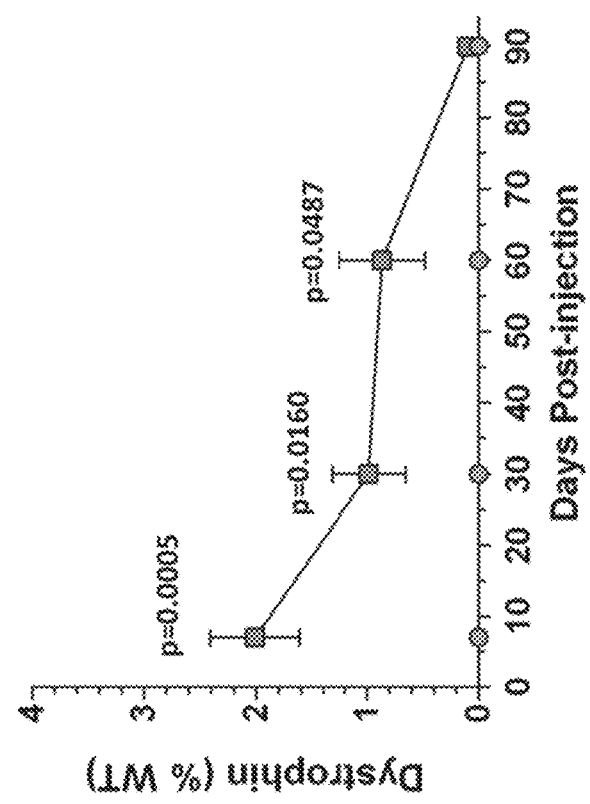
FIG. 10A provides a line graph depicting the percentage of wild-type dystrophin induced by PMO (PMO 4225) or PPMO (PPMO4225) in the heart of mdx mice over 90 days post-injection, as determined by Western Blot analysis.

Stereo specific oligomers can have phosphorous-containing internucleoside linkages in an $R_P$ or $S_P$ configuration. Chiral phosphorous-containing linkages in which the stereo configuration of the linkages is controlled is referred to as "stereopure," while chiral phosphorous-containing linkages in which the stereo configuration of the linkages is uncontrolled is referred to as "stereorandom." In certain embodiments, the oligomers of the disclosure comprise a plurality of stereopure and stereorandom linkages, such that the resulting oligomer has stereopure subunits at pre-specified positions of the oligomer. An example of the location of the stereopure subunits is provided in international patent application publication number WO 2017/062862 A2 in FIGS. 7A and 7B. In an embodiment, all the chiral phosphorous-containing linkages in an oligomer are stereorandom. In an embodiment, all the chiral phosphorous-containing linkages in an oligomer are stereopure.

In an embodiment of an oligomer with n chiral phosphorous-containing linkages (where n is an integer of 1 or greater), all n of the chiral phosphorous-containing linkages in the oligomer are stereorandom. In an embodiment of an oligomer with n chiral phosphorous-containing linkages (where n is an integer of 1 or greater), all n of the chiral phosphorous-containing linkages in the oligomer are stereopure. In an embodiment of an oligomer with n chiral phosphorous-containing linkages (where n is an integer of 1 or greater), at least 10% (to the nearest integer) of the n phosphorous-containing linkages in the oligomer are stereopure. In an embodiment of an oligomer with n chiral phosphorous-containing linkages (where n is an integer of 1 or greater), at least 20% (to the nearest integer) of the n phosphorous-containing linkages in the oligomer are stereopure. In an embodiment of an oligomer with n chiral phosphorous-containing linkages (where n is an integer of 1 or greater), at least 30% (to the nearest integer) of the n phosphorous-containing linkages in the oligomer are stereopure. In an embodiment of an oligomer with n chiral phosphorous-containing linkages (where n is an integer of 1 or greater), at least 40% (to the nearest integer) of the n phosphorous-containing linkages in the oligomer are stereopure. In an embodiment of an oligomer with n chiral phosphorous-containing linkages (where n is an integer of 1 or greater), at least 50% (to the nearest integer) of the n phosphorous-containing linkages in the oligomer are stereopure. In an embodiment of an oligomer with n chiral phosphorous-containing linkages (where n is an integer of 1 or greater), at least 60% (to the nearest integer) of the n phosphorous-containing linkages in the oligomer are stereopure. In an embodiment of an oligomer with n chiral phosphorous-containing linkages (where n is an integer of 1 or greater), at least 70% (to the nearest integer) of the n phosphorous-containing linkages in the oligomer are stereopure. In an embodiment of an oligomer with n chiral phosphorous-containing linkages (where n is an integer of 1 or greater), at least 80% (to the nearest integer) of the n phosphorous-containing linkages in the oligomer are stereopure. In an embodiment of an oligomer with n chiral phosphorous-containing linkages (where n is an integer of 1 or greater), at least 90% (to the nearest integer) of the n phosphorous-containing linkages in the oligomer are stereopure.

In an embodiment of an oligomer with n chiral phosphorous-containing linkages (where n is an integer of 1 or greater), the oligomer contains at least 2 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 3 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 4 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 5 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 6 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 7 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 8 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 9 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 10 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 11 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 12 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 13 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 14 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 15 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 16 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 17 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 18 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 19 contiguous stereopure phosphorous-containing linkages of the same stereo orientation (i.e. either $S_P$ or $R_P$). In an embodiment of an oligomer with n chiral phosphorous-containing linkages (where n is an integer of 1 or greater), the oligomer contains at least 20 contiguous stereopure phosphorous-containing linkages of the same stereo orientation (i.e. either $S_P$ or $R_P$).

9. Morpholino Oligomers

Exemplary embodiments of the disclosure relate to phosphorodiamidate morpholino oligomers of the following general structure:

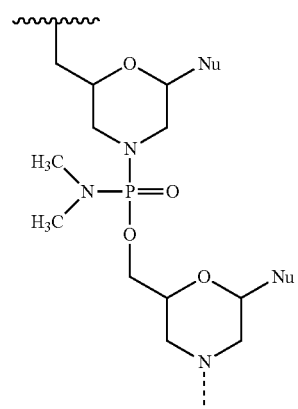

and as described in FIG. 2 of Summerton, J., et al., *Antisense & Nucleic Acid Drug Development*, 7: 187-195 (1997). Morpholinos as described herein are intended to cover all stereoisomers and tautomers of the foregoing general structure. The synthesis, structures, and binding characteristics of morpholino oligomers are detailed in U.S. Pat. Nos. 5,698,685; 5,217,866; 5,142,047; 5,034,506; 5,166,315; 5,521,063; 5,506,337; 8,076,476; and 8,299,206, all of which are incorporated herein by reference.

In certain embodiments, a morpholino is conjugated at the 5' or 3' end of the oligomer with a "tail" moiety to increase its stability and/or solubility. Exemplary tails include:

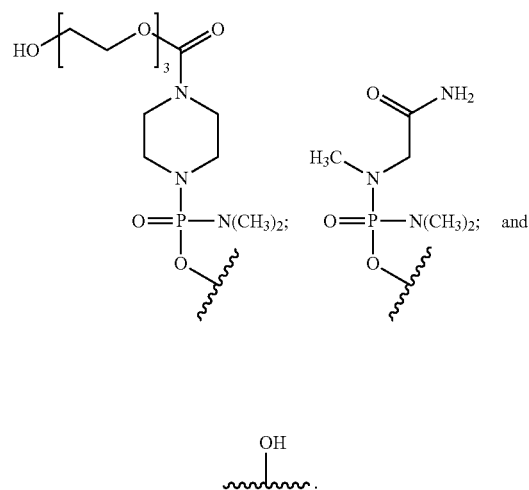

In various embodiments, an antisense oligomer conjugate of the disclosure is according to Formula (I):

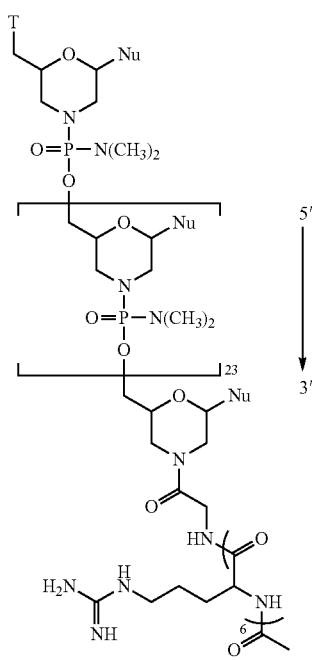

or a pharmaceutically acceptable salt thereof, wherein:

each Nu is a nucleobase which taken together form a targeting sequence;

T is a moiety selected from:

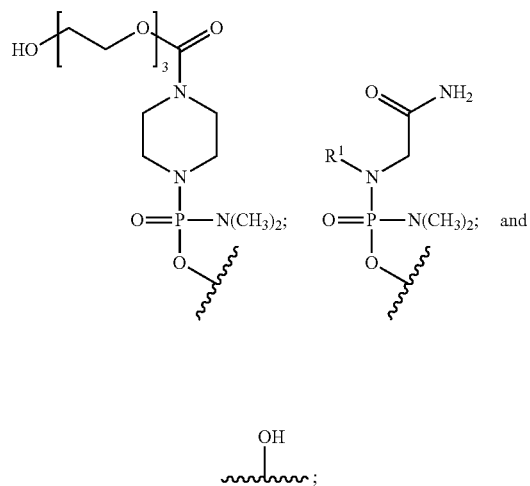

$R^1$ is $C_1$-$C_6$ alkyl;

wherein the targeting sequence is complementary to an exon 52 annealing site in the dystrophin pre-mRNA designated as H52A(−01+24).

In various embodiments, T is

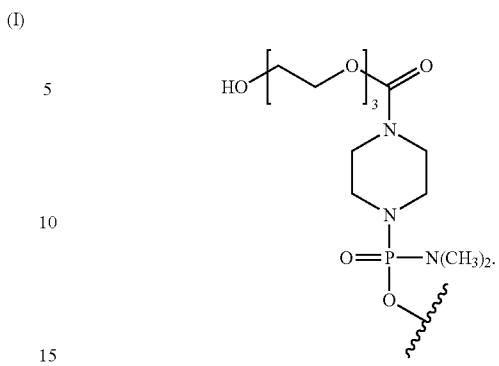

In various embodiments, $R^1$ is methyl, $CF_3$, $CCl_3$, $CFCl_2$, $CF_2Cl$, ethyl, $CH_2CF_3$, $CF_2CF_3$, propyl, isopropyl, butyl, isobutyl, sec-butyl, t-butyl, pentyl, isopentyl, neopentyl, hexyl, isohexyl, 3-methylpentyl, 2,2-dimethylbutyl, or 2,3-dimethylbutyl.

In some embodiments, an antisense oligomer conjugate of Formula (I) is an HCl (hydrochloric acid) salt thereof. In certain embodiments, the HCl salt is a 0.6HCl salt.

In some embodiments, each Nu is independently selected from cytosine (C), guanine (G), thymine (T), adenine (A), 5-methylcytosine (5mC), uracil (U), and hypoxanthine (I).

In some embodiments, the targeting sequence is SEQ ID NO: 1 (5'-CTGTTCCAAATCCTGCATTGTTGCC-3'), wherein each thymine (T) is optionally uracil (U).

In various embodiments, T is

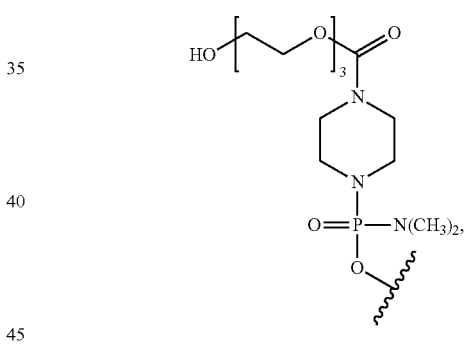

and the targeting sequence is SEQ ID NO: 1 (5'-CTGTTC-CAAATCCTGCATTGTTGCC-3'), wherein each thymine (T) is optionally uracil (U).

In various embodiments, T is

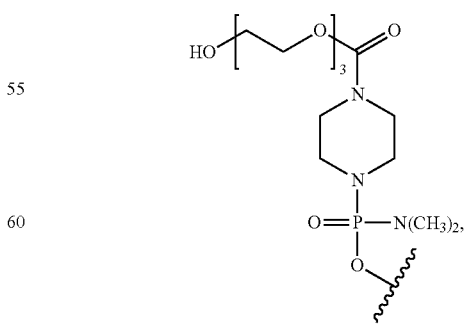

and the targeting sequence is SEQ ID NO: 1 (5'-CTGTTC-CAAATCCTGCATTGTTGCC-3').

In some embodiments, including, for example, some embodiments of Formula (I), an antisense oligomer conjugate of the disclosure is according to Formula (II):

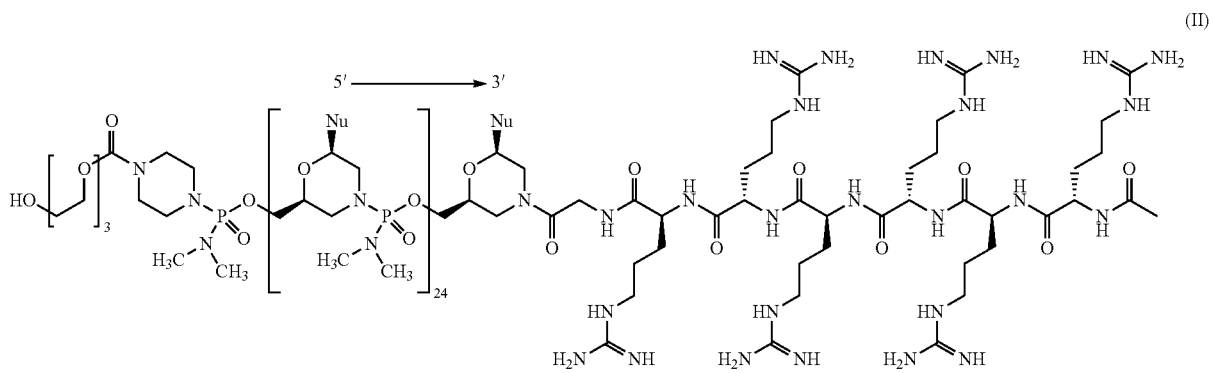

or a pharmaceutically acceptable salt thereof, wherein:

each Nu is a nucleobase which taken together form a targeting sequence that is complementary to an exon 52 annealing site in the dystrophin pre-mRNA designated as H52A(−01+24).

In some embodiments, each Nu is independently selected from cytosine (C), guanine (G), thymine (T), adenine (A), 5-methylcytosine (5mC), uracil (U), and hypoxanthine (I).

In various embodiments, each Nu from 1 to 25 and 5' to 3' is (SEQ ID NO: 1):

| Position No. 5' to 3' | Nu |
|---|---|
| 1 | C |
| 2 | X |
| 3 | G |
| 4 | X |
| 5 | X |
| 6 | C |
| 7 | C |
| 8 | A |
| 9 | A |
| 10 | A |
| 11 | X |
| 12 | C |
| 13 | C |
| 14 | X |
| 15 | G |
| 16 | C |
| 17 | A |
| 18 | X |
| 19 | X |
| 20 | G |
| 21 | X |
| 22 | X |
| 23 | G |
| 24 | C |
| 25 | C | wherein A is

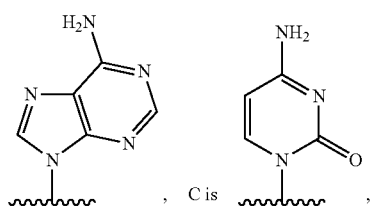

G is

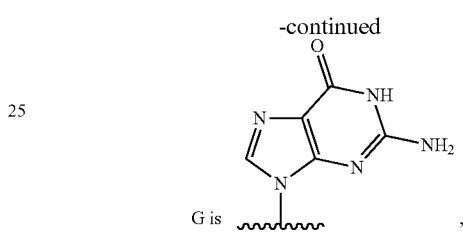

and X is

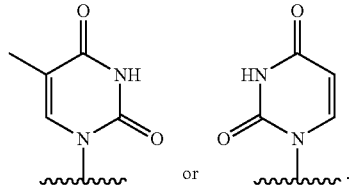

In certain embodiments, each X is independently

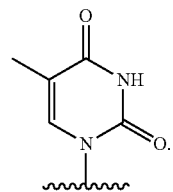 [SMILES: *n1cc(C)c(=O)[nH]c1=O]

In Some embodiments, an antisense oligomer conjugate of Formula (II) is an HCl (hydrochloric acid) salt thereof. In certain embodiments, the HCl salt is a 0.6HCl salt.

In some embodiments, including, for example, some embodiments of Formula (II), an antisense oligomer conjugate of the disclosure is according to Formula (IIA):

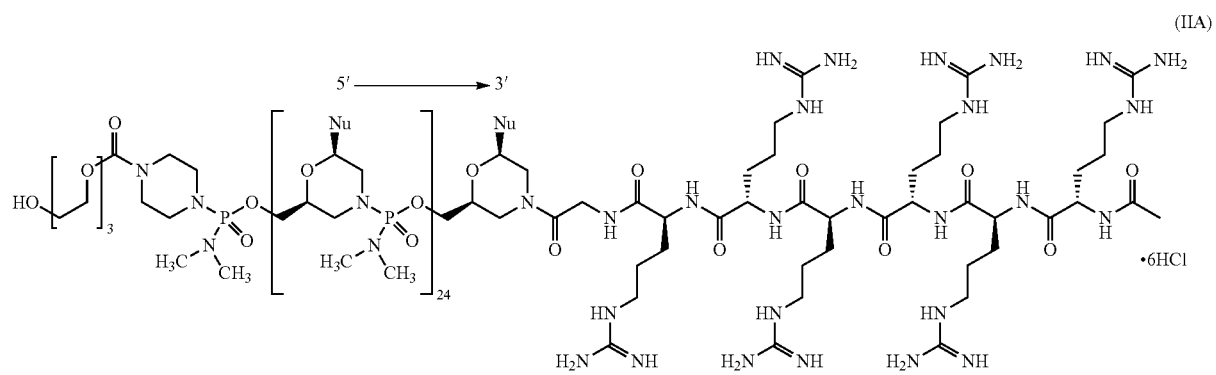

(IIA)

wherein each Nu is a nucleobase which taken together form a targeting sequence that is complementary to an exon 52 annealing site in the dystrophin pre-mRNA designated as H52A(−01+24).

In some embodiments, each Nu is independently selected from cytosine (C), guanine (G), thymine (T), adenine (A), 5-methylcytosine (5mC), uracil (U), and hypoxanthine (I).

In various embodiments, each Nu from 1 to 25 and 5' to 3' is (SEQ ID NO: 1):

| Position No. 5' to 3' | Nu |
|---|---|
| 1 | C |
| 2 | X |
| 3 | G |
| 4 | X |
| 5 | X |
| 6 | C |
| 7 | C |
| 8 | A |
| 9 | A |
| 10 | A |
| 11 | X |
| 12 | C |
| 13 | C |
| 14 | X |
| 15 | G |
| 16 | C |
| 17 | A |
| 18 | X |
| 19 | X |
| 20 | G |
| 21 | X |
| 22 | X |
| 23 | G |
| 24 | C |
| 25 | C | wherein A is

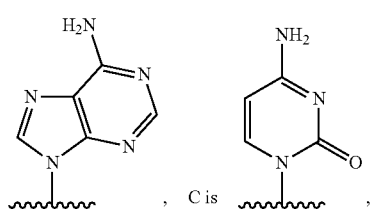 [SMILES: *n1cnc2c(N)ncnc21 ; *n1ccc(N)nc1=O]

G is

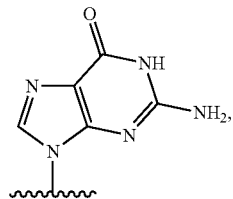 [SMILES: *n1cnc2c(=O)[nH]c(N)nc21]

and X is (two structures shown: 5-methyluracil (thymine) or uracil)

In certain embodiments, each X is (thymine structure)

In some embodiments including, for example, embodiments of antisense oligomer conjugates of Formula (II) and Formula (IIA), the targeting sequence is SEQ ID NO: 1 (5'-CTGTTCCAAATCCTGCATTGTTGCC-3') wherein each thymine (T) is optionally uracil (U). In various embodiments including, for example, embodiments of antisense oligomer conjugates of Formula (II) and Formula (IIA), the targeting sequence is SEQ ID NO: 1 (5'-CTGTTCCAAATCCTGCATTGTTGCC-3').

In some embodiments, including, for example, embodiments of antisense oligomer conjugates of Formula (I), an antisense oligomer conjugate of the disclosure is according to Formula (III):

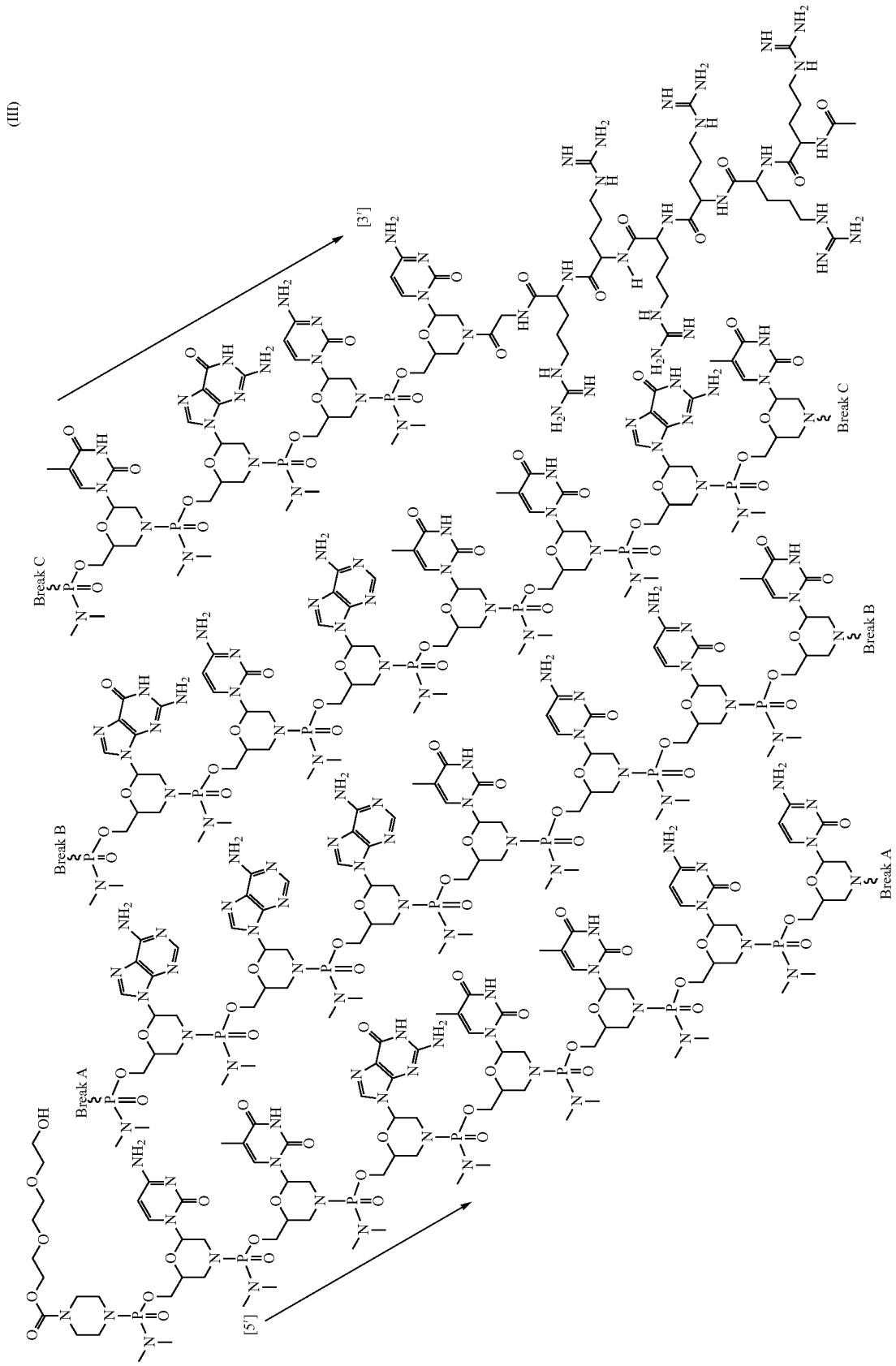

or a pharmaceutically acceptable salt thereof.

In some embodiments, an antisense oligomer conjugate of Formula (III) is an HCl (hydrochloric acid) salt thereof. In certain embodiments, the HCl salt is a 0.6HCl salt.

In some embodiments, including, for example, embodiments of antisense oligomer conjugates of Formula (III), an antisense oligomer conjugate of the disclosure is according to Formula (IIIA):

(IIIA)
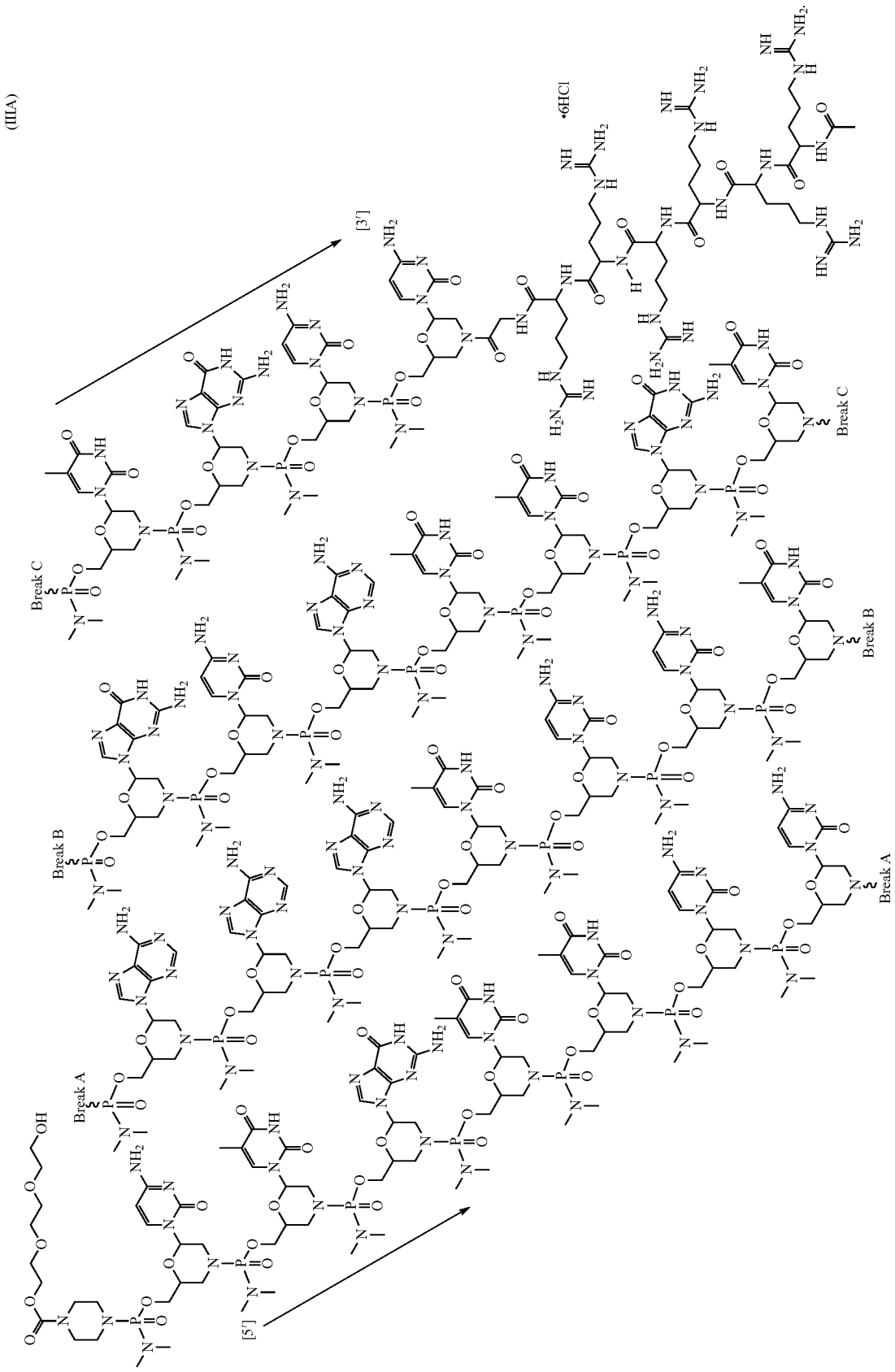

In some embodiments of the disclosure, including some embodiments of antisense oligomer conjugates of Formula (I) and embodiments of antisense oligomer conjugates of Formula (III), the antisense oligomer conjugate is according to Formula (IV):

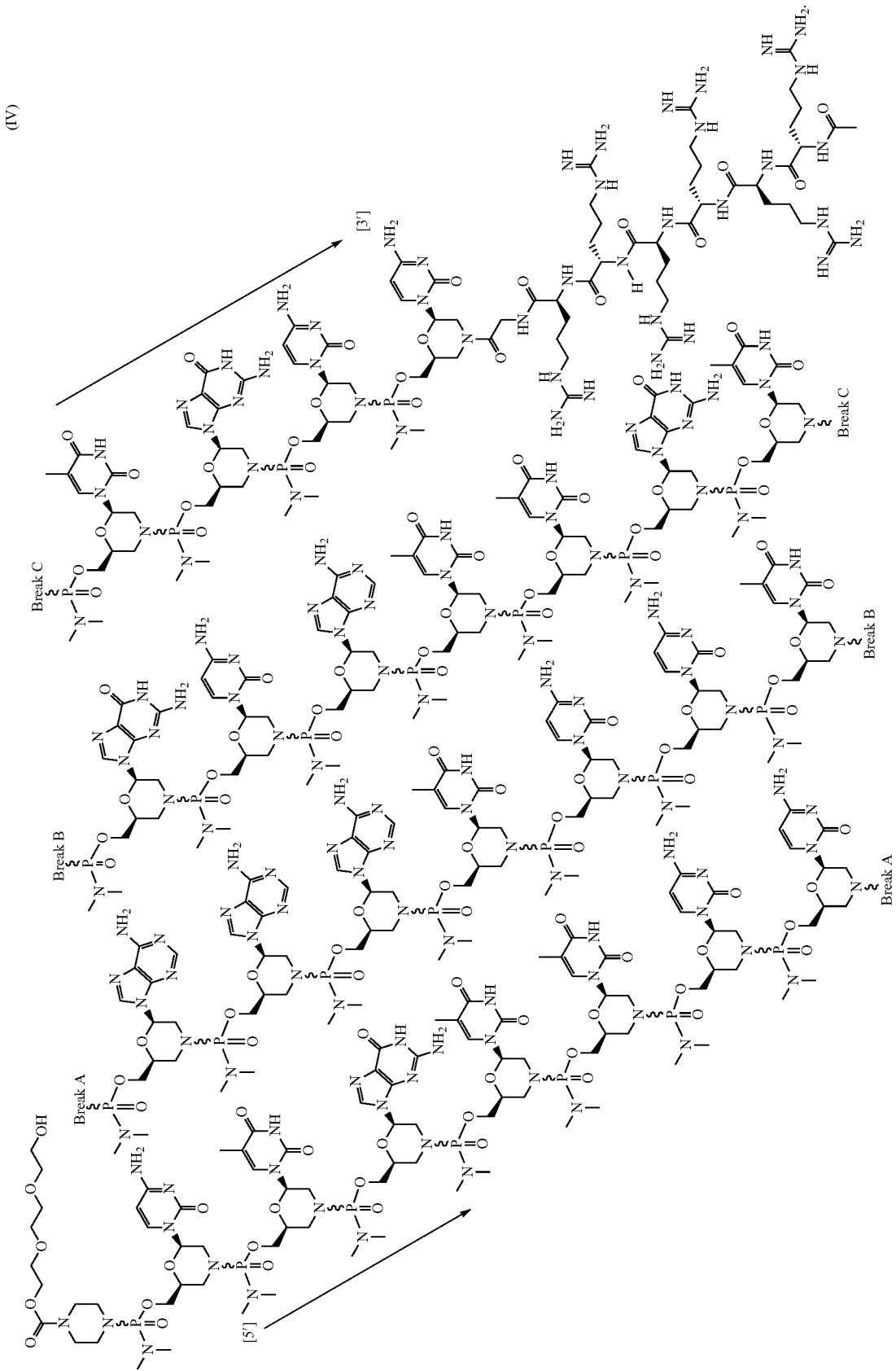

or a pharmaceutically acceptable salt thereof.

In some embodiments, an antisense oligomer conjugate of Formula (IV) is an HCl (hydrochloric acid) salt thereof. In certain embodiments, the HCl salt is a 0.6HCl salt.

In some embodiments, including, for example, embodiments of antisense oligomer conjugates of Formula (IV), an antisense oligomer conjugate of the disclosure is according to Formula (IVA):

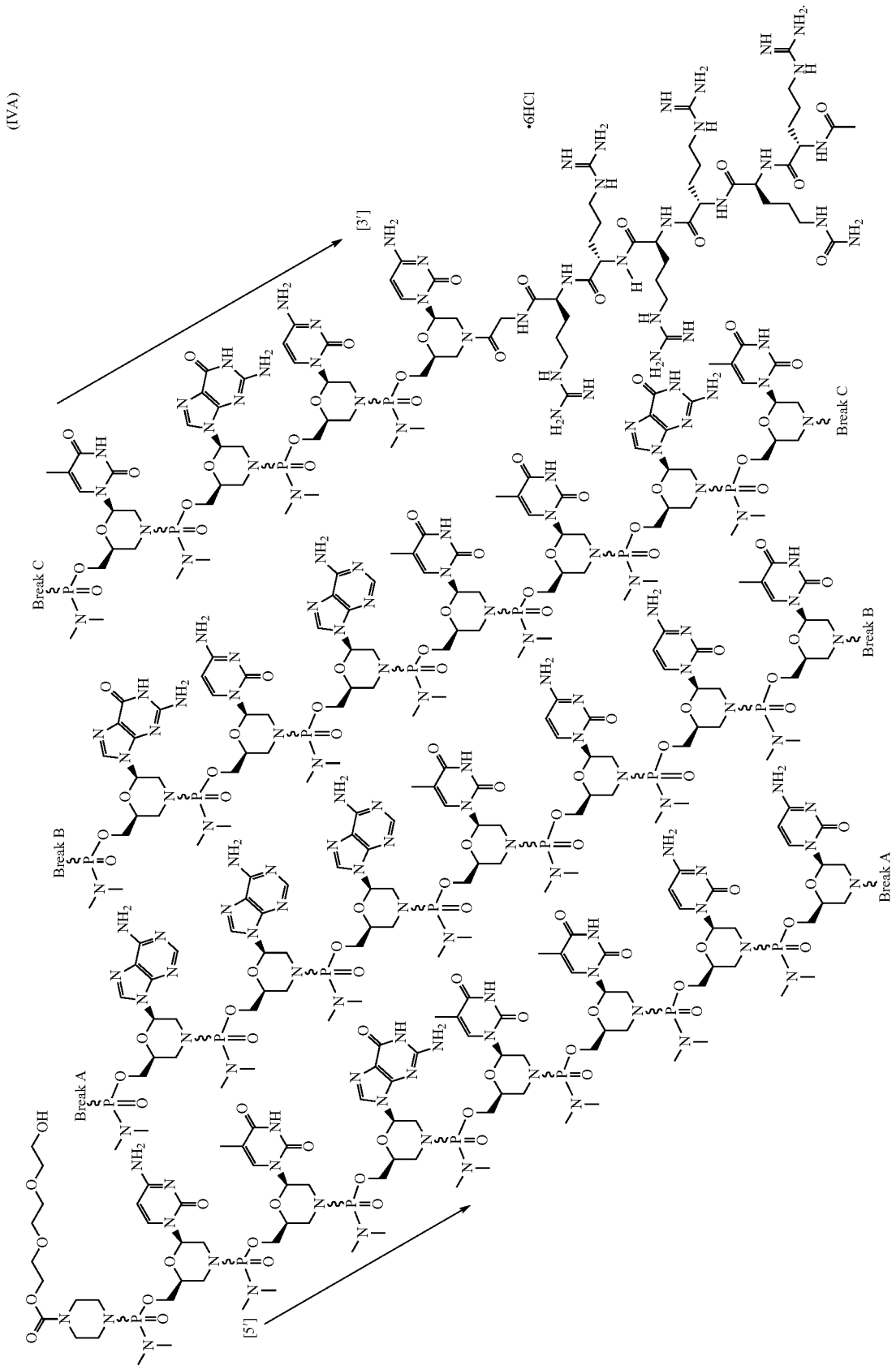

In various embodiments, an antisense oligomer of the disclosure is according to Formula (V):

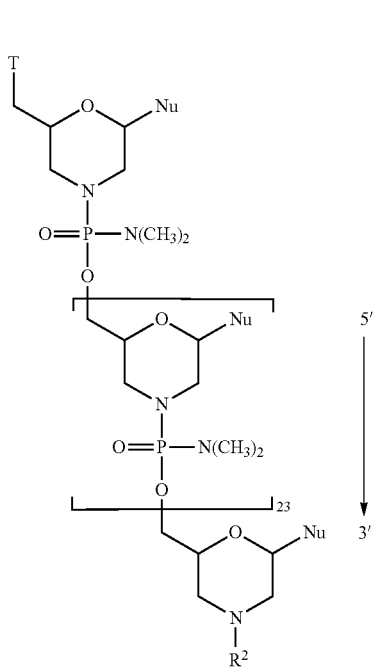

(V)

or a pharmaceutically acceptable salt thereof, wherein:

each Nu is a nucleobase which taken together form a targeting sequence;

T is a moiety selected from:

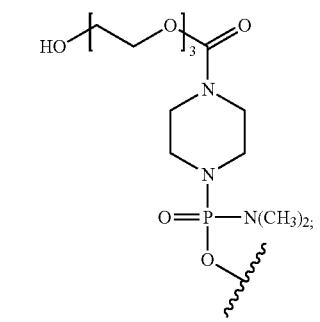

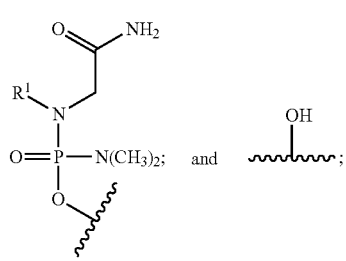

$R^1$ is $C_1$-$C_6$ alkyl; and $R^2$ is selected from H or acetyl, wherein the targeting sequence is complementary to an exon 52 annealing site in the dystrophin pre-mRNA designated as H52A(−01+24).

In various embodiments, T is

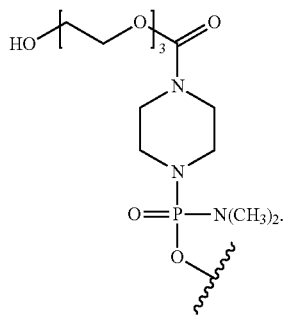

In various embodiments, $R^1$ is methyl, $CF_3$, $CCl_3$, $CFCl_2$, $CF_2Cl$, ethyl, $CH_2CF_3$, $CF_2CF_3$, propyl, isopropyl, butyl, isobutyl, sec-butyl, t-butyl, pentyl, isopentyl, neopentyl, hexyl, isohexyl, 3-methylpentyl, 2,2-dimethylbutyl, or 2,3-dimethylbutyl.

In some embodiments, each Nu is independently selected from cytosine (C), guanine (G), thymine (T), adenine (A), 5-methylcytosine (5mC), uracil (U), and hypoxanthine (I).

In some embodiments, the targeting sequence is SEQ ID NO: 1 (5'-CTGTTCCAAATCCTGCATTGTTGCC-3'), wherein each thymine (T) is optionally uracil (U).

In various embodiments, T is

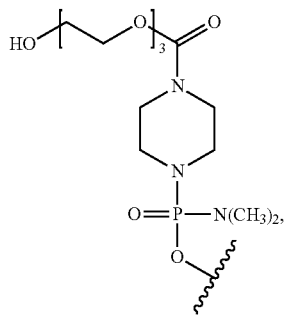

and the targeting sequence is SEQ ID NO: 1 (5'-CTGTTC-CAAATCCTGCATTGTTGCC-3'), wherein each thymine (T) is optionally uracil (U).

In various embodiments, T is

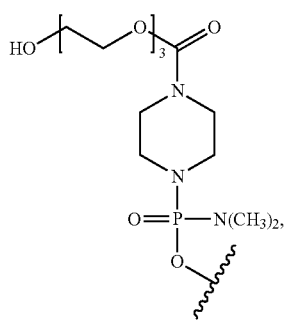

and the targeting sequence is SEQ ID NO: 1 (5'-CTGTTC-CAAATCCTGCATTGTTGCC-3').

In some embodiments, including, for example, some embodiments of Formula (IV), an antisense oligomer of the disclosure is according to Formula (V):

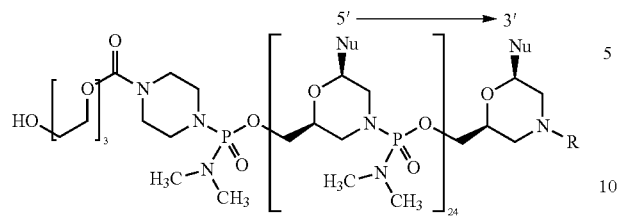

(VI)

or a pharmaceutically acceptable salt thereof, wherein:

R is selected from H or acetyl; and each Nu is a nucleobase which taken together form a targeting sequence that is complementary to an exon 53 annealing site in the dystrophin pre-mRNA designated as H52A(−01+24).

In some embodiments, R is H. In various embodiments, R is acetyl.

In some embodiments, each Nu is independently selected from cytosine (C), guanine (G), thymine (T), adenine (A), 5-methylcytosine (5mC), uracil (U), and hypoxanthine (I).

In various embodiments, each Nu from 1 to 25 and 5' to 3' is (SEQ ID NO: 1):

| Position No. 5' to 3' | Nu |
| --- | --- |
| 1 | C |
| 2 | X |
| 3 | G |
| 4 | X |
| 5 | X |
| 6 | C |
| 7 | C |
| 8 | A |
| 9 | A |
| 10 | A |
| 11 | X |
| 12 | C |
| 13 | C |
| 14 | X |
| 15 | G |
| 16 | C |
| 17 | A |
| 18 | X |
| 19 | X |
| 20 | G |
| 21 | X |
| 22 | X |
| 23 | G |
| 24 | C |
| 25 | C | wherein A is

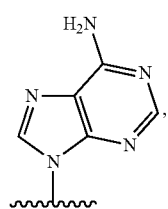 [SMILES: *n1cnc2c(N)ncnc21]

C is

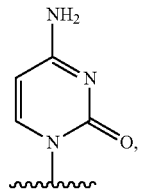 [SMILES: *n1ccc(N)nc1=O]

G is

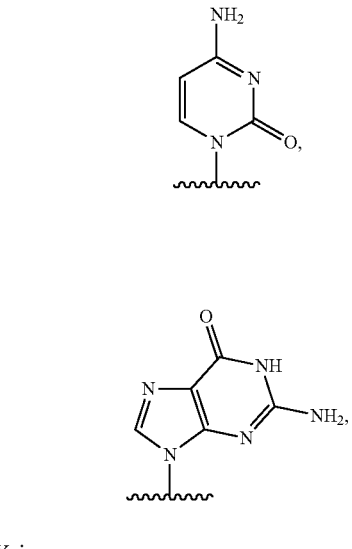

and X is

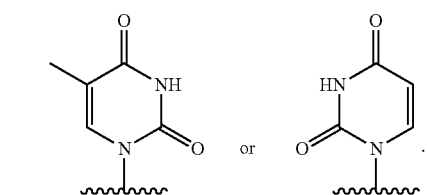

In certain embodiments, each X is independently

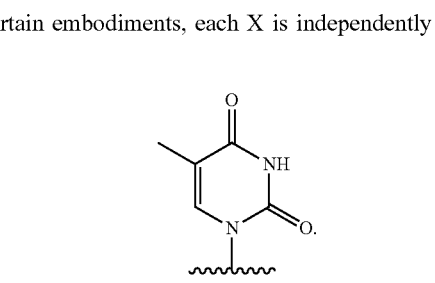

In various embodiments, R is H and each Nu from 1 to 25 and 5' to 3' is (SEQ ID NO: 1):

| Position No. 5' to 3' | Nu |
| --- | --- |
| 1 | C |
| 2 | X |
| 3 | G |
| 4 | X |
| 5 | X |
| 6 | C |
| 7 | C |
| 8 | A |
| 9 | A |
| 10 | A |
| 11 | X |
| 12 | C |
| 13 | C |
| 14 | X |
| 15 | G |
| 16 | C |

-continued
| Position No. 5' to 3' | Nu |
|---|---|
| 17 | A |
| 18 | X |
| 19 | X |
| 20 | G |
| 21 | X |
| 22 | X |
| 23 | G |
| 24 | C |
| 25 | C |
wherein A is
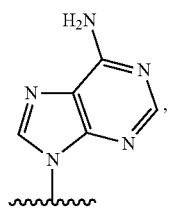 [SMILES: *n1cnc2c(N)ncnc21]
C is
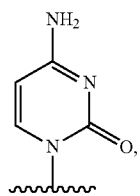 [SMILES: *n1ccc(N)nc1=O]
G is
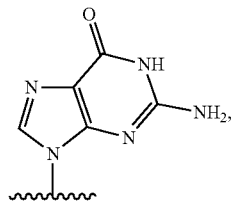 [SMILES: *n1cnc2c(=O)[nH]c(N)nc21]
and X is
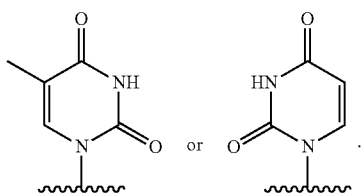
In certain embodiments, each X is independently
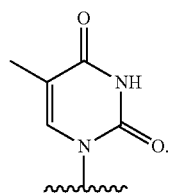
In some embodiments of the disclosure, including some embodiments of antisense oligomers of Formula (V) and embodiments of antisense oligomers of Formula (VI), the antisense oligomer is according to Formula (VII):

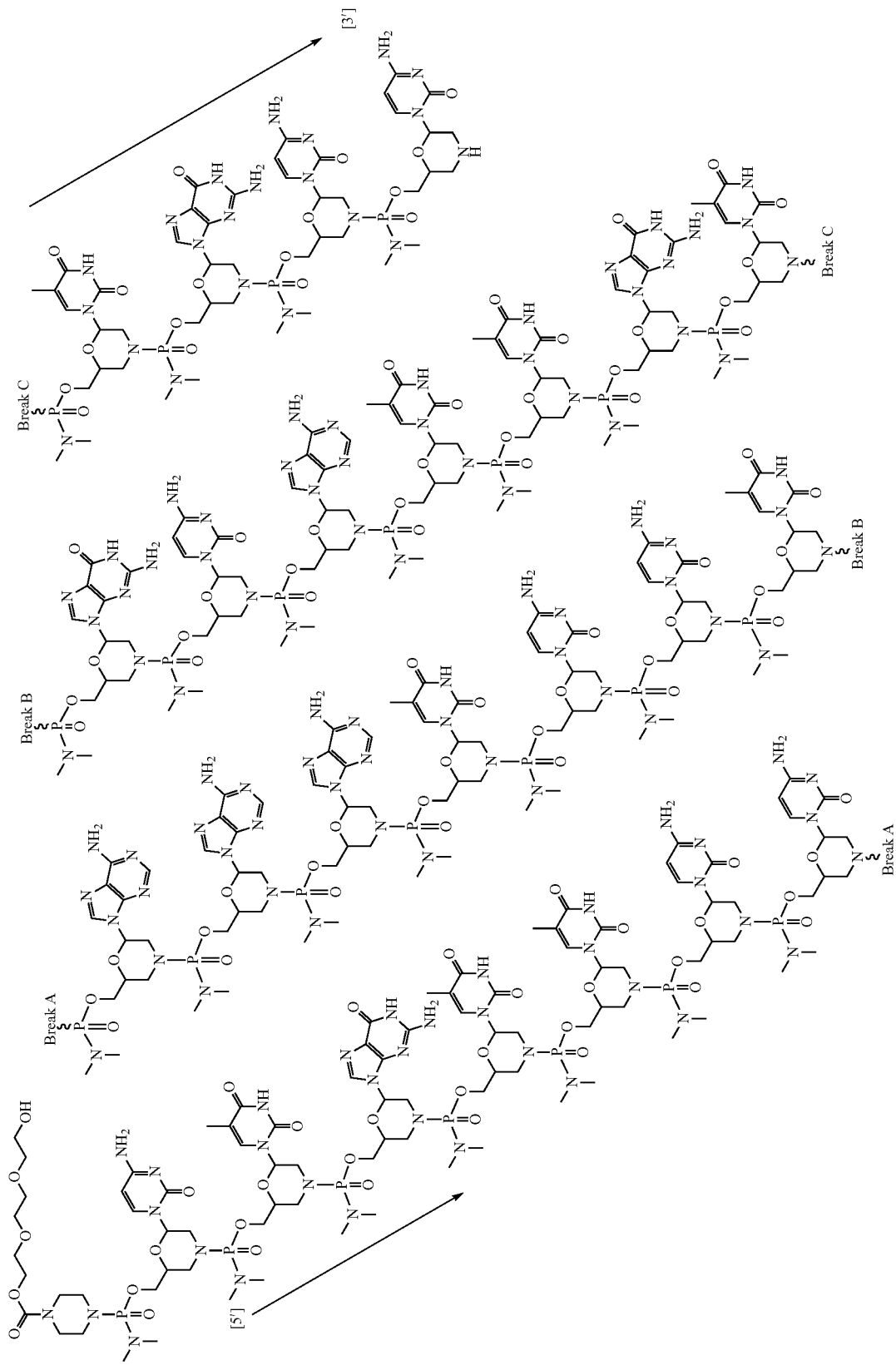
(VII)

or a pharmaceutically acceptable salt thereof.

In another aspect, the disclosure provides antisense oligomer conjugates of Formula (VIIA):

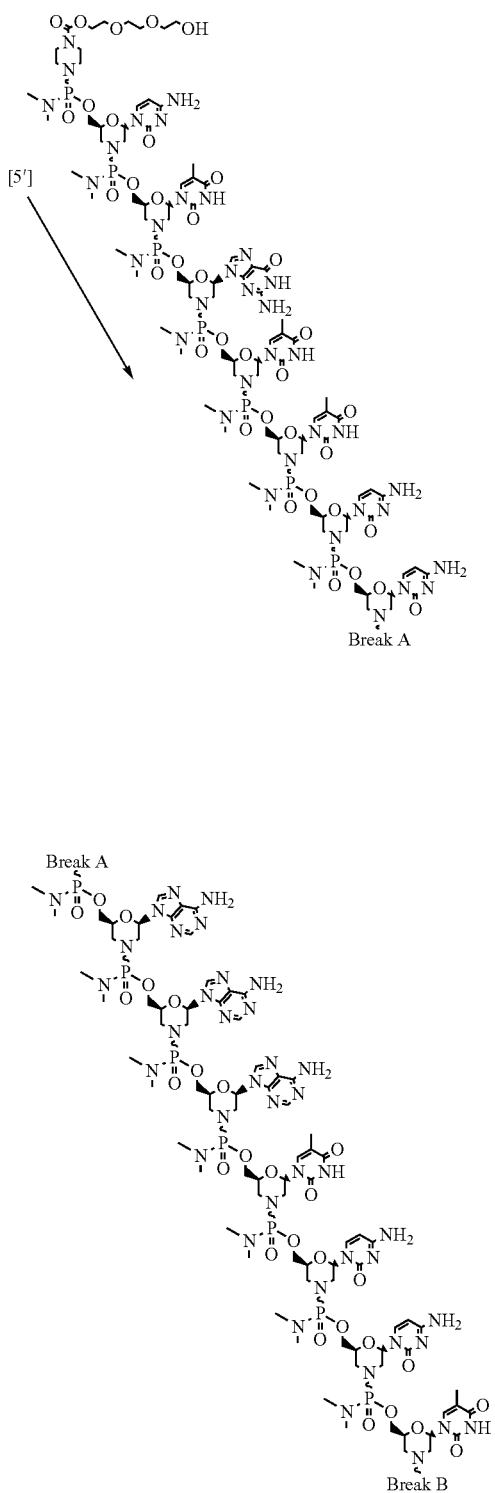

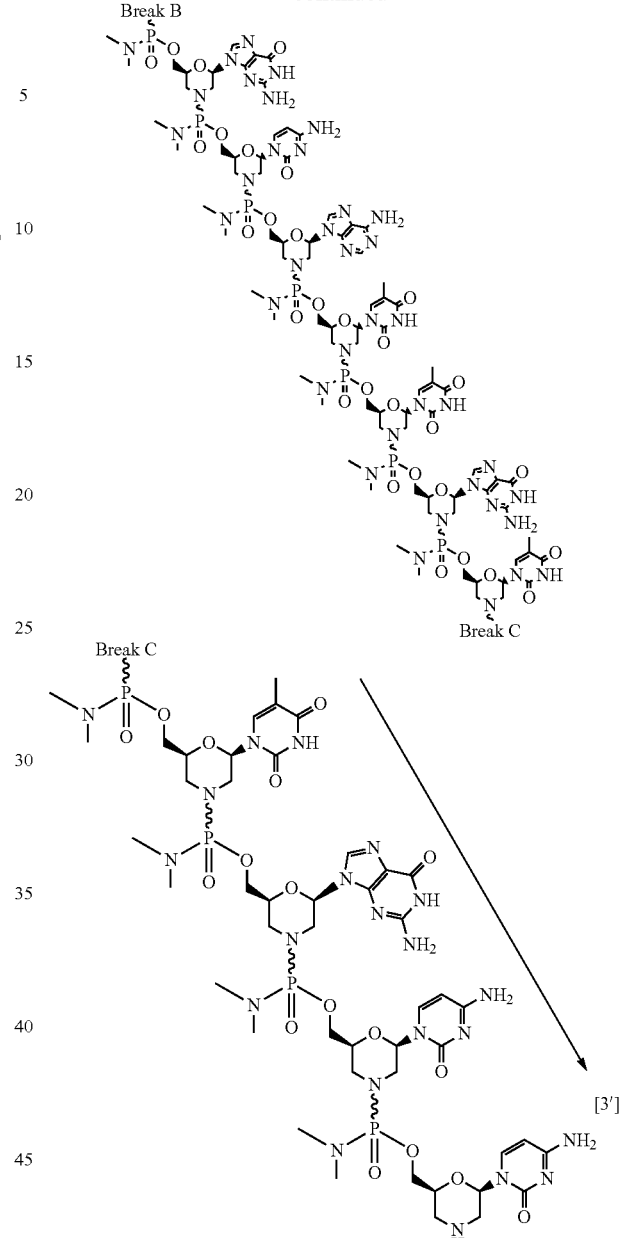

or a pharmaceutically acceptable salt thereof.

10. Nucleobase Modifications and Substitutions

In certain embodiments, antisense oligomers and antisense oligomer conjugates of the disclosure are composed of RNA nucleobases and DNA nucleobases (often referred to in the art simply as "base"). RNA bases are commonly known as adenine (A), uracil (U), cytosine (C) and guanine (G). DNA bases are commonly known as adenine (A), thymine (T), cytosine (C) and guanine (G). In various embodiments, antisense oligomers and antisense oligomer conjugates of the disclosure are composed of cytosine (C), guanine (G), thymine (T), adenine (A), 5-methylcytosine (5mC), uracil (U), and hypoxanthine (I).

In some embodiments, an antisense oligomer or an antisense oligomer conjugate of the disclosure comprises a sequence of nucleobases which taken together form a targeting sequence wherein the targeting sequence is complementary to an exon 52 annealing site in the dystrophin pre-mRNA designated as H52A(−01+24). In various embodiments, the sequence of nucleobases comprises the sequence of SEQ ID NO: 1. In some embodiments, the sequence of nucleobases consists of the sequence of SEQ ID NO: 1. In various embodiments, the sequence of nucleobases comprises a sequence having deletion, substitution, insertion and/or addition of 1 to 5 nucleobases in the sequence of SEQ ID NO:1. In various embodiments, the sequence of nucleobases consists of a sequence having deletion, substitution, insertion and/or addition of 1 to 5 nucleobases in the sequence of SEQ ID NO:1. In various embodiments, the targeting sequence has a region complementary to at least one string of three or more identical contiguous nucleobases in annealing sight site, wherein the annealing site comprises at least one additional nucleobase compared to the region of the targeting sequence and the at least one additional nucleobase has no complementary nucleobase in the region of the targeting sequence, and wherein the targeting region complementary to the at least one string of three or more identical contiguous nucleobases is internal to the targeting sequence, examples of which can be found in U.S. Patent Ser. No. 62/573,985, which is incorporated here entirely by reference.

In certain embodiments, one or more RNA bases or DNA bases in an oligomer may be modified or substituted with a base other than a RNA base or DNA base. Oligomers containing a modified or substituted base include oligomers in which one or more purine or pyrimidine bases most commonly found in nucleic acids are replaced with less common or non-natural bases.

Purine bases comprise a pyrimidine ring fused to an imidazole ring, as described by the following general formula.

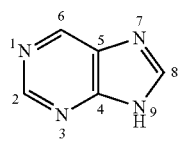

Purine

Adenine and guanine are the two purine nucleobases most commonly found in nucleic acids. Other naturally-occurring purines include, but not limited to, $N^6$-methyladenine, $N^2$-methylguanine, hypoxanthine, and 7-methylguanine.

Pyrimidine bases comprise a six-membered pyrimidine ring as described by the following general formula.

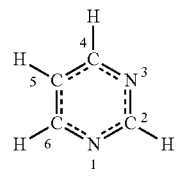

Pyrimidine

Cytosine, uracil, and thymine are the pyrimidine bases most commonly found in nucleic acids. Other naturally-occurring pyrimidines include, but not limited to, 5-methylcytosine, 5-hydroxymethylcytosine, pseudouracil, and 4-thiouracil. In one embodiment, the oligomers described herein contain thymine bases in place of uracil.

Other suitable bases include, but are not limited to: 2,6-diaminopurine, orotic acid, agmatidine, lysidine, 2-thio-pyrimidines (e.g. 2-thiouracil, 2-thiothymine), G-clamp and its derivatives, 5-substituted pyrimidines (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl-2-aminopurine (Pr-AP), pseudouracil, or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G, and Super T can be found in U.S. Pat. No. 6,683,173 (Epoch Biosciences), which is incorporated here entirely by reference. cPent-G, cPent-AP, and Pr-AP were shown to reduce immunostimulatory effects when incorporated in siRNA (Peacock H. et al. J. Am. Chem. Soc. 2011, 133, 9200). Pseudouracil is a naturally occuring isomerized version of uracil, with a C-glycoside rather than the regular N-glycoside as in uridine. Pseudouridine-containing synthetic mRNA may have an improved safety profile compared to uridine-containing mPvNA (WO 2009127230, incorporated here in its entirety by reference).

Certain nucleobases are particularly useful for increasing the binding affinity of the antisense oligomers and antisense oligomer conjugates of the disclosure. These include 5-substituted pyrimidines, 6-azapyrimidines, and N-2, N-6, and O-6 substituted purines, including 2-aminopropyladenine, 5-propynyluracil, and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications. Additional exemplary modified nucleobases include those wherein at least one hydrogen atom of the nucleobase is replaced with fluorine.

11. Pharmaceutically Acceptable Salts of Antisense Oligomers and Antisense Oligomer Conjugates Certain embodiments of antisense oligomers and antisense oligomer conjugates described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of antisense oligomers or antisense oligomer conjugates of the present disclosure. These salts can be prepared in situ in the administration vehicle or the dosage form manufacturing process, or by separately reacting a purified antisense oligomer or antisense oligomer conjugate of the disclosure in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject antisense oligomers or antisense oligomer conjugates include the conventional nontoxic salts or quaternary ammonium salts of the antisense oligomers or antisense oligomer conjugates, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the antisense oligomers and antisense oligomer conjugates of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of antisense oligomers or antisense oligomer conjugates of the present disclosure. These salts can likewise be prepared in situ in the administration vehicle or the dosage form manufacturing process, or by separately reacting the purified antisense oligomer or antisense oligomer conjugate in its free acid form with a suitable base, such as the hydroxide, carbonate, or bicarbonate of a pharmaceutically-acceptable metal cation, with ammonia, or with a pharmaceutically-acceptable organic primary, secondary, or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

III. Formulations and Modes of Administration

In certain embodiments, the present disclosure provides formulations or pharmaceutical compositions suitable for the therapeutic delivery of antisense oligomers and antisense oligomer conjugates, as described herein. Hence, in certain embodiments, the present disclosure provides pharmaceutically acceptable compositions that comprise a therapeutically-effective amount of one or more of the antisense oligomers or one or more of the antisense oligomer conjugates described herein, formulated together with one or more pharmaceutically acceptable carriers (additives) and/or diluents. While it is possible for an antisense oligomer or an antisense oligomer conjugate of the present disclosure to be administered alone, it is preferable to administer the antisense oligomer or an antisense oligomer conjugate as a pharmaceutical formulation (composition). In an embodiment, the antisense oligomer or the antisense oligomer conjugate of the formulation is according to Formula (III) or Formula (VII) respectively.

Methods for the delivery of nucleic acid molecules, which can be applicable to the antisense oligomers or the antisense oligomer conjugates of the present disclosure, are described, for example, in: Akhtar et al., 1992, Trends Cell Bio., 2:139; Delivery Strategies for Antisense Oligonucleotide Therapeutics, ed. Akhtar, 1995, CRC Press; and Sullivan et al., PCT WO 94/02595. These and other protocols can be utilized for the delivery of virtually any nucleic acid molecule, including the antisense oligomers and the antisense oligomer conjugates of the present disclosure.

The pharmaceutical compositions of the present disclosure may be specially formulated for administration in solid or liquid form, including those adapted for the following: (1) oral administration, for example, drenches (aqueous or non-aqueous solutions or suspensions), tablets (targeted for buccal, sublingual, or systemic absorption), boluses, powders, granules, pastes for application to the tongue; (2) parenteral administration, for example, by subcutaneous, intramuscular, intravenous, or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream, or foam; (5) sublingually; (6) ocularly; (7) transdermally; or (8) nasally.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates, and/or polyanhydrides; and (22) other non-toxic compatible substances employed in pharmaceutical formulations.

Additional non-limiting examples of agents suitable for formulation with the antisense oligomers or antisense oligomer conjugates of the instant disclosure include: PEG conjugated nucleic acids; phospholipid conjugated nucleic acids; nucleic acids containing lipophilic moieties; phosphorothioates; P-glycoprotein inhibitors (such as Pluronic P85) which can enhance entry of drugs into various tissues; biodegradable polymers, such as poly (D,L-lactide-coglycolide) microspheres for sustained release delivery after implantation (Emerich, D F et al., 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999).

The disclosure also features the use of the composition comprising surface-modified liposomes containing poly (ethylene glycol) ("PEG") lipids (PEG-modified, branched and unbranched or combinations thereof, or long-circulating liposomes or stealth liposomes). Antisense oligomers or antisense oligomer conjugates of the disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev.

1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present disclosure includes antisense oligomer pharmaceutical compositions and antisense oligomer conjugate pharmaceutical compositions prepared for delivery as described in U.S. Pat. Nos. 6,692,911; 7,163,695; and 7,070,807. In this regard, in one embodiment, the present disclosure provides an antisense oligomeror an antisense oligomer conjugate of the present disclosure in a composition comprising copolymers of lysine and histidine (HK) (as described in U.S. Pat. Nos. 7,163, 695; 7,070,807; and 6,692,911) either alone or in combination with PEG (e.g., branched or unbranched PEG or a mixture of both), in combination with PEG and a targeting moiety, or any of the foregoing in combination with a crosslinking agent. In certain embodiments, the present disclosure provides antisense oligomers or antisense oligomer conjugates in pharmaceutical compositions comprising gluconic-acid-modified polyhistidine or gluconylated-polyhistidine/transferrin-polylysine. One skilled in the art will also recognize that amino acids with properties similar to His and Lys may be substituted within the composition.

Wetting agents, emulsifiers and lubricants (such as sodium lauryl sulfate and magnesium stearate), coloring agents, release agents, coating agents, sweetening agents, flavoring agents, perfuming agents, preservatives, and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the subject being treated and the particular mode of administration. The amount of active ingredient which can be combined with a carrier material to produce a single dosage form will generally be that amount of the active ingredient which produces a therapeutic effect. Generally this amount will range from about 0.1 percent to about ninety-nine percent of active ingredient, preferably from about 5 percent to about 70 percent, most preferably from about 10 percent to about 30 percent.

In certain embodiments, a formulation of the present disclosure comprises an excipient selected from cyclodextrins, celluloses, liposomes, micelle forming agents, e.g., bile acids, and polymeric carriers, e.g., polyesters and polyanhydrides; and an antisense oligomer or an antisense oligomer conjugate of the present disclosure. In an embodiment, the antisense oligomer conjugate of the formulation is according to Formula (III). In an embodiment, the antisense oligomer of the formulation is according to Formula (VII). In certain embodiments, an aforementioned formulation renders orally bioavailable an antisense oligomer conjugate of the present disclosure.

Methods of preparing these formulations or pharmaceutical compositions include the step of bringing into association an antisense oligomer conjugate of the present disclosure with the carrier and, optionally, one or more accessory ingredients. In general, the formulations are prepared by uniformly and intimately bringing into association an antisense oligomer conjugate of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an antisense oligomer conjugate of the present disclosure as an active ingredient. An antisense oligomer conjugate of the present disclosure may also be administered as a bolus, electuary, or paste.

In solid dosage forms of the disclosure for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid pharmaceutical compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid pharmaceutical compositions which can be dissolved in sterile water, or some other sterile injectable medium immediately before use. These pharmaceutical compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the antisense oligomer conjugates of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomer conjugates may be mixed under sterile conditions with a pharmaceutically-acceptable carrier, and with any preservatives, buffers, or propellants which may be required. The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an antisense oligomer conjugate of the present disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an antisense oligomer conjugate of the present disclosure to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomer conjugates of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In an embodiment, the antisense oligomer or the antisense oligomer conjugate of the pharmaceutical composition is according to Formula (III) or Formula (VII) respectively.

These pharmaceutical compositions may also contain adjuvants such as preservatives, wetting agents, emulsifying agents and dispersing agents. Prevention of the action of microorganisms upon the subject oligomer conjugates may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomer conjugates in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly (anhydrides). Depot injectable formulations may also prepared by entrapping the drug in liposomes or microemulsions that are compatible with body tissues.

When the antisenseoligomer conjugates of the present disclosure are administered as pharmaceuticals, to humans and animals, they can be given per se or as a pharmaceutical composition containing, for example, 0.1 to 99% (more preferably, 10 to 30%) of the antisense oligomer conjugate in combination with a pharmaceutically acceptable carrier.

The formulations or preparations of the present disclosure may be given orally, parenterally, topically, or rectally. They are typically given in forms suitable for each administration route. For example, they are administered in tablets or capsule form, by injection, inhalation, eye lotion, ointment, suppository, or infusion; topically by lotion or ointment; or rectally by suppositories.

Regardless of the route of administration selected, the antisense oligomer conjugates of the present disclosure, which may be used in a suitable hydrated form, and/or the pharmaceutical compositions of the present disclosure, may be formulated into pharmaceutically-acceptable dosage forms by conventional methods known to those of skill in the art. Actual dosage levels of the active ingredients in the pharmaceutical compositions of this disclosure may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular antisense oligomer conjugate of the present disclosure employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the antisense oligomer conjugates of the disclosure employed in the pharmaceutical composition at levels lower than that required in order to achieve the desired therapeutic effect and gradually increase the dosage until the desired effect is achieved. In general, a suitable daily dose of an antisense oligomer conjugate of the disclosure will be that amount of the antisense oligomer conjugate which is the lowest dose effective to produce a therapeutic effect. Such an effective dose will generally depend upon the factors described herein. Generally, oral, intravenous, intracerebroventricular and subcutaneous doses of the antisense oligomer conjugates of this disclosure for a patient, when used for the indicated effects, will range from about 0.0001 to about 100 mg per kilogram of body weight per day.

In some embodiments, the antisense oligomer conjugates of the present disclosure are administered in doses generally from about 10-160 mg/kg or 20-160 mg/kg. In some cases, doses of greater than 160 mg/kg may be necessary. In some embodiments, doses for i.v. administration are from about 0.5 mg to 160 mg/kg. In some embodiments, the antisense oligomer conjugates are administered at doses of about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In some embodiments, the antisense oligomer conjugates are administered at doses of about 10 mg/kg, 11 mg/kg, 12 mg/kg, 15 mg/kg, 18 mg/kg, 20 mg/kg, 21 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, including all integers in between. In some embodiments, the oligomer is administered at 10 mg/kg. In some embodiments, the oligomer is administered at 20 mg/kg. In some embodiments, the oligomer is administered at 30 mg/kg. In some embodiments, the oligomer is administered at 40 mg/kg. In some embodiments, the oligomer is administered at 60 mg/kg. In some embodiments, the oligomer is administered at 80 mg/kg. In some embodiments, the oligomer is administered at 160 mg/kg. In some embodiments, the oligomer is administered at 50 mg/kg.

In some embodiments, the antisense oligomers of the present disclosure are administered in doses generally from about 10-160 mg/kg or 20-160 mg/kg. In some cases, doses of greater than 160 mg/kg may be necessary. In some embodiments, doses for i.v. administration are from about 0.5 mg to 160 mg/kg. In some embodiments, the antisense oligomers are administered at doses of about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In some embodiments, the antisense oligomers are administered at doses of about 10 mg/kg, 11 mg/kg, 12 mg/kg, 15 mg/kg, 18 mg/kg, 20 mg/kg, 21 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, including all integers in between. In some embodiments, the antisense oligomer is administered at 10 mg/kg. In some embodiments, the antisense oligomer is administered at 20 mg/kg. In some embodiments, the antisense oligomer is administered at 30 mg/kg. In some embodiments, the antisense oligomer is administered at 40 mg/kg. In some embodiments, the antisense oligomer is administered at 60 mg/kg. In some embodiments, the antisense oligomer is administered at 80 mg/kg. In some embodiments, the antisense oligomer is administered at 160 mg/kg. In some embodiments, the antisense oligomer is administered at 50 mg/kg.

In some embodiments, the antisense oligomer conjugate of Formula (III) is administered in doses generally from about 10-160 mg/kg or 20-160 mg/kg. In some embodiments, doses of the antisense oligomer conjugate of Formula (III) for i.v. administration are from about 0.5 mg to 160 mg/kg. In some embodiments, the antisense oligomer conjugate of Formula (III) is administered at doses of about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In some embodiments, the antisense oligomer conjugate of Formula (III) is administered at doses of about 10 mg/kg, 11 mg/kg, 12 mg/kg, 15 mg/kg, 18 mg/kg, 20 mg/kg, 21 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, including all integers in between. In some embodiments, the antisense oligomer conjugate of Formula (III) is administered at 10 mg/kg. In some embodiments, the antisense oligomer conjugate of Formula (III) is administered at 20 mg/kg. In some embodiments, the antisense oligomer conjugate of Formula (III) is administered at 30 mg/kg. In some embodiments, the antisense oligomer conjugate of Formula (III) is administered at 40 mg/kg. In some embodiments, the antisense oligomer conjugate of Formula (III) is administered at 60 mg/kg. In some embodiments, the antisense oligomer conjugate of Formula (III) is administered at 80 mg/kg. In some embodiments, the antisense oligomer conjugate of Formula (III) is administered at 160 mg/kg. In some embodiments, the antisense oligomer conjugate of Formula (III) is administered at 50 mg/kg.

In some embodiments, the antisense oligomer of Formula (IV) is administered in doses generally from about 10-160 mg/kg or 20-160 mg/kg. In some embodiments, doses of the antisense oligomer of Formula (IV) for i.v. administration are from about 0.5 mg to 160 mg/kg. In some embodiments, the antisense oligomer of Formula (IV) is administered at doses of about 10 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In some embodiments, the antisense oligomer of Formula (IV) is administered at doses of about 10 mg/kg, 11 mg/kg, 12 mg/kg, 15 mg/kg, 18 mg/kg, 20 mg/kg, 21 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, including all integers in between. In some embodiments, the antisense oligomer of Formula (IV) is administered at 10 mg/kg. In some embodiments, the antisense oligomer of Formula (IV) is administered at 20 mg/kg. In some embodiments, the antisense oligomer of Formula (IV) is administered at 30 mg/kg. In some embodiments, the antisense oligomer of Formula (IV) is administered at 40 mg/kg. In some embodiments, the antisense oligomer of Formula (IV) is administered at 60 mg/kg. In some embodiments, the antisense oligomer of Formula (IV) is administered at 80 mg/kg. In some embodiments, the antisense oligomer of Formula (IV) is administered at 160 mg/kg. In some embodiments, the antisense oligomer of Formula (IV) is administered at 50 mg/kg.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to maintain the desired expression of a functional dystrophin protein. In certain embodiments, dosing is one or more administrations once every two weeks. In some embodiments, dosing is one administration once every two weeks. In various embodiments, dosing is one or more administrations every month. In certain embodiments, dosing is one administration every month.

In various embodiments, the antisense oligomer conjugates are administered weekly at 10 mg/kg. In various embodiments, the antisense oligomer conjugates are administered weekly at 20 mg/kg. In various embodiments, the antisense oligomer conjugates are administered weekly at 30 mg/kg. In various embodiments, the antisense oligomer conjugates are administered weekly at 40 mg/kg. In some embodiments, the antisense oligomer conjugates are administered weekly at 60 mg/kg. In some embodiments, the antisense oligomer conjugates are administered weekly at 80 mg/kg. In some embodiments, the antisense oligomer conjugates are administered weekly at 100 mg/kg. In some embodiments, the antisense oligomer conjugates are administered weekly at 160 mg/kg. As used herein, weekly is understood to have the art-accepted meaning of every week.

In various embodiments, the antisense oligomers are administered weekly at 10 mg/kg. In various embodiments, the antisense oligomers are administered weekly at 20 mg/kg. In various embodiments, the antisense oligomers are administered weekly at 30 mg/kg. In various embodiments, the antisense oligomers are administered weekly at 40 mg/kg. In some embodiments, the antisense oligomers are administered weekly at 60 mg/kg. In some embodiments, the antisense oligomers are administered weekly at 80 mg/kg. In some embodiments, the antisense oligomers are administered weekly at 100 mg/kg. In some embodiments, the antisense oligomers are administered weekly at 160 mg/kg. As used herein, weekly is understood to have the art-accepted meaning of every week.

In various embodiments, the antisense oligomer conjugates are administered biweekly at 10 mg/kg. In various embodiments, the antisense oligomer conjugates are administered biweekly at 20 mg/kg. In various embodiments, the antisense oligomer conjugates are administered biweekly at 30 mg/kg. In various embodiments, the antisense oligomer conjugates are administered biweekly at 40 mg/kg. In some embodiments, the antisense oligomer conjugates are administered biweekly at 60 mg/kg. In some embodiments, the antisense oligomer conjugates are administered biweekly at 80 mg/kg. In some embodiments, the antisense oligomer conjugates are administered biweekly at 100 mg/kg. In some embodiments, the antisense oligomer conjugates are administered biweekly at 160 mg/kg. As used herein, biweekly is understood to have the art-accepted meaning of every two weeks.

In various embodiments, the antisense oligomers are administered biweekly at 10 mg/kg. In various embodiments, the antisense oligomers are administered biweekly at 20 mg/kg. In various embodiments, the antisense oligomers are administered biweekly at 30 mg/kg. In various embodiments, the antisense oligomers are administered biweekly at 40 mg/kg. In some embodiments, the antisense oligomers are administered biweekly at 60 mg/kg. In some embodiments, the antisense oligomers are administered biweekly at 80 mg/kg. In some embodiments, the antisense oligomers are administered biweekly at 100 mg/kg. In some embodiments, the antisense oligomers are administered biweekly at 160 mg/kg. As used herein, biweekly is understood to have the art-accepted meaning of every two weeks.

In various embodiments, the antisense oligomer conjugates are administered every third week at 10 mg/kg. In various embodiments, the antisense oligomer conjugates are administered every third week at 20 mg/kg. In various embodiments, the antisense oligomer conjugates are administered every third week at 30 mg/kg. In various embodiments, the antisense oligomer conjugates are administered every third week at 40 mg/kg. In some embodiments, the antisense oligomer conjugates are administered every third week at 60 mg/kg. In some embodiments, the antisense oligomer conjugates are administered every third week at 80 mg/kg. In some embodiments, the antisense oligomer conjugates are administered every third week at 100 mg/kg. In some embodiments, the antisense oligomer conjugates are administered every third week at 160 mg/kg. As used herein, every third week is understood to have the art-accepted meaning of once every three weeks.

In various embodiments, the antisense oligomers are administered every third week at 10 mg/kg. In various embodiments, the antisense oligomers are administered every third week at 20 mg/kg. In various embodiments, the antisense oligomers are administered every third week at 30 mg/kg. In various embodiments, the antisense oligomers are administered every third week at 40 mg/kg. In some embodiments, the antisense oligomers are administered every third week at 60 mg/kg. In some embodiments, the antisense oligomers are administered every third week at 80 mg/kg. In some embodiments, the antisense oligomers are administered every third week at 100 mg/kg. In some embodiments, the antisense oligomers are administered every third week at 160 mg/kg. As used herein, every third week is understood to have the art-accepted meaning of once every three weeks.

In various embodiments, the antisense oligomer conjugates are administered monthly at 10 mg/kg. In various embodiments, the antisense oligomer conjugates are administered monthly at 20 mg/kg. In various embodiments, the antisense oligomer conjugates are administered monthly at 30 mg/kg. In various embodiments, the antisense oligomer conjugates are administered monthly at 40 mg/kg. In some embodiments, the antisense oligomer conjugates are administered monthly at 60 mg/kg. In some embodiments, the antisense oligomer conjugates are administered monthly at 80 mg/kg. In some embodiments, the antisense oligomer conjugates are administered monthly at 100 mg/kg. In some embodiments, the antisense oligomer conjugates are administered monthly at 160 mg/kg. As used herein, monthly is understood to have the art-accepted meaning of every month.

In various embodiments, the antisense oligomers are administered monthly at 10 mg/kg. In various embodiments, the antisense oligomers are administered monthly at 20 mg/kg. In various embodiments, the antisense oligomers are administered monthly at 30 mg/kg. In various embodiments, the antisense oligomers are administered monthly at 40 mg/kg. In some embodiments, the antisense oligomers are administered monthly at 60 mg/kg. In some embodiments, the antisense oligomers are administered monthly at 80 mg/kg. In some embodiments, the antisense oligomers are administered monthly at 100 mg/kg. In some embodiments, the antisense oligomers are administered monthly at 160 mg/kg. As used herein, monthly is understood to have the art-accepted meaning of every month.

As would be understood in the art, weekly, biweekly, every third week, or monthly administrations may be in one or more administrations or sub-doses as discussed herein.

Nucleic acid molecules, antisense oligomers, and antisense oligomer conjugates described herein can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of disclosure, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize an antisense oligomer conjugate of the present disclosure and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-poly(ethylene glycol) esters of the corresponding fatty acids, with a particularly preferred fatty acid composition including capric acid 4-10%, capric acid 3-9%, lauric acid 40-50%, myristic acid 14-24%, palmitic acid 4-14%, and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc. (produced and distributed by a number of companies in USA and worldwide).

In certain embodiments, the delivery may occur by use of liposomes, nanocapsules, microparticles, microspheres, lipid particles, vesicles, and the like, for the introduction of the pharmaceutical compositions of the present disclosure into suitable host cells. In particular, the pharmaceutical compositions of the present disclosure may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present disclosure are those which are readily water-soluble, can be covalently attached to a vesicle-forming lipid, and which are tolerated in vivo without toxic effects (i.e., are biocompatible). Suitable polymers include poly(ethylene glycol) (PEG), polylactic (also termed polylactide), polyglycolic acid (also termed polyglycolide), a polylactic-polyglycolic acid copolymer, and polyvinyl alcohol. In certain embodiments, polymers have a weight average molecular weight of from about 100 or 120 daltons up to about 5,000 or 10,000 daltons, or from about 300 daltons to about 5,000 daltons. In other embodiments, the polymer is poly(ethylene glycol) having a weight average molecular weight of from about 100 to about 5,000 daltons, or having a weight average molecular weight of from about 300 to about 5,000 daltons. In certain embodiments, the polymer is a poly(ethylene glycol) having a weight average molecular weight of about 750 daltons, for example PEG(750). Polymers may also be defined by the number of monomers therein; a preferred embodiment of the present disclosure utilizes polymers of at least about three monomers, such PEG polymers consisting of three monomers have a molecular weight of approximately 132 daltons.

Other hydrophilic polymers which may be suitable for use in the present disclosure include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present disclosure comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7, or 8 glucose units, designated by the Greek letter α, β, or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several non-concentric membranes, i.e., several smaller vesicles contained within a larger vesicle, are termed multivesicular vesicles.

One aspect of the present disclosure relates to formulations comprising liposomes containing an antisense oligomer or antisense oligomer conjugate of the present disclosure, where the liposome membrane is formulated to provide a liposome with increased carrying capacity. Alternatively or in addition, the antisense oligomer or antisense oligomer conjugate of the present disclosure may be contained within, or adsorbed onto, the liposome bilayer of the liposome. An antisense oligomer or antisense oligomer conjugate of the present disclosure may be aggregated with a lipid surfactant and carried within the liposome's internal space; in these cases, the liposome membrane is formulated to resist the disruptive effects of the active agent-surfactant aggregate.

According to one embodiment of the present disclosure, the lipid bilayer of a liposome contains lipids derivatized with poly(ethylene glycol) (PEG), such that the PEG chains extend from the inner surface of the lipid bilayer into the interior space encapsulated by the liposome, and extend from the exterior of the lipid bilayer into the surrounding environment.

Active agents contained within liposomes of the present disclosure are in solubilized form. Aggregates of surfactant and active agent (such as emulsions or micelles containing the active agent of interest) may be entrapped within the interior space of liposomes according to the present disclosure. A surfactant acts to disperse and solubilize the active agent, and may be selected from any suitable aliphatic, cycloaliphatic or aromatic surfactant, including but not limited to biocompatible lysophosphatidylcholines (LPGs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMOs in the micromolar range; higher CMC surfactants may be utilized to prepare micelles entrapped within liposomes of the present disclosure.

Liposomes according to the present disclosure may be prepared by any of a variety of techniques that are known in the art. See, e.g., U.S. Pat. No. 4,235,871; Published PCT application WO 96/14057; New RRC, Liposomes: A practical approach, IRL Press, Oxford (1990), pages 33-104; and Lasic D D, Liposomes from physics to applications, Elsevier Science Publishers BV, Amsterdam, 1993. For example, liposomes of the present disclosure may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present disclosure, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation of the present disclosure depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and 30 percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An antisense oligomer or antisense oligomer conjugate may be formulated to be contained within, or, adapted to release by a surgical or medical device or implant. In certain aspects, an implant may be coated or otherwise treated with an antisense oligomer conjugate. For example, hydrogels, or other polymers, such as biocompatible and/or biodegradable polymers, may be used to coat an implant with the pharmaceutical compositions of the present disclosure (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the antisense oligomers or antisense oligomer conjugates for use according to the disclosure may be formulated for administration in any convenient way for use in human or veterinary medicine, by analogy with other pharmaceuticals. The antisense oligomers and antisense oligomer conjugates and their corresponding formulations may be administered alone or in combination with other therapeutic strategies in the treatment of muscular dystrophy, such as myoblast transplantation, stem cell therapies, administration of aminoglycoside antibiotics, proteasome inhibitors, and up-regulation therapies (e.g., upregulation of utrophin, an autosomal paralogue of dystrophin).

In some embodiments, the additional therapeutic may be administered prior, concurrently, or subsequently to the administration of the antisense oligomer conjugate of the present disclosure. For example, the antisense oligomer conjugates may be administered in combination with a steroid and/or antibiotic. In certain embodiments, the antisense oligomer conjugates are administered to a patient that is on background steroid theory (e.g., intermittent or chronic/continuous background steroid therapy). For example, in some embodiments the patient has been treated with a corticosteroid prior to administration of an antisense oligomer and continues to receive the steroid therapy. In some embodiments, the steroid is glucocorticoid or prednisone.

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann (1989) Science, 244:1275-1280). These approaches include integration of the gene to be expressed into modified retroviruses (Friedmann (1989) supra; Rosenberg (1991) Cancer Research 51(18), suppl.: 5074S-5079S); integration into non-retrovirus vectors (e.g., adeno-associated viral vectors) (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra; Wolff et al. (1990) Science, 247:1465-1468). Direct injection of transgenes into tissue produces only localized expression (Rosenfeld (1992) supra; Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256: 808-813.

In a further embodiment, pharmaceutical compositions of the disclosure may additionally comprise a carbohydrate as provided in Han et al., Nat. Comms. 7, 10981 (2016) the entirety of which is incorporated herein by reference. In some embodiments, pharmaceutical compositions of the disclosure may comprise 5% of a hexose carbohydrate. For example, pharmaceutical composition of the disclosure may comprise 5% glucose, 5% fructose, or 5% mannose. In certain embodiments, pharmaceutical compositions of the disclosure may comprise 2.5% glucose and 2.5% fructose. In some embodiments, pharmaceutical compositions of the disclosure may comprises a carbohydrate selected from: arabinose present in an amount of 5% by volume, glucose present in an amount of 5% by volume, sorbitol present in an amount of 5% by volume, galactose present in an amount of 5% by volume, fructose present in an amount of 5% by volume, xylitol present in an amount of 5% by volume, mannose present in an amount of 5% by volume, a combination of glucose and fructose each present in an amount of 2.5% by volume, and a combination of glucose present in an amount of 5.7% by volume, fructose present in an amount of 2.86% by volume, and xylitol present in an amount of 1.4% by volume.

IV. Methods of Use

Restoration of the Dystrophin Reading Frame Using Exon Skipping

A potential therapeutic approach to the treatment of DMD caused by out-of-frame mutations in the dystrophin gene is suggested by the milder form of dystrophinopathy known as BMD, which is caused by in-frame mutations. The ability to convert an out-of-frame mutation to an in-frame mutation would hypothetically preserve the mRNA reading frame and produce an internally shortened yet functional dystrophin protein. Antisense oligomers and antisense oligomer conjugates of the disclosure were designed to accomplish this.

Hybridization of the PMO with the targeted pre-mRNA sequence interferes with formation of the pre-mRNA splicing complex and deletes exon 52 from the mature mRNA. The structure and conformation of antisense oligomers and antisense oligomer conjugates of the disclosure allow for sequence-specific base pairing to the complementary sequence. By similar mechanism, eteplirsen, for example, which is a PMO that was designed to skip exon 51 of dystrophin pre-mRNA allows for sequence-specific base pairing to the complementary sequence contained in exon 51 of dystrophin pre-mRNA.

Normal dystrophin mRNA containing all 79 exons will produce normal dystrophin protein. The graphic in FIG. 1 depicts a small section of the dystrophin pre-mRNA and mature mRNA, from exon 47 to exon 52. The shape of each exon depicts how codons are split between exons; of note, one codon consists of three nucleotides. Rectangular shaped exons start and end with complete codons. Arrow shaped exons start with a complete codon but end with a split codon, containing only nucleotide #1 of the codon. Nucleotides #2 and #3 of this codon are contained in the subsequent exon which will start with a chevron shape.

Dystrophin mRNA missing whole exons from the dystrophin gene typically result in DMD. The graphic in FIG. 2 illustrates a type of genetic mutation (deletion of exon 50) that is known to result in DMD. Since exon 49 ends in a complete codon and exon 51 begins with the second nucleotide of a codon, the reading frame after exon 49 is shifted, resulting in out-of-frame mRNA reading frame and incorporation of incorrect amino acids downstream from the mutation. The subsequent absence of a functional C-terminal dystroglycan binding domain results in production of an unstable dystrophin protein.

Figure 3:
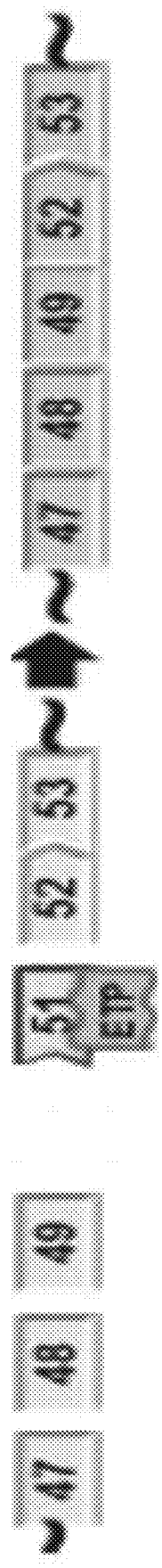
FIG. 3 depicts eteplirsen, designed to skip exon 51, restoration of "In-frame" reading of pre-mRNA.

Eteplirsen skips exon 51 to restore the mRNA reading frame. Since exon 49 ends in a complete codon and exon 52 begins with the first nucleotide of a codon, deletion of exon 51 restores the reading frame, resulting in production of an internally-shortened dystrophin protein with an intact dystroglycan binding site, similar to an "in-frame" BMD mutation (FIG. 3).

The feasibility of ameliorating the DMD phenotype using exon skipping to restore the dystrophin mRNA open reading frame is supported by nonclinical research. Numerous studies in dystrophic animal models of DMD have shown that restoration of dystrophin by exon skipping leads to reliable improvements in muscle strength and function (Sharp 2011; Yokota 2009; Wu 2008; Wu 2011; Barton-Davis 1999; Goyenvalle 2004; Gregorevic 2006; Yue 2006; Welch 2007; Kawano 2008; Reay 2008; van Putten 2012). A compelling example of this comes from a study in which dystrophin levels following exon skipping (using a PMO) therapy were compared with muscle function in the same tissue. In dystrophic mdx mice, tibialis anterior (TA) muscles treated with a mouse-specific PMO maintained ~75% of their maximum force capacity after stress-inducing contractions, whereas untreated contralateral TA muscles maintained only ~25% of their maximum force capacity (p<0.05) (Sharp 2011). In another study, 3 dystrophic CMD dogs received, at 2-5 months of age, exon-skipping therapy using a PMO-specific for their genetic mutation once a week for 5 to 7 weeks or every other week for 22 weeks. Following exon-skipping therapy, all 3 dogs demonstrated extensive, body-wide expression of dystrophin in skeletal muscle, as well as maintained or improved ambulation (15 m running test) relative to baseline. In contrast, untreated age-matched CMD dogs showed a marked decrease in ambulation over the course of the study (Yokota 2009).

PMOs were shown to have more exon skipping activity at equimolar concentrations than phosphorothioates in both mdx mice and in the humanized DMD (hDMD) mouse model, which expresses the entire human DMD transcript (Heemskirk 2009). In vitro experiments using reverse transcription polymerase chain reaction (RT-PCR) and Western blot (WB) in normal human skeletal muscle cells or muscle cells from DMD patients with different mutations amenable to exon 51 skipping identified eteplirsen (a PMO) as a potent inducer of exon 51 skipping. Eteplirsen-induced exon 51 skipping has been confirmed in vivo in the hDMD mouse model (Arechavala-Gomeza 2007).

Clinical outcomes for analyzing the effect of an antisense oligomer or an antisense oligomer conjugate that is complementary to a target region of exon 52 of the human dystrophin pre-mRNA and induces exon 52 skipping include percent dystrophin positive fibers (PDPF), six-minute walk test (6MWT), loss of ambulation (LOA), North Star Ambulatory Assessment (NSAA), pulmonary function tests (PFT), ability to rise (from a supine position) without external support, de novo dystrophin production, and other functional measures.

In some embodiments, the present disclosure provides methods for producing dystrophin in a subject having a mutation of the dystrophin gene that is amenable to exon 52 skipping, the method comprising administering to the subject an antisense oligomer conjugate, or pharmaceutically acceptable salt thereof, as described herein. In some embodiments, the present disclosure provides methods for producing dystrophin in a subject having a mutation of the dystrophin gene that is amenable to exon 52 skipping, the method comprising administering to the subject an antisense oligomer, or pharmaceutically acceptable salt thereof, as described herein. In certain embodiments, the present disclosure provides methods for restoring an mRNA reading frame to induce dystrophin protein production in a subject with Duchenne muscular dystrophy (DMD) who has a mutation of the dystrophin gene that is amenable to exon 52 skipping. Protein production can be measured by reverse-transcription polymerase chain reaction (RT-PCR), western blot analysis, or immunohistochemistry (IHC).

In some embodiments, the present disclosure provides methods for treating DMD in a subject in need thereof, wherein the subject has a mutation of the dystrophin gene that is amenable to exon 52 skipping, the method comprising administering to the subject an antisense oligomer conjugate, or pharmaceutically acceptable salt thereof, as described herein. In some embodiments, the present disclosure provides methods for treating DMD in a subject in need thereof, wherein the subject has a mutation of the dystrophin gene that is amenable to exon 52 skipping, the method comprising administering to the subject an antisense oligomer, or pharmaceutically acceptable salt thereof, as described herein. In various embodiments, treatment of the subject is measured by delay of disease progression. In some embodiments, treatment of the subject is measured by maintenance of ambulation in the subject or reduction of loss of ambulation in the subject. In some embodiments, ambulation is measured using the 6 Minute Walk Test (6MWT). In certain embodiments, ambulation is measured using the North Start Ambulatory Assessment (NSAA).

In various embodiments, the present disclosure provides methods for maintaining pulmonary function or reducing loss of pulmonary function in a subject with DMD, wherein the subject has a mutation of the DMD gene that is amenable to exon 52 skipping, the method comprising administering to the subject an antisense oligomer conjugate, or pharmaceutically acceptable salt thereof, as described herein. In various embodiments, the present disclosure provides methods for maintaining pulmonary function or reducing loss of pulmonary function in a subject with DMD, wherein the subject has a mutation of the DMD gene that is amenable to exon 52 skipping, the method comprising administering to the subject an antisense oligomer, or pharmaceutically acceptable salt thereof, as described herein. In some embodiments, pulmonary function is measured as Maximum Expiratory Pressure (MEP). In certain embodiments, pulmonary function is measured as Maximum Inspiratory Pressure (MIP). In some embodiments, pulmonary function is measured as Forced Vital Capacity (FVC).

In a further embodiment, the pharmaceutical compositions of the disclosure may be co-administered with a carbohydrate in the methods of the disclosure, either in the same formulation or is a separate formulation, as provided in Han et al., Nat. Comms. 7, 10981 (2016) the entirety of which is incorporated herein by reference. In some embodiments, pharmaceutical compositions of the disclosure may be co-administered with 5% of a hexose carbohydrate. For example, pharmaceutical compositions of the disclosure may be co-administered with 5% glucose, 5% fructose, or 5% mannose. In certain embodiments, pharmaceutical compositions of the disclosure may be co-administered with 2.5% glucose and 2.5% fructose. In some embodiments, pharmaceutical composition of the disclosure may be co-administered with a carbohydrate selected from: arabinose present in an amount of 5% by volume, glucose present in an amount of 5% by volume, sorbitol present in an amount of 5% by volume, galactose present in an amount of 5% by volume, fructose present in an amount of 5% by volume, xylitol present in an amount of 5% by volume, mannose present in an amount of 5% by volume, a combination of glucose and fructose each present in an amount of 2.5% by volume, and a combination of glucose present in an amount of 5.7% by volume, fructose present in an amount of 2.86% by volume, and xylitol present in an amount of 1.4% by volume.

In various embodiments, an antisense oligomer or antisense oligomer conjugate of the disclosure is co-administered with a therapeutically effective amount of a non-steroidal anti-inflammatory compound. In some embodiments, the non-steroidal anti-inflammatory compound is an NF-kB inhibitor. For example, in some embodiments, the NF-kB inhibitor may be CAT-1004 or a pharmaceutically acceptable salt thereof. In various embodiments, the NF-kB inhibitor may be a conjugate of salicylate and DHA. In some embodiments, the NF-kB inhibitor is CAT-1041 or a pharmaceutically acceptable salt thereof. In certain embodiments, the NF-kB inhibitor is a conjugate of salicylate and EPA. In various embodiments, the NF-kB inhibitor is

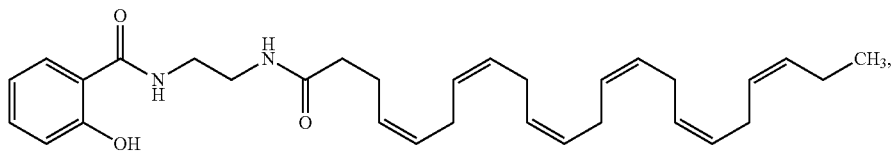 [SMILES: CC/C=C\C/C=C\C/C=C\C/C=C\C/C=C\C/C=C\CCC(=O)NCCNC(=O)c1ccccc1O]

pharmaceutically acceptable salt thereof.

In some embodiments, non-steroidal anti-inflammatory compound is a TGF-b inhibitor. For example, in certain embodiments, the TGF-b inhibitor is HT-100.

In certain embodiments, there is described an antisense oligomer and antisense oligomer conjugate as described herein for use in therapy. In certain embodiments, there is described an antisense oligomer and antisense oligomer conjugate as described herein for use in the treatment of Duchenne muscular dystrophy. In certain embodiments, there is described an antisense oligomer and antisense oligomer conjugate as described herein for use in the manufacture of a medicament for use in therapy. In certain embodiments, there is described an antisense oligomer and antisense oligomer conjugate as described herein for use in the manufacture of a medicament for the treatment of Duchenne muscular dystrophy.

V. Kits

The disclosure also provides kits for treatment of a patient with a genetic disease which kit comprises at least an antisense molecule (e.g., an antisense oligomer comprising the base sequence set forth in SEQ ID NO: 1 or an antisense oligomer conjugate comprising the antisense oligomer comprising the base sequence set forth in SEQ ID NO: 1), packaged in a suitable container, together with instructions for its use. The kits may also contain peripheral reagents such as buffers, stabilizers, etc. Those of ordinary skill in the field should appreciate that applications of the above method has wide application for identifying antisense molecules suitable for use in the treatment of many other diseases. In an embodiment, the kit comprises an antisense oligomer conjugate according to Formula (III) or an antisense oligomer according to Formula (IV).

EXAMPLES

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.
Materials and Methods
Cells and Tissue Culture Treatment Conditions Differentiated human myocytes (ZenBio, Inc.) were utilized to measure exon skipping. Specifically, myoblasts (ZenBio, Inc., SKB-F) were grown to 80-90% confluence at 37° C. and 5% $CO_2$ in growth media (SKB-M; ZenBio, Inc.). Differentiation was initiated by replacing the growth media with differentiation media (SKM-D; ZenBio, Inc.). To assay exon 52 skipping, $1 \times 10^4$ differentiated cells were plated in a 24-well plate and 1 mL of differentiation media (SKM-D; ZenBio, Inc.) containing various concentrations of PMO or PPMO was added to each well and incubated for 96 hours.
Western Blot Analysis For western blot analysis, tissue was homogenized with homogenization buffer (4% SDS, 4 M urea, 125 mM tris-HCl (pH 6.8)) at a ratio of 9 to 18×20-µm tissue sections at approximately 5 mm in diameter in 133 µL of buffer. The corresponding lysate was collected and subjected to protein quantification using the RC DC Protein Assay Kit per manufacturer's instructions (BioRad Cat. 500-0122). The tissue extract samples were diluted 1:10 using homogenization buffer to fall within the range of the BSA standard curve. Samples were prepared such that 35 µl of sample would contain the desired amount of protein using 25 µl of protein lysate, 7 µl NuPAGE LDS Sample Buffer (Life Technologies Cat. NP0008, Carlsbad, Calif., USA), and 3 µl NuPAGE Reducing Agent (10×) (Life Technologies Cat. NP0004). After heating the protein samples for 5 minutes at 95° C., samples were centrifuged and supernatant was loaded onto a NuPAGE Novex 10 well, 1 mm, mini 3-8% polyacrylamide tris-acetate gel (Life Technologies Cat. EA0375) at a maximum of 50 µg total protein load per lane. The gel was run at 150 volts at room temperature until the dye front had run off the gel. The resulting protein gels were transferred to PVDF membranes (Life Technologies Cat. LC2007) for 75 minutes at room temperature with 30 volts using NuPAGE transfer buffer (Life Technologies NP006-1), 10% methanol and 0.1% NuPAGE antioxidant (Life Technologies NP0005).

After protein transfer, the PVDF membranes were immersed in TTBS buffer (1×TBS (Amresco Cat. J640-4L), 0.1% (v/v) tween-20). The membranes were transferred to blocking buffer (5% (w/v) non-fat dry milk (Lab Scientific Cat. M0841) in TTBS) and soaked overnight at 4° C. with gentle rocking. After blocking, the membranes were incubated for either 60 minutes at room temperature in DYS1 (Leica Cat. NCL-DYS1) diluted 1:20 using blocking buffer, or 20 minutes at room temperature in anti-α-actinin antibody (Sigma-Aldrich Cat. NA931V) diluted 1:100,000 with blocking buffer, followed by six washes (five minutes each with TTBS). Anti-mouse IgG conjugated to horseradish peroxidase (GE Healthcare Cat. NA931V) was diluted 1:40,000 using blocking buffer and added to the membranes for 45 minutes (DYS1) or 15 minutes (α-actinin), followed again by six washes. Using the ECL Prime Western Detection Kit (GE Healthcare Cat. RPN2232), film was exposed to the gel and developed accordingly. Developed film was scanned and analyzed using ImageQuant TL Plus software (version 8.1) and linear regression analysis was performed using Graphpad software.

Figure 5B:
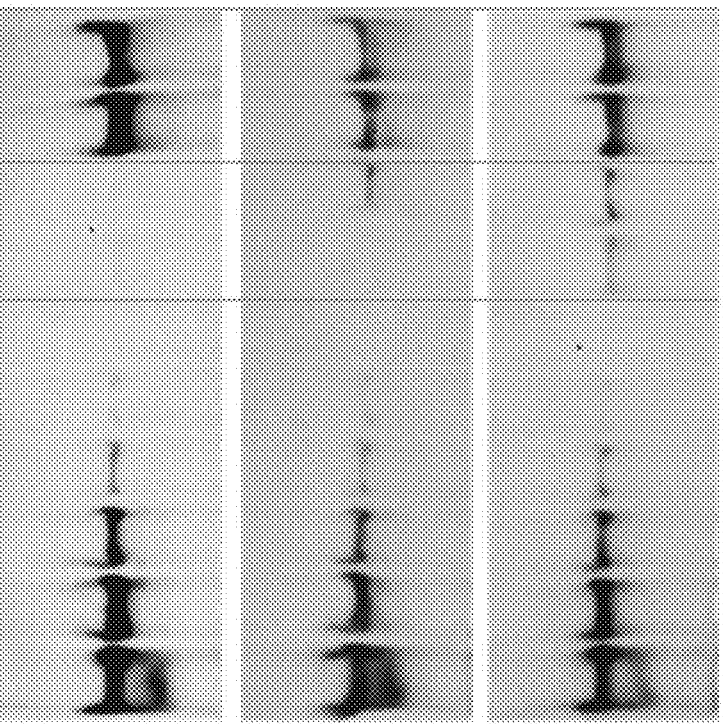
Figure 5A:
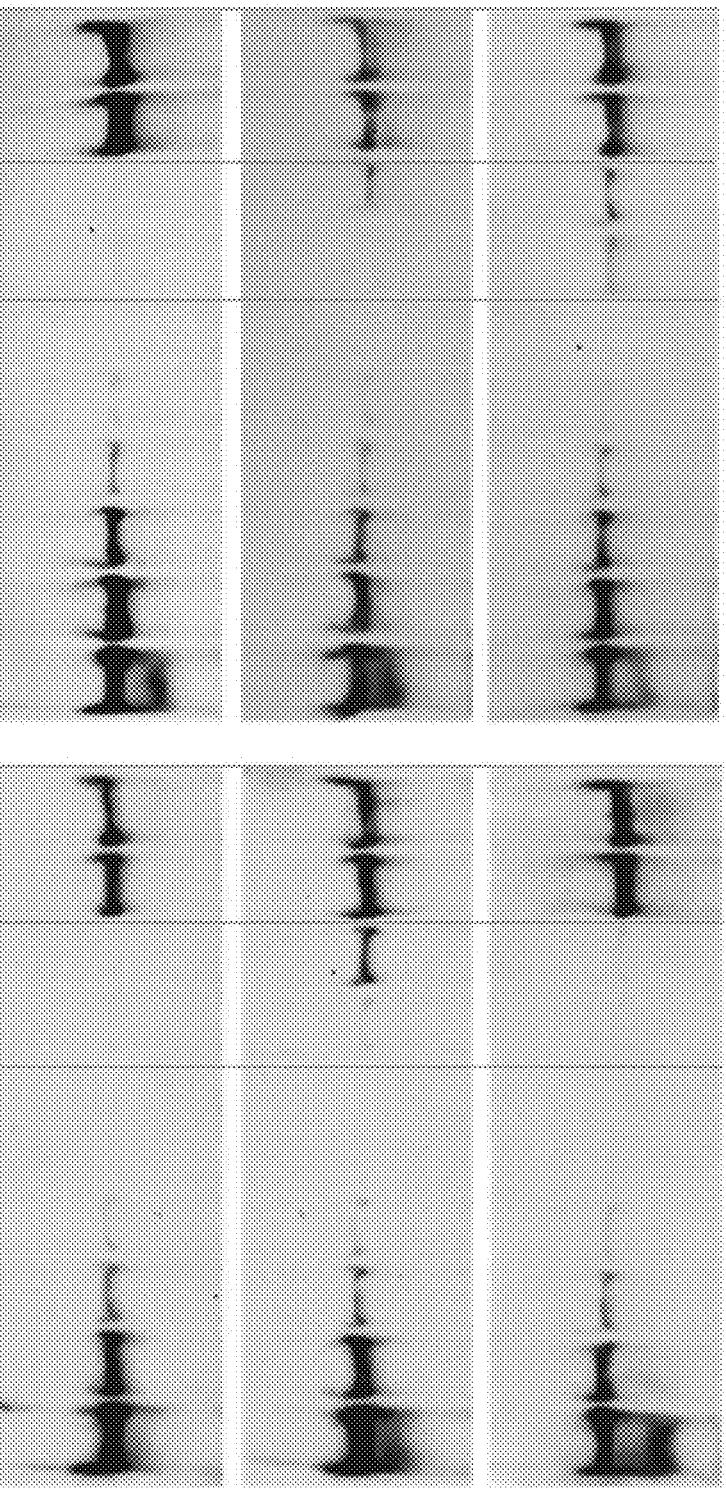
Figure 6A:
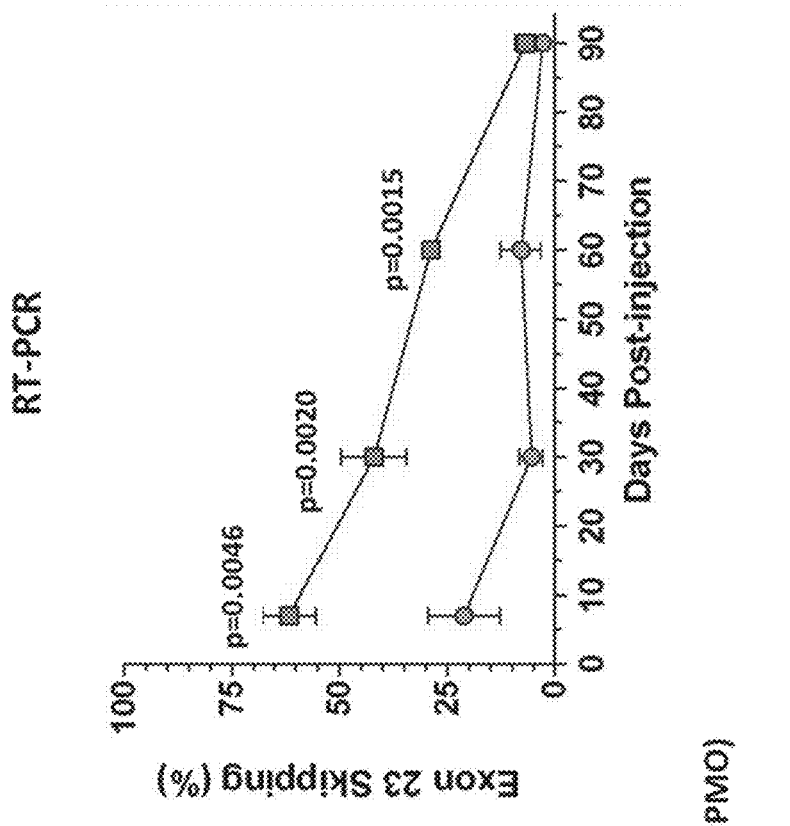
FIG. 6A provides a line graph depicting the percentage of wild-type dystrophin induced by PMO (PMO 4225) or PPMO (PPMO4225) in the quadriceps of mdx mice over 90 days post-injection, as determined by Western Blot analysis.
Figure 6B:
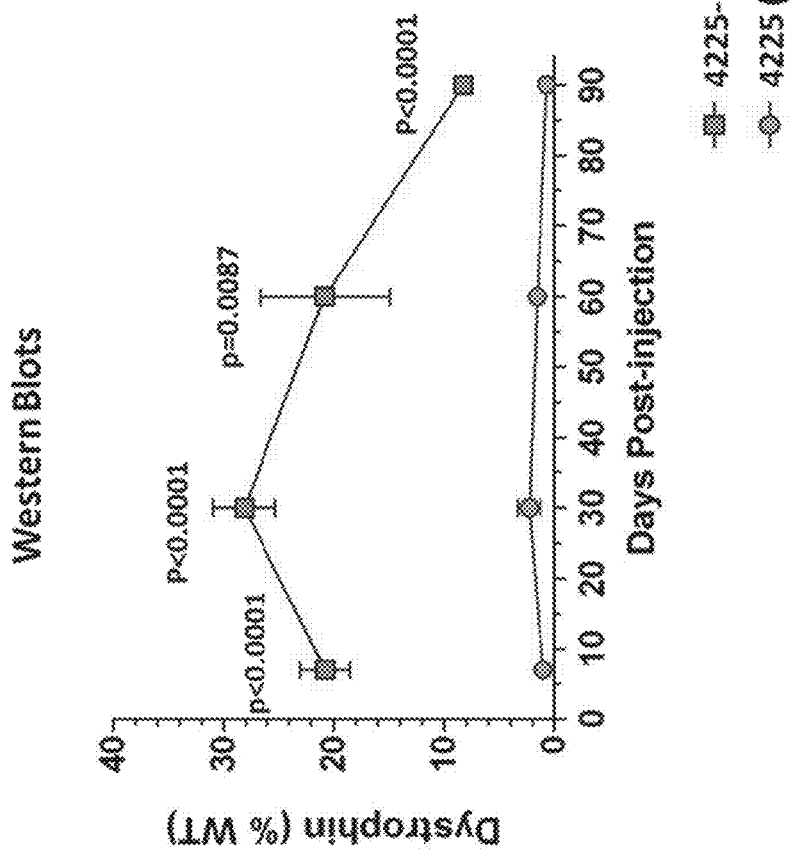
FIG. 6B provides a line graph depicting the percentage of exon 23 skipping induced by PMO (PMO 4225) or PPMO (PPMO4225) in the quadriceps of mdx mice over 90 days post-injection, as determined by RT-PCR.

Each Western blot gel includes a 4 or 5 point dystrophin standard curve prepared using total protein extracted from normal tissue (mouse quadriceps, diaphragm, or heart) diluted to, for example, 64%, 16%, 4%, 1%, and 0.25% (see. For example. FIGS. 5A and 5B) and spiked into DMD tissue (for example, mdx mouse quadriceps, diaphragm, or heart, or NHP quadriceps, diaphragm, or smooth muscle (GI)) extract. Standard curve samples were processed as described above. Dystrophin protein levels as percent of wild-type dystrophin levels (% WT) were determined by comparing dystrophin band intensities to the gel standard curve.

RT-PCR Analysis

For RT-PCR analysis, RNA was isolated from the cells using the Illustra GE spin kit following the manufacture's protocol. Exon 52 skipping was measured by RT-PCR with a forward primer that binds exon 50 SEQ ID NO: 5 (5'-CTCTGAGTGGAAGGCGGTAA-3') and a reverse primer that binds exon 53 SEQ ID NO: 6 (5'-ACCTGCTCAGCTTCTTCCTT-3'). Mouse exon 23 skipping was measured by RT-PCR with a forward primer-SEQ ID NO: 7 (5'-CACATCTTTGATGGTGTGAGG-3') and a reverse primer SEQ ID NO: 8 (5'-CAACTTCAGCCATC-CATTTCTG-3').

After the RNA was subjected to RT-PCR, the samples were analyzed using a Caliper machine, which uses gel capillary electrophoresis. Percent exon skipping was calculated using the following equation: (area under the curve for skipped bands)/(sum of area under curve for skipped and unskipped bands)×100.

Immunohistochemistry: Dystrophin Staining:

10 micron frozen tissue sections of the mouse quadriceps were used to detect dystrophin by dystrophin primary antibody (dilution 1:250, rabbit, Abcam, cat #ab15277) in 10% goat serum+1% BSA in PBS and secondary antibody Alexa-Fluoro 488 goat anti-rabbit (dilution of 1:1000) in 10% goat serum+1% BSA.

Preparation of Morpholino Subunits

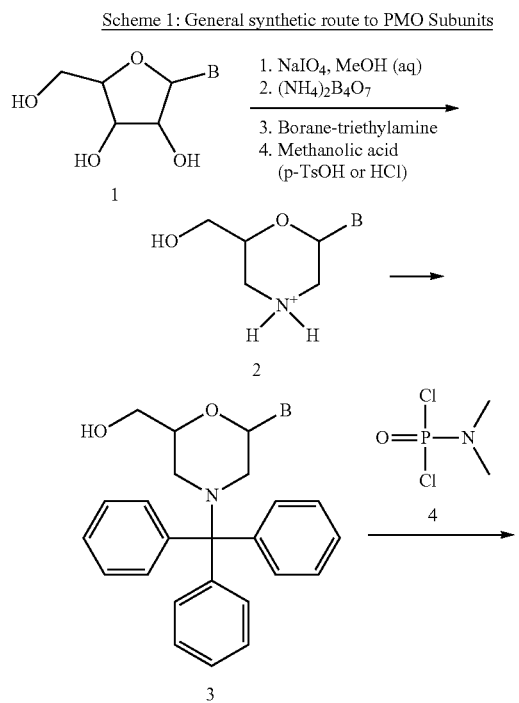

Scheme 1: General synthetic route to PMO Subunits

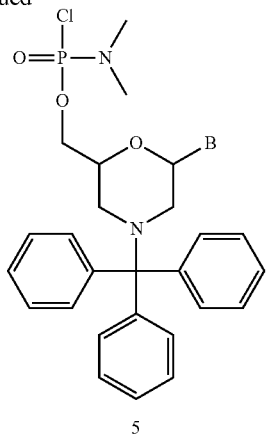

5

Referring to Scheme 1, wherein B represents a base pairing moiety, the morpholino subunits may be prepared from the corresponding ribinucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for solid-phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in U.S. Pat. No. 8,076,476, which is hereby incorporated by reference in its entirety.

Reaction of 3 with the activated phosphorous compound 4 results in morpholino subunits having the desired linkage moiety 5.

Compounds of structure 4 can be prepared using any number of methods known to those of skill in the art. Coupling with the morpholino moiety then proceeds as outlined above.

Compounds of structure 5 can be used in solid-phase oligomer synthesis for preparation of oligomers comprising the intersubunit linkages. Such methods are well known in the art. Briefly, a compound of structure 5 may be modified at the 5' end to contain a linker to a solid support. Once supported, the protecting group of 5 (e.g., trityl at 3'-end)) is removed and the free amine is reacted with an activated phosphorous moiety of a second compound of structure 5. This sequence is repeated until the desired length oligo is obtained. The protecting group in the terminal 3' end may either be removed or left on if a 3' modification is desired. The oligo can be removed from the solid support using any number of methods, or example treatment with a base to cleave the linkage to the solid support.

The preparation of morpholino oligomers in general and specific morpholino oligomers of the disclosure are described in more detail in the Examples.

Preparation of Morpholino Oligomers

The preparation of the compounds of the disclosure are performed using the following protocol according to Scheme 2:

Scheme 2: Preparation of Activated Tail Acid

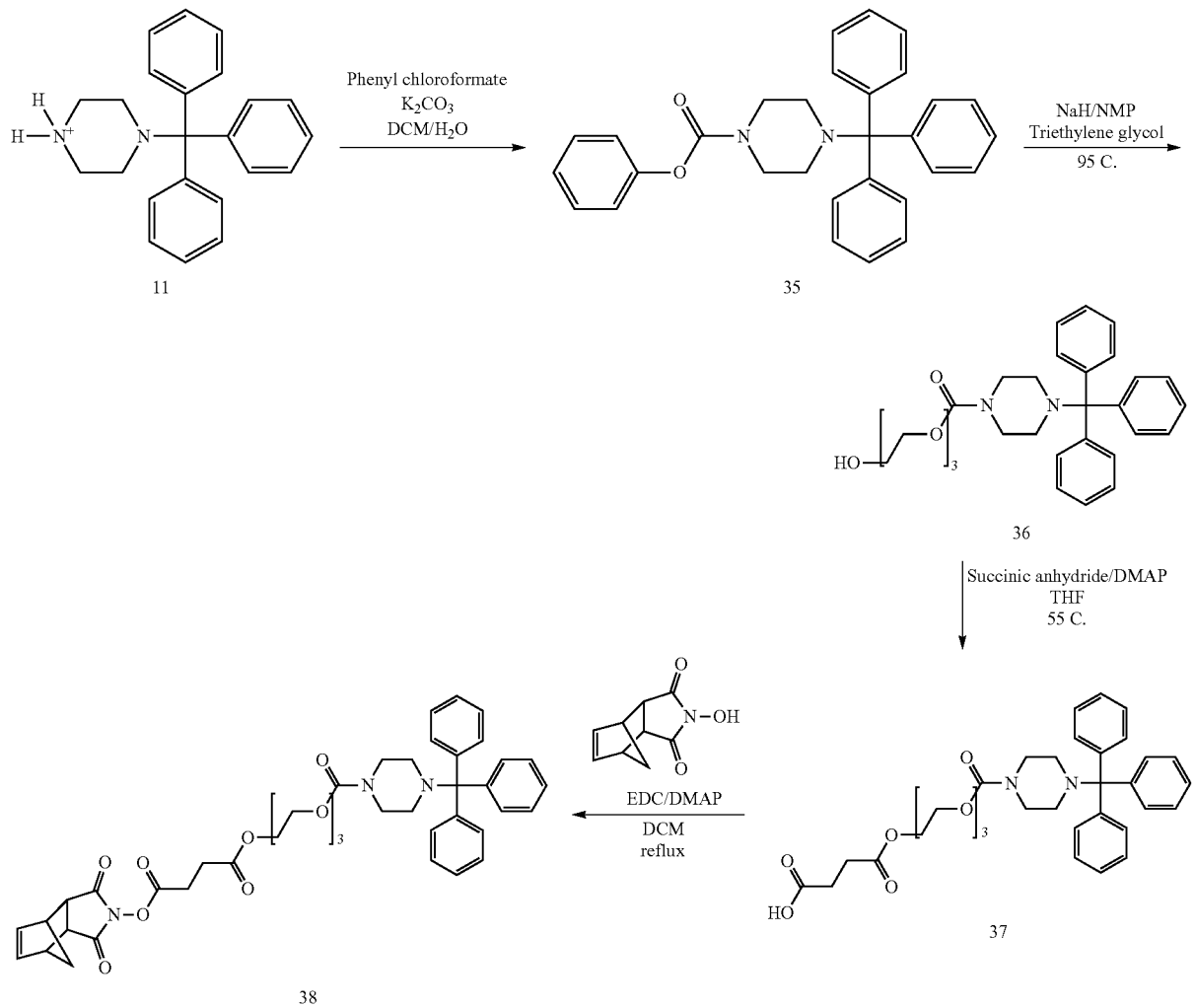

Preparation of trityl piperazine phenyl carbamate 35: To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile.

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts.

PMO Synthesis Method A: Use of Disulfide Anchor

Introduction of the activated "Tail" onto the anchor-loaded resin was performed in dimethyl imidazolidinone (DMI) by the procedure used for incorporation of the subunits during solid phase synthesis.

The resin treatment/wash steps in the following procedure consist of two basic operations: resin fluidization or stirrer bed reactor and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow

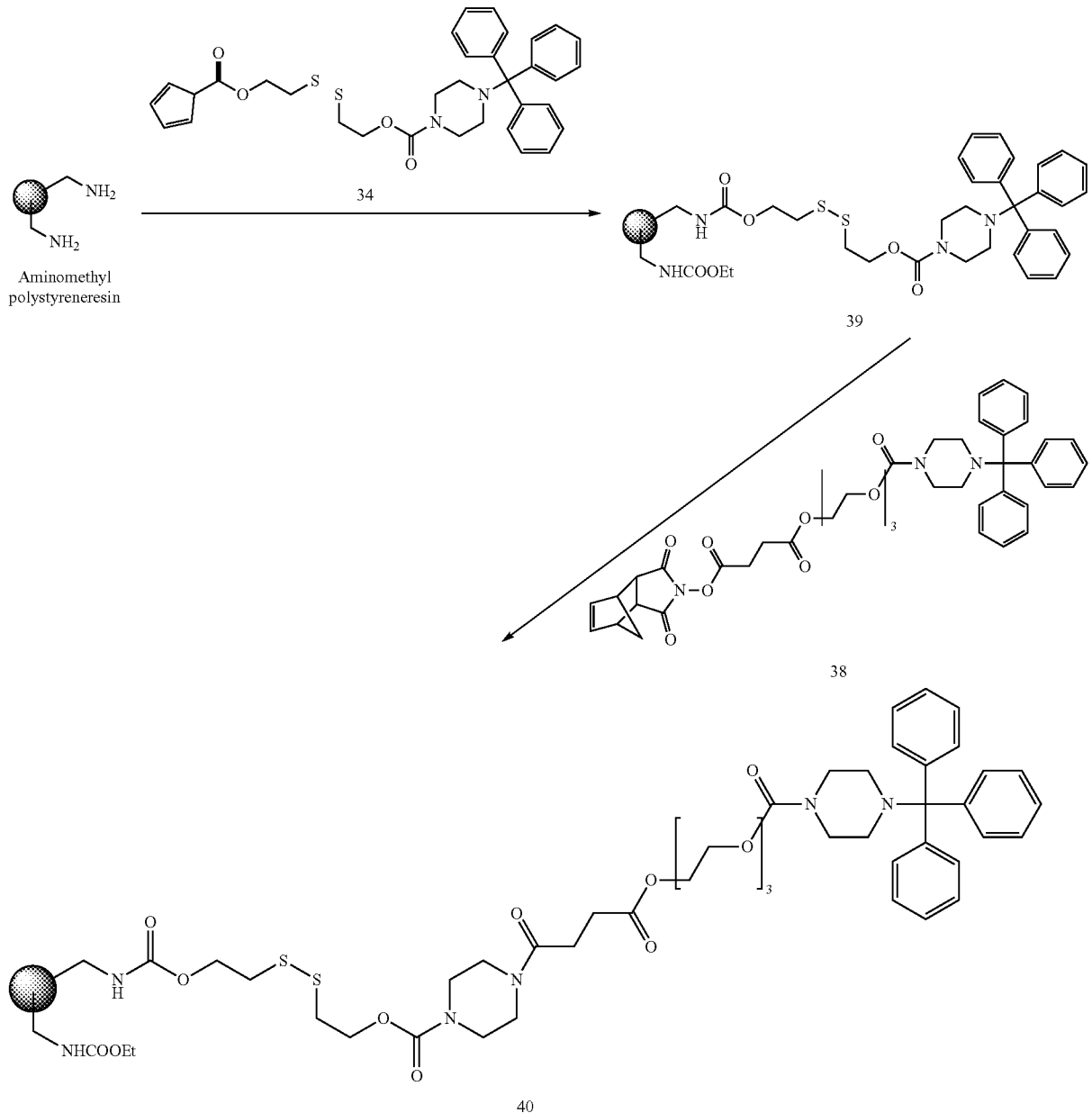

This procedure was performed in a silanized, jacketed peptide vessel (ChemGlass, NJ, USA) with a coarse porosity (40-60 μm) glass frit, overhead stirrer, and 3-way Teflon stopcock to allow N2 to bubble up through the frit or a vacuum extraction.

evacuation of resin treatment/wash to waste. All resin treatment/wash volumes were 15 mL/g of resin unless noted otherwise.

To aminomethylpolystyrene resin (100-200 mesh; ~1.0 mmol/g load based on nitrogen substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was treated with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 was dried under a N2 stream for 1-3 hr and then under vacuum to constant weight (2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into solid support. The anchor loaded resin was first deprotected under acidic condition and the resulting material neutralized before coupling. For the coupling step, a solution of 38 (0.2 M) in DMI containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:

Detritylation Solution: 10% Cyanoacetic Acid (w/v) in 4:1 dichloromethane/acetonitrile;

Neutralization Solution: 5% Diisopropylethylamine in 3:1 dichloromethane/isopropanol; and Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone.

Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
| --- | --- | --- | --- |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone.

One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc. aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Crude product purification: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M $H_3PO_4$ to lower the pH to 2.5. After initial mixing, the samples sat at room temperature for 4 min, at which time they are neutralized to pH 10-11 with 2.8% ammonia/water. The products were purified by solid phase extraction (SPE).

SPE column packing and conditioning: Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% $NH_4OH$/80% acetonitrile; 0.5 M NaOH/20% ethanol; water; 50 mM $H_3PO_4$/80% acetonitrile; water; 0.5 NaOH/20% ethanol; water; 0.28% $NH_4OH$.

SPE purification: The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia.

Product isolation: The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers by MALDI: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

PMO Synthesis Method B: Use of NCP2 Anchor
NCP2 Anchor Synthesis:

1. Preparation of Methyl 4-Fluoro-3-Nitrobenzoate (1)

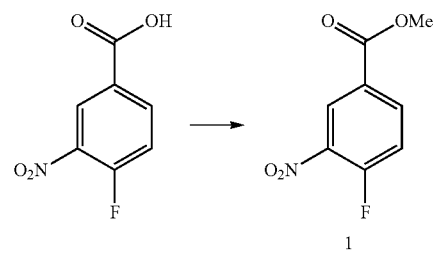 [SMILES: O=C(O)c1ccc(F)c([N+](=O)[O-])c1 ; COC(=O)c1ccc(F)c([N+](=O)[O-])c1]

To a 100 L flask was charged 12.7 kg of 4-fluoro-3-nitrobenzoic acid was added 40 kg of methanol and 2.82 kg concentrated sulfuric acid. The mixture was stirred at reflux (65° C.) for 36 hours. The reaction mixture was cooled to 0° C. Crystals formed at 38° C. The mixture was held at 0° C. for 4 hrs then filtered under nitrogen. The 100 L flask was washed and filter cake was washed with 10 kg of methanol that had been cooled to 0° C. The solid filter cake was dried on the funnel for 1 hour, transferred to trays, and dried in a vacuum oven at room temperature to a constant weight of 13.695 kg methyl 4-fluoro-3-nitrobenzoate (100% yield; HPLC 99%).

2. Preparation of 3-Nitro-4-(2-oxopropyl)benzoic Acid

A. (Z)-Methyl 4-(3-Hydroxy-1-Methoxy-1-Oxobut-2-en-2-yl)-3-Nitrobenzoate (2)

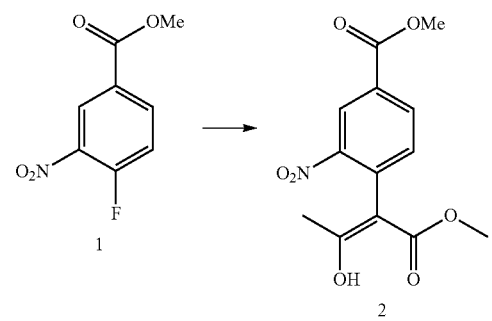 [SMILES: COC(=O)c1ccc(F)c([N+](=O)[O-])c1 ; COC(=O)/C(=C(/C)O)c1ccc(C(=O)OC)cc1[N+](=O)[O-]]

To a 100 L flask was charged 3.98 kg of methyl 4-fluoro-3-nitrobenzoate (1) from the previous step 9.8 kg DMF, 2.81 kg methyl acetoacetate. The mixture was stirred and cooled to 0° C. To this was added 3.66 kg DBU over about 4 hours while the temperature was maintained at or below 5° C. The mixture was stirred an additional 1 hour. To the reaction flask was added a solution of 8.15 kg of citric acid in 37.5 kg of purified water while the reaction temperature was maintained at or below 15° C. After the addition, the reaction mixture was stirred an addition 30 minutes then filtered under nitrogen. The wet filter cake was returned to the 100 L flask along with 14.8 kg of purified water. The slurry was stirred for 10 minutes then filtered. The wet cake was again returned to the 100 L flask, slurried with 14.8 kg of purified water for 10 minutes, and filtered to crude (Z)-methyl 4-(3-hydroxy-1-methoxy-1-oxobut-2-en-2-yl)-3-nitrobenzoate.

B. 3-Nitro-4-(2-oxopropyl)benzoic Acid

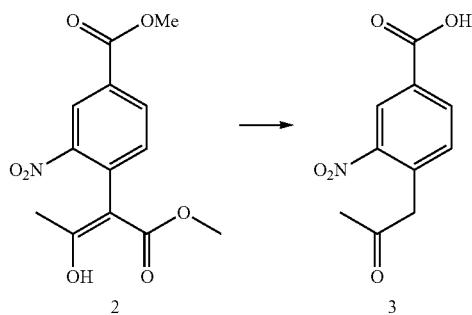 [SMILES: COC(=O)/C(=C(/C)O)c1ccc(C(=O)OC)cc1[N+](=O)[O-] ; CC(=O)Cc1ccc(C(=O)O)cc1[N+](=O)[O-]]

The crude (Z)-methyl 4-(3-hydroxy-1-methoxy-1-oxobut-2-en-2-yl)-3-nitrobenzoate was charged to a 100 L reaction flask under nitrogen. To this was added 14.2 kg 1,4-dioxane and the stirred. To the mixture was added a solution of 16.655 kg concentrated HCl and 13.33 kg purified water (6 M HCl) over 2 hours while the temperature of the reaction mixture was maintained below 15° C. When the addition was complete, the reaction mixture was heated at reflux (80° C.) for 24 hours, cooled to room temperature, and filtered under nitrogen. The solid filter cake was triturated with 14.8 kg of purified water, filtered, triturated again with 14.8 kg of purified water, and filtered. The solid was returned to the 100 L flask with 39.9 kg of DCM and refluxed with stirring for 1 hour. 1.5 kg of purified water was added to dissolve the remaining solids. The bottom organic layer was split to a pre-warmed 72 L flask, then returned to a clean dry 100 L flask. The solution was cooled to 0° C., held for 1 hour, then filtered. The solid filter cake was washed twice each with a solution of 9.8 kg DCM and 5 kg heptane, then dried on the funnel. The solid was transferred to trays and dried to a constant weight of 1.855 kg 3-Nitro-4-(2-oxopropyl)benzoic Acid. Overall yield 42% from compound 1. HPLC 99.45%.

3. Preparation of N-Tritylpiperazine Succinate (NTP)

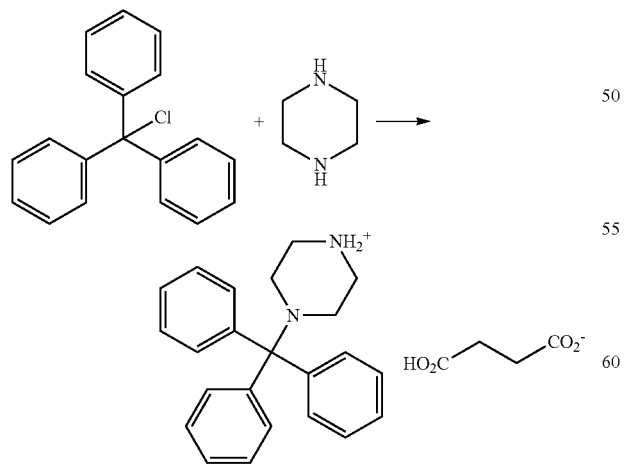

To a 72 L jacketed flask was charged under nitrogen 1.805 kg triphenylmethyl chloride and 8.3 kg of toluene (TPC solution). The mixture was stirred until the solids dissolved. To a 100 L jacketed reaction flask was added under nitrogen 5.61 kg piperazine, 19.9 kg toluene, and 3.72 kg methanol. The mixture was stirred and cooled to 0° C. To this was slowly added in portions the TPC solution over 4 hours while the reaction temperature was maintained at or below 10° C. The mixture was stirred for 1.5 hours at 10° C., then allowed to warm to 14° C. 32.6 kg of purified water was charged to the 72 L flask, then transferred to the 100 L flask while the internal batch temperature was maintained at 20 +/−5° C. The layers were allowed to split and the bottom aqueous layer was separated and stored. The organic layer was extracted three times with 32 kg of purified water each, and the aqueous layers were separated and combined with the stored aqueous solution.

The remaining organic layer was cooled to 18° C. and a solution of 847 g of succinic acid in 10.87 kg of purified water was added slowly in portions to the organic layer. The mixture was stirred for 1.75 hours at 20+/−5° C. The mixture was filtered, and the solids were washed with 2 kg TBME and 2 kg of acetone then dried on the funnel. The filter cake was triturated twice with 5.7 kg each of acetone and filtered and washed with 1 kg of acetone between triturations. The solid was dried on the funnel, then transferred to trays and dried in a vacuum oven at room temperature to a constant weight of 2.32 kg of NTP. Yield 80%.

4. Preparation of (4-(2-Hydroxypropyl)-3-Nitrophenyl)(4-Tritylpiperazin-1-yl)Methanone

A. Preparation of 1-(2-Nitro-4(4-Tritylpiperazine-1-Carbonyl)Phenyl)Propan-2-one

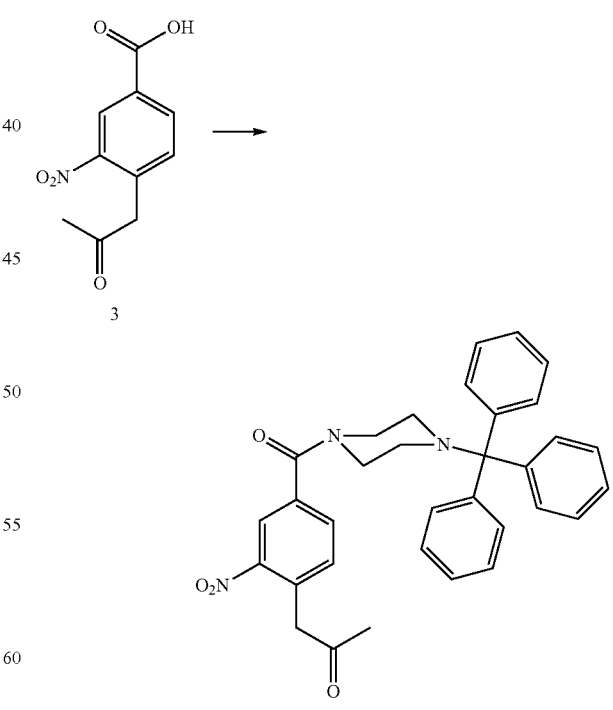

To a 100 L jacketed flask was charged under nitrogen 2 kg of 3-Nitro-4-(2-oxopropyl)benzoic Acid (3), 18.3 kg DCM, and 1.845 kg N-(3-dimethylaminopropyl)-N'-ethylcarbodiimide hydrochloride (EDC.HCl). The solution was stirred until a homogenous mixture was formed. 3.048 kg of NTP was added over 30 minutes at room temperature and stirred for 8 hours. 5.44 kg of purified water was added to the reaction mixture and stirred for 30 minutes. The layers were allowed to separate and the bottom organic layer containing the product was drained and stored. The aqueous layer was extracted twice with 5.65 kg of DCM. The combined organic layers were washed with a solution of 1.08 kg sodium chloride in 4.08 kg purified water. The organic layers were dried over 1.068 kg of sodium sulfate and filtered. The sodium sulfate was washed with 1.3 kg of DCM. The combined organic layers were slurried with 252 g of silica gel and filtered through a filter funnel containing a bed of 252 g of silica gel. The silica gel bed was washed with 2 kg of DCM. The combined organic layers were evaporated on a rotovap. 4.8 kg of THF was added to the residue and then evaporated on the rotovap until 2.5 volumes of the crude 1-(2-nitro-4(4-tritylpiperazine-1-carbonyl)phenyl)propan-2-one in THF was reached.

B. Preparation of (4-(2-Hydroxypropyl)-3-Nitrophenyl)(4-Tritylpiperazin-1-yl)Methanone (5)

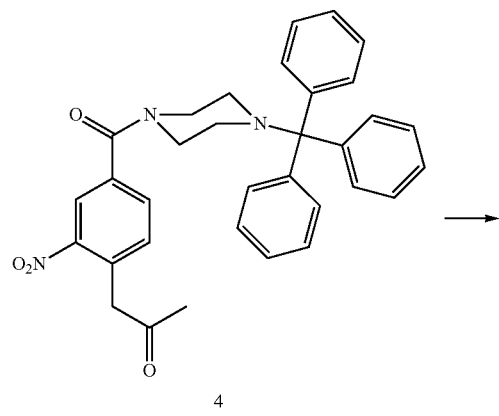

4

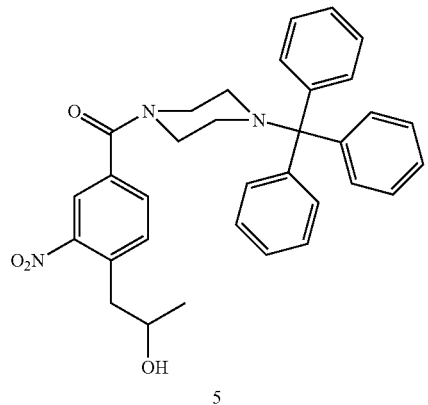

5

To a 100 L jacketed flask was charged under nitrogen 3600 g of 4 from the previous step and 9800 g THF. The stirred solution was cooled to <5° C. The solution was diluted with 11525 g ethanol and 194 g of sodium borohydride was added over about 2 hours at <5° C. The reaction mixture was stirred an additional 2 hours at <5° C. The reaction was quenched with a solution of about 1.1 kg ammonium chloride in about 3 kg of water by slow addition to maintain the temperature at <10° C. The reaction mixture was stirred an additional 30 minutes, filtered to remove inorganics, and recharged to a 100 L jacketed flask and extracted with 23 kg of DCM. The organic layer was separated and the aqueous was twice more extracted with 4.7 kg of DCM each. The combined organic layers were washed with a solution of about 800 g of sodium chloride in about 3 kg of water, then dried over 2.7 kg of sodium sulfate. The suspension was filtered and the filter cake was washed with 2 kg of DCM. The combined filtrates were concentrated to 2.0 volumes, diluted with about 360 g of ethyl acetate, and evaporated. The crude product was loaded onto a silica gel column of 4 kg of silica packed with DCM under nitrogen and eluted with 2.3 kg ethyl acetate in 7.2 kg of DCM. The combined fractions were evaporated and the residue was taken up in 11.7 kg of toluene. The toluene solution was filtered and the filter cake was washed twice with 2 kg of toluene each. The filter cake was dried to a constant weight of 2.275 kg of compound 5 (46% yield from compound 3) HPLC 96.99%.

5. Preparation of 2,5-Dioxopyrrolidin-1-yl(1-(2-Nitro-4-(4-triphenylmethylpiperazine-1 Carbonyl) Phenyl)Propan-2-yl) Carbonate (NCP2 Anchor)

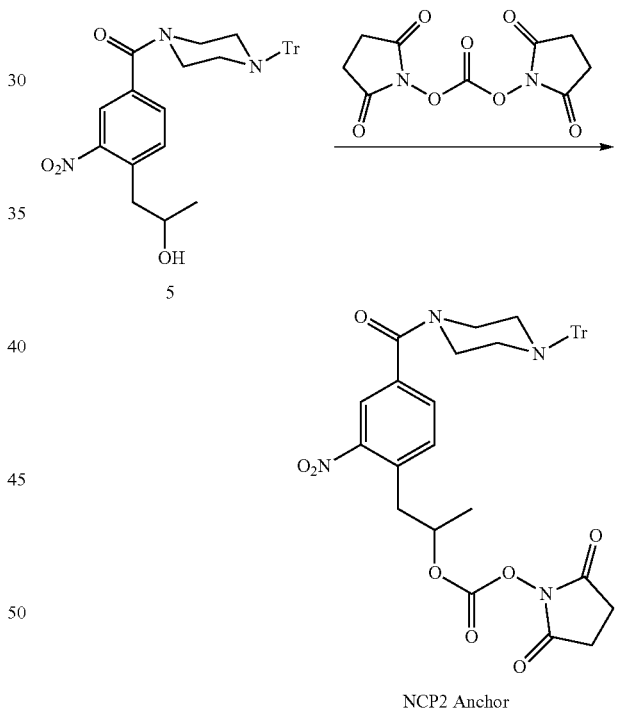

NCP2 Anchor

To a 100 L jacketed flask was charged under nitrogen 4.3 kg of compound 5 (weight adjusted based on residual toluene by $H^1$ NMR; all reagents here after were scaled accordingly) and 12.7 kg pyridine. To this was charged 3.160 kg of DSC (78.91 weight % by $H^1$ NMR) while the internal temperature was maintained at <35° C. The reaction mixture was aged for about 22 hours at ambience then filtered. The filter cake was washed with 200 g of pyridine. In two batches each comprising ½ the filtrate volume, filtrate wash charged slowly to a 100 L jacketed flask containing a solution of about 11 kg of citric acid in about 50 kg of water and stirred for 30 minutes to allow for solid precipitation. The solid was collected with a filter funnel, washed twice with 4.3 kg of water per wash, and dried on the filter funnel under vacuum.

The combined solids were charged to a 100 L jacketed flask and dissolved in 28 kg of DCM and washed with a solution of 900 g of potassium carbonate in 4.3 kg of water. After 1 hour, the layers were allowed to separate and the aqueous layer was removed. The organic layer was washed with 10 kg of water, separated, and dried over 3.5 kg of sodium sulfate. The DCM was filtered, evaporated, and dried under vacuum to 6.16 kg of NCP2 Anchor (114% yield).

NCP2 Anchor Loaded Resin Synthesis

To a 75 L solid phase synthesis reactor with a Teflon stop cock was charged about 52 L of NMP and 2300 g of aminomethyl polystyrene resin. The resin was stirred in the NMP to swell for about 2 hours then drained. The resin was washed twice with about 4 L DCM per wash, then twice with 39 L Neutralization Solution per wash, then twice with 39 L of DCM per wash. The NCP2 Anchor Solution was slowly added to the stirring resin solution, stirred for 24 hours at room temperature, and drained. The resin was washed four times with 39 L of NMP per wash, and six times with 39 L of DCM per wash. The resin was treated and stirred with ½ the DEDC Capping Solution for 30 minutes, drained, and was treated and stirred with the $2^{nd}$ ½ of the DEDC Capping Solution for 30 minutes and drained. The resin was washed six times with 39 L of DCM per wash then dried in an oven to constant weight of 3573.71 g of Anchor Loaded Resin.

Preparation of Morpholino Oligomer using NCP2 Anchor

Representative Example of a 50 L Solid-phase Synthesis of a PMO, Golodirsen (PMO-G; SEQ ID NO: 9), Crude Drug Substance 1. Materials

TABLE 2

Starting Materials

| Material Name | Chemical Name | CAS Number | Chemical Formula | Molecular Weight |
|---|---|---|---|---|
| Activated A Subunit | Phosphoramidochloridic acid, N,N-dimethyl-,[6-[6-(benzoylamino)-9H-purin-9-yl]-4-(triphenylmethyl)-2-morpholinyl]methyl ester | 1155373-30-0 | $C_{38}H_{37}ClN_7O_4P$ | 722.2 |
| Activated C Subunit | Phosphoramidochloridic acid, N,N-dimethyl-,[6-[4-(benzoylamino)-2-oxo-1(2H)-pyrimidinyl]-4-(triphenylmethyl)-2-morpholinyl]methyl ester | 1155373-31-1 | $C_{37}H_{37}ClN_5O_5P$ | 698.2 |
| Activated DPG Subunit | Propanoic Acid, 2,2-dimethyl-,4-[[[9-[6-[[[chloro(dimethylamino)phosphinyl]oxy]methyl]-4-(triphenylmethyl)-2-morpholinyl]-2-[(2-phenylacetyl)amino]-9H-purin-6-yl]oxy]methyl]phenyl ester | 1155309-89-9 | $C_{51}H_{53}ClN_7O_7P$ | 942.2 |
| Activated T Subunit | Phosphoramidochloridic acid, N,N-dimethyl-,[6-(3,4-dihydro-5-methyl-2,4-dioxo-1(2H)-pyrimidinyl)]-4-(triphenylmethyl)-2-morpholinyl]methyl ester | 1155373-34-4 | $C_{31}H_{34}ClN_4O_5P$ | 609.1 |
| Activated EG3 Tail | Butanedioic acid, 1-[3aR,4S,7R,7aS)-1,3,3a,4,7,7a-hexahydro-1,3-dioxo-4,7-methano-2H-isoindol-2-yl] 4-[2-[2-[2-[[[4-(triphenylmethyl)-1-piperazinyl]carbonyl]oxy]ethoxy]ethoxy]ethyl] ester | 1380600-06-5 | $C_{43}H_{47}N_3O_{10}$ | 765.9 |

Chemical Structures of Starting Materials:
A. Activated EG3 Tail
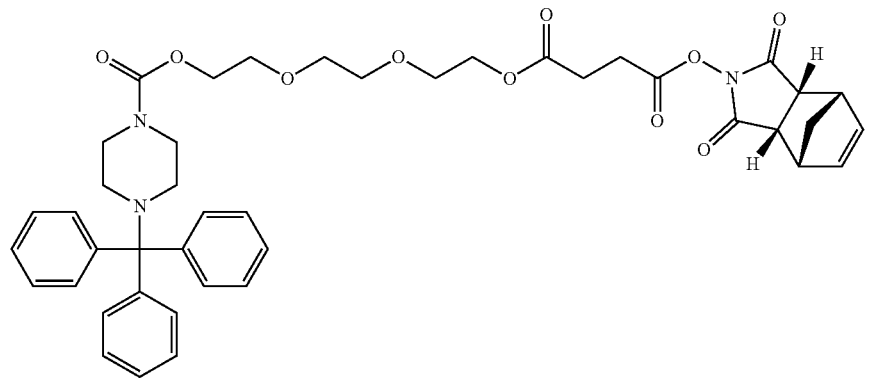 [SMILES: O=C(CCC(=O)ON1C(=O)[C@@H]2[C@H](C1=O)[C@@H]1C=C[C@H]2C1)OCCOCCOCCOC(=O)N1CCN(C(c2ccccc2)(c2ccccc2)c2ccccc2)CC1]
B. Activated C Subunit (For preparation, see U.S. Pat. No. 8,067,571)
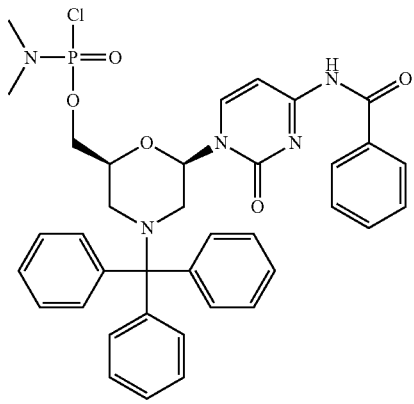 [SMILES: CN(C)P(=O)(Cl)OC[C@@H]1CN(C(c2ccccc2)(c2ccccc2)c2ccccc2)C[C@H](n2ccc(NC(=O)c3ccccc3)nc2=O)O1]
C. Activated A Subunit (For preparation, see U.S. Pat. No. 8,067,571)
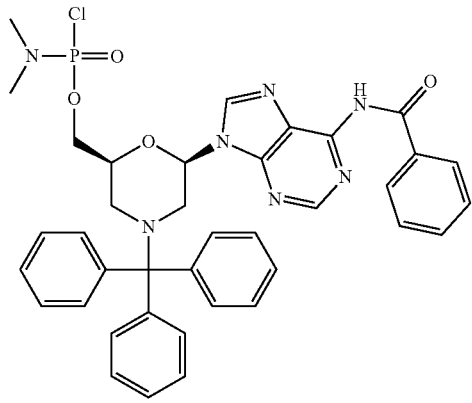 [SMILES: CN(C)P(=O)(Cl)OC[C@@H]1CN(C(c2ccccc2)(c2ccccc2)c2ccccc2)C[C@H](n2cnc3c(NC(=O)c4ccccc4)ncnc32)O1]
D. Activated DPG Subunit (For preparation, see WO 2009/064471)
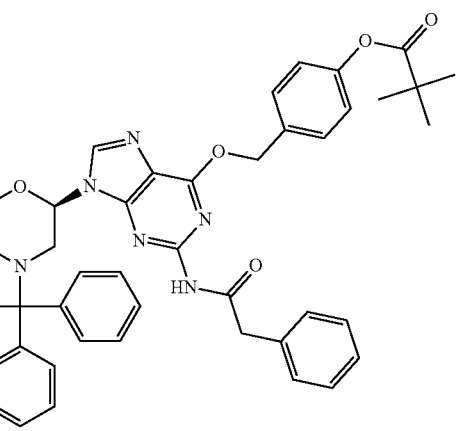
E. Activated T Subunit (For preparation, see WO 2013/082551)
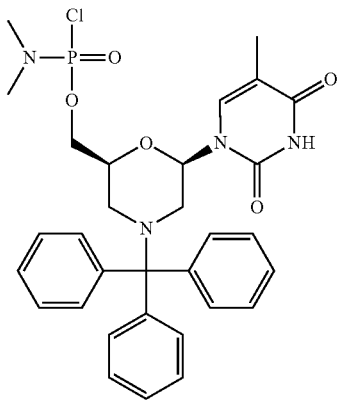 [SMILES: Cc1cn([C@H]2CN(C(c3ccccc3)(c3ccccc3)c3ccccc3)C[C@@H](COP(=O)(Cl)N(C)C)O2)c(=O)[nH]c1=O]

F. Anchor Loaded Resin

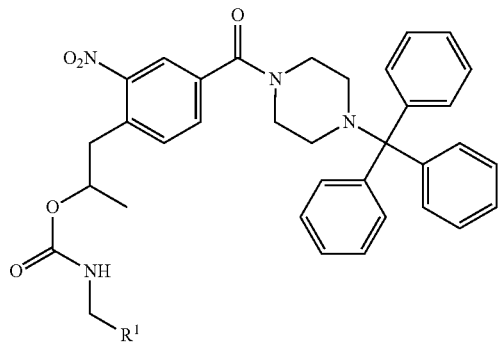

wherein R¹ is a support-medium.

TABLE 3

Description of Solutions for Solid Phase Oligomer Synthesis of Golodirsen Crude Drug Substance

| Solution Name | Solution Composition |
|---|---|
| NCP2 Anchor Solution | 37.5 L NMP and 1292 g NCP2 Anchor |
| DEDC Capping Solution | 4.16 L Diethyl Dicarbonate (DEDC), 3.64 L NEM, and 33.8 L DCM |
| CYTFA Solution | 2.02 kg 4-cyanopyridine, 158 L DCM, 1.42 L TFA, 39 L TFE, and 2 L purified water |
| Neutralization Solution | 35.3 L IPA, 7.5 L DIPEA, and 106.5 L DCM |
| Cleavage Solution | 1,530.04 g DTT, 6.96 L NMP, and 2.98 L DBU |

2. Synthesis of Golodirsen Crude Drug Substance

A. Resin Swelling 750 g of Anchor Loaded Resin and 10.5 L of NMP were charged to a 50 L silanized reactor and stirred for 3 hours. The NMP was drained and the Anchor Loaded Resin was washed twice with 5.5 L each of DCM and twice with 5.5 L each of 30% TFE/DCM.

B. Cycle 0: EG3 Tail Coupling

The Anchor Loaded Resin was washed three times with 5.5 L each of 30% TFE/DCM and drained, washed with 5.5 L of CYFTA solution for 15 minutes and drained, and again washed with 5.5 L of CYTFA Solution for 15 minutes without draining to which 122 mL of 1:1 NEM/DCM was charged and the suspension stirred for 2 minutes and drained. The resin was washed twice with 5.5 L of Neutralization Solution for 5 minutes and drained, then twice with 5.5 L each of DCM and drained. A solution of 706.2 g of activated EG3 Tail (MW 765.85) and 234 mL of NEM in 3 L of DMI was charged to the resin and stirred for 3 hours at RT and drained. The resin was washed twice with 5.5 L each of Neutralization Solution for 5 minutes per each wash, and once with 5.5 L of DCM and drained. A solution of 374.8 g of benzoic anhydride and 195 mL NEM in 2680 mL NMP was charged and stirred for 15 minutes and drained. The resin was stirred with 5.5 L of Neutralization Solution for 5 minutes, then washed once with 5.5 L of DCM and twice with 5.5 L each of 30% TFE/DCM. The resin was suspended in 5.5 L of 30% TFE/DCM and held for 14 hours.

C. Subunit Coupling Cycles 1-30 i. Pre-Coupling Treatments

Prior to each coupling cycle as described in FIG. 18, the resin was: 1) washed with 30% TFE/DCM; 2) a) treated with CYTFA Solution 15 minutes and drained, and b) treated with CYTFA solution for 15 minutes to which was added 1:1 NEM/DCM, stirred, and drained; 3) stirred three times with Neutralization Solution; and 4) washed twice with DCM. See FIG. 18.

ii. Post Coupling Treatments

After each subunit solution was drained as described in FIG. 18, the resin was: 1) washed with DCM; and 2) washed two times with 30% TFE/DCM. If the resin was held for a time period prior to the next coupling cycle, the second TFE/DCM wash was not drained and the resin was retained in said TFE/DCM wash solution. See FIG. 18.

iii. Activated Subunit Coupling Cycles

The coupling cycles were performed as described in FIG. 18.

iv. Final IPA Washing

After the final coupling step was performed as described in FIG. 18, the resin was washed 8 times with 19.5 L each of IPA, and dried under vacuum at room temperature for about 63.5 hours to a dried weight of 4857.9 g.

C. Cleavage

The above resin bound Golodirsen Crude Drug Substance was divided into two lots, each lot was treated as follows. A 1619.3 g lot of resin was: 1) stirred with 10 L of NMP for 2 hrs, then the NMP was drained; 2) washed tree times with 10 L each of 30% TFE/DCM; 3) treated with 10 L CYTFA Solution for 15 minutes; and 4) 10 L of CYTFA Solution for 15 minutes to which 130 ml 1:1 NEM/DCM was then added and stirred for 2 minutes and drained. The resin was treated three times with 10 L each of Neutralization Solution, washed six times with 10 L of DCM, and eight times with 10 L each of NMP. The resin was treated with a Cleaving Solution of 1530.4 g DTT and 2980 DBU in 6.96 L NMP for 2 hours to detach the Eteplisen Crude Drug Substance from the resin. The Cleaving solution was drained and retained in a separate vessel. The reactor and resin were washed with 4.97 L of NMP which was combined with the Cleaving Solution.

D. Deprotection

The combined Cleaving Solution and NMP wash were transferred to a pressure vessel to which was added 39.8 L of $NH_4OH$ ($NH_3 \cdot H_2O$) that had been chilled to a temperature of −10° C. to −25° C. in a freezer. The pressure vessel was sealed and heated to 45° C. for 16 hrs then allowed to cool to 25° C. This deprotection solution containing the Golodirsen crude drug substance was diluted 3:1 with purified water and pH adjusted to 3.0 with 2 M phosphoric acid, then to pH 8.03 with $NH_4OH$. HPLC: C18 77.552% and SCX-10 73.768 0.

Purification of Golodirsen (PMO-G) Crude Drug Substance

The deprotection solution from above part D, containing the Golodirsen crude drug substance was loaded onto a column of ToyoPearl Super-Q 650S anion exchange resin (Tosoh Bioscience) and eluted with a gradient of 0-35% B over 17 column volume (Buffer A: 10 mM sodium hydroxide; Buffer B: 1 M sodium chloride in 10 mM sodium hydroxide) and fractions of acceptable purity (C18 and SCX HPLC) were pooled to a purified drug product solution. HPLC: 93.571% (C18) 88.270% (SCX).

The purified drug substance solution was desalted and lyophilized to 1450.72 g purified Golodirsen drug substance. Yield 54.56%; HPLC: 93.531% (C18) 88.354% (SCX).

TABLE 5

Acronyms

| Acronym | Name |
|---|---|
| DBU | 1,8-Diazabicycloundec-7-ene |
| DCM | Dichloromethane |
| DIPEA | N,N-Diisopropylethylamine |
| DMI | 1,3-Dimethyl-2-imidazolidinone |
| DTT | Dithiothreitol |
| IPA | Isopropyl alcohol |
| MW | Molecular weight |
| NEM | N-Ethylmorpholine |
| NMP | N-Methyl-2-pyrrolidone |
| RT | Room temperature |
| TFA | 2,2,2-Trifluoroacetic acid |
| TFE | 2,2,2-Trifluoroethanol |

Representative Example of CPP Conjugation

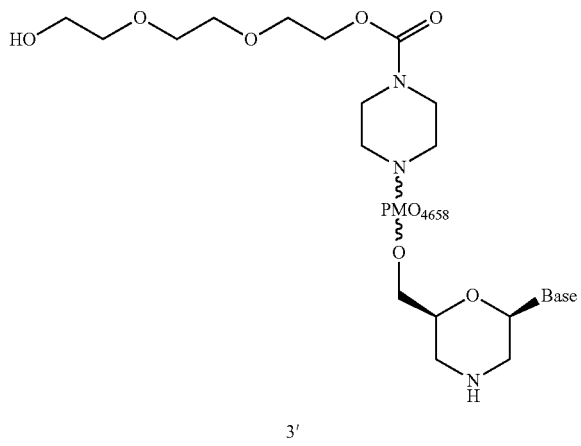

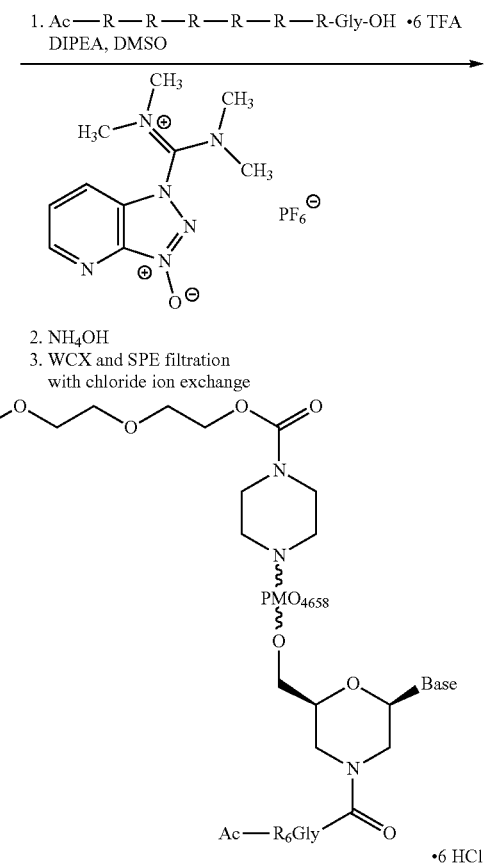

water containing 24 mM $H_3PO_4$) and B (25% acetonitrile in water containing 1 M KCl and 24 mM $H_3PO_4$). Gradient elution was employed: 0 min, 35% B; 2 min, 35% B; 22 min, 80% B; 25 min, 80% B; 25.1 min, 35% B; 30 min, 35% B.

To a mixture of the PMO 4658 (1.82 g, 0.177 mmol, freshly dried by lyophilization for two days; SEQ ID NO: 10), Ac-L-Arg-L-Arg-L-Arg-L-Arg-L-Arg-L-Arg-Gly-OH hexatrifluoroacetate (614.7 mg, 0.354 mmol), and 1-[Bis (dimethylamino)methylene]-1H-1,2,3-triazolo[4,5-b]pyridinium 3-oxid hexafluorophosphate (HATU, 134.4 mg, 0.354 mmol) was added dimethyl sulfoxide (DMSO, 20 mL). The mixture was stirred at room temperature for 3 minutes, then N,N-diisopropylethylamine (DIPEA, 68.5 mg, 0.530 mmol) was added. After 5 minutes, the cloudy mixture became a clear solution. The reaction was monitored by SCX-HPLC. After 2 hours, 20 mL of 10% ammonium hydroxide solution (2.8% $NH_3$) was added. The mixture was stirred at room temperature for an additional 2 hours. The reaction was terminated by the addition of 400 mL water. Trifluoroethanol (2.0 mL) was added to the solution.

The solution was divided into two portions and each portion was purified by a WCX column (10 g resin per column). Each WCX column was first washed with 20% acetonitrile in water (v/v) to remove the PMO 4658 starting material. The washings (225 mL for each column) were Analytical Procedures: Matrix-assisted laser desorption ionization time-of-flight mass spectra (MALDI-TOF-MS) were recorded on a Bruker Autoflex™ Speed, using a sinapinic acid (SA) matrix. SCX-HPLC was performed on a Thermo Dionex UltiMate 3000 system equipped with a 3000 diode array detector and a ProPac™ SCX-20 column (250×4 mm) using a flow rate of 1.0 mL/min (pH=2; 30° C. column temperature). The mobile phases were A (25% acetonitrile in stopped when MALDI-TOF mass spectrum analysis showed the absence of PMO 4658 signal. Each column was then washed with water (100 mL per column). The desired product, PPMO4658, was eluted by 2.0 M guanidine HCl (140 mL for each column). The purified solutions of PPMO4658 were pooled together and then divided into two portions and each desalted by an SPE column (10 g resin for each column).

The SPE column was first washed with 1.0 M aqueous NaCl solution (100 mL for each column) to generate the hexahydrochloride salt of PPMO46581. Each SPE column was then washed with water (200 mL for each column). The final desalted PPMO-G was eluted by 50% acetonitrile in water (v/v, 150 mL for each column). The acetonitrile was removed by evacuation at reduced pressure. The resulting aqueous solution was lyophilized to obtain the desired conjugate PPMO4658 hexahydrochloride (1.93 g, 94.5% yield).

Example 1: PMO #1

Using the PMO synthesis method B protocol described above for PMO-G, PMO #1 was synthesized:

PMO#1

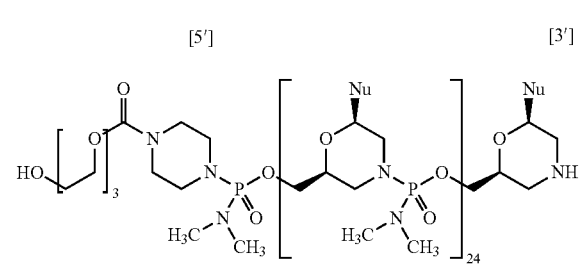

where each Nu from 1 to 25 and 5' to 3' is:

| Position No. 5' to 3' | Nu |
|---|---|
| 1 | C |
| 2 | T |
| 3 | G |
| 4 | T |
| 5 | T |
| 6 | C |
| 7 | C |
| 8 | A |
| 9 | A |
| 10 | A |
| 11 | T |
| 12 | C |
| 13 | C |
| 14 | T |
| 15 | G |
| 16 | C |
| 17 | A |
| 18 | T |
| 19 | T |
| 20 | G |
| 21 | T |
| 22 | T |
| 23 | G |
| 24 | C |
| 25 | C | wherein A is

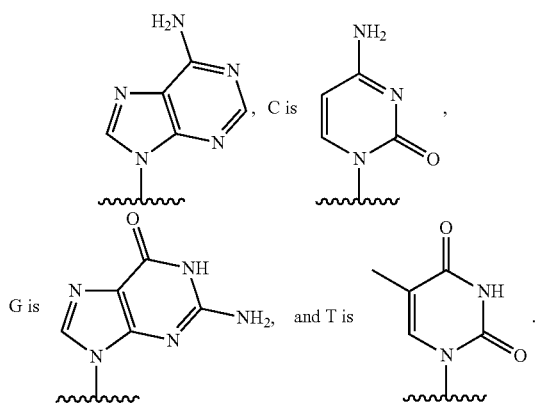

HPLC: 93.33%;

Example 2: PPMO #1

Using the protocol described above for preparation of PPMO4658, PPMO #1 was synthesized from PMO #1:

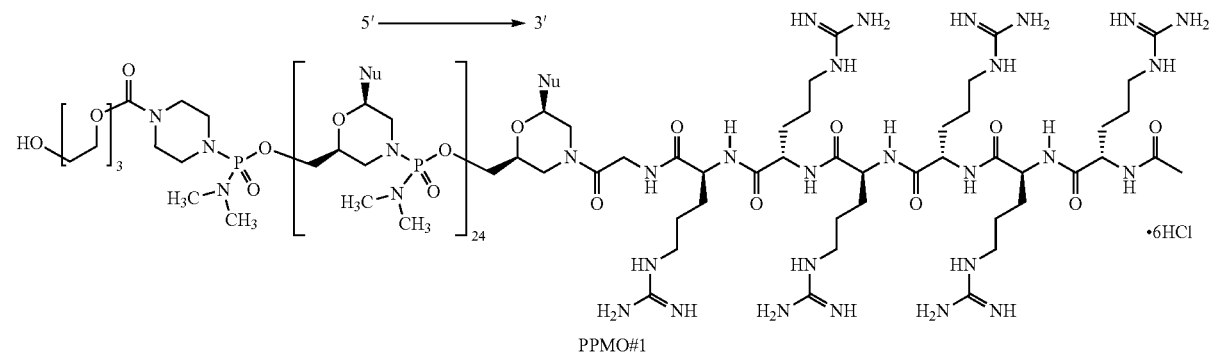

PPMO#1 where each Nu from 1 to 25 and 5' to 3' is:

| Position No. 5' to 3' | Nu |
|---|---|
| 1 | C |
| 2 | T |
| 3 | G |
| 4 | T |
| 5 | T |
| 6 | C |
| 7 | C |
| 8 | A |
| 9 | A |
| 10 | A |
| 11 | T |
| 12 | C |
| 13 | C |
| 14 | T |
| 15 | G |
| 16 | C |
| 17 | A |
| 18 | T |
| 19 | T |
| 20 | G |
| 21 | T |
| 22 | T |
| 23 | G |
| 24 | C |
| 25 | C | wherein A is

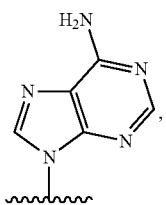 [SMILES: *n1cnc2c(N)ncnc21]

C is

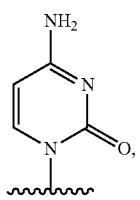 [SMILES: *n1ccc(N)nc1=O]

G is

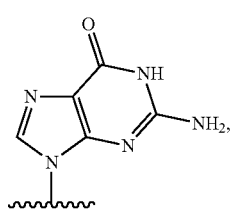

and T is

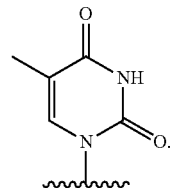 [SMILES: *n1cc(C)c(=O)[nH]c1=O]

HPLC:89.45%.

Example 3: Exon 52 Skipping In Vitro (Myoblasts)

Two compounds that target human dystrophin (DMD) exon 52 as described in the table below, PMO #1 and PPMO #1 both of which contain the same sequence, were assessed for DMD exon 52 skipping in healthy human myoblasts.

| Sequences of PMO#1 and PPMO#1 for human DMD exon 52. | | | | |
|---|---|---|---|---|
| Name | Targeting Sequence (TS) | TS SEQ ID NO. | 5' | 3' |
| PMO#1 | CTGTTCCAAATCCTGCATTGTTGCC | 1 | EG3 | H |
| PPMO#1 | CTGTTCCAAATCCTGCATTGTTGCC | 1 | EG3 | -G-R$_6$ |

Specifically, healthy human myoblasts (passage 5-6, SKB-F—SL purchased from Zen-Bio, Inc.) were plated at 40% confluency when treated with PMO #1 or PPMO #1 at various concentrations (i.e., 40 μm, 20 μm, 10 μm, 5 μm, 2.5 μm, and 1.25 μm) in SKM-M media (Zen-Bio, Inc.). After ninety-six hours of incubation, myoblasts were washed with PBS and lysed by RA1 lysis buffer in the Illustra GE RNAspin 96 kit (Cat #25-055-75, GE Healthcare Bio-Sciences). Total RNA were isolated per manufacturer's recommendation, except that 40 μL RNase-free water was used to elute RNA.

To determine exon 52 skipping by both compounds, two-step end-point RT-PCR was performed. Specifically, eleven microliters of total RNA was first reverse transcribed to cDNA by SuperScript IV First-strand synthesis kit (Cat #18091200, Invitrogen) using random hexamers as per the manufacturer's instructions. PCR was performed by adding 9 μL cDNA into Platinum Taq DNA polymerase PCR Supermix High Fidelity (Cat #12532024, Invitrogen) with forward primer that targeted human DMD exon 50 (forward primer: (SEQ ID NO: 5): CTCTGAGTG-GAAGGCGGTAA; and reverse primer that targeted exon 53: (SEQ ID NO: 6): ACCTGCTCAGCTTCTTCCTT). PCR amplification was performed using BioRad CFX96 real time thermocycler using the program shown in Table 2. Expression of the skipped or non-skipped PCR products were assessed by loading 32 μL PCR product onto LabChip GX system using DNA High Sensitivity Reagent kit (CLS760672, Perkin Elmer). Percentage of DMD exon 52 skipping is calculated as the percentage of the molarity (nmol/l) for exon 52 skipped band (364 bp) compared to the sum molarity for the skipped (364 bp) and the unskipped (482 bp) bands.

Two-tailed, unpaired Student's t-test (homoscedastic) was used to assess whether the means of the 2 groups are statistically different from each other at each dose. P-value <0.05 is considered as statistically significant.

| Thermocycler program used to amplify DMD amplicons with or without exon 52 skipping. | | |
|---|---|---|
| Step | Temperature | Time |
| 1. Denature | 94° C. | 2 min |
| 2. Denature | 94° C. | 30 sec |
| 3. Anneal | 61.2° C. | 30 sec |
| 4. Extend | 68° C. | 1 min |
| 5. Repeat step 2-4 | | 34 cycles |
| 6. Final Extension | 68° C. | 5 min |
| 7. Store | 4° C. | ∞ |

Figure 4:
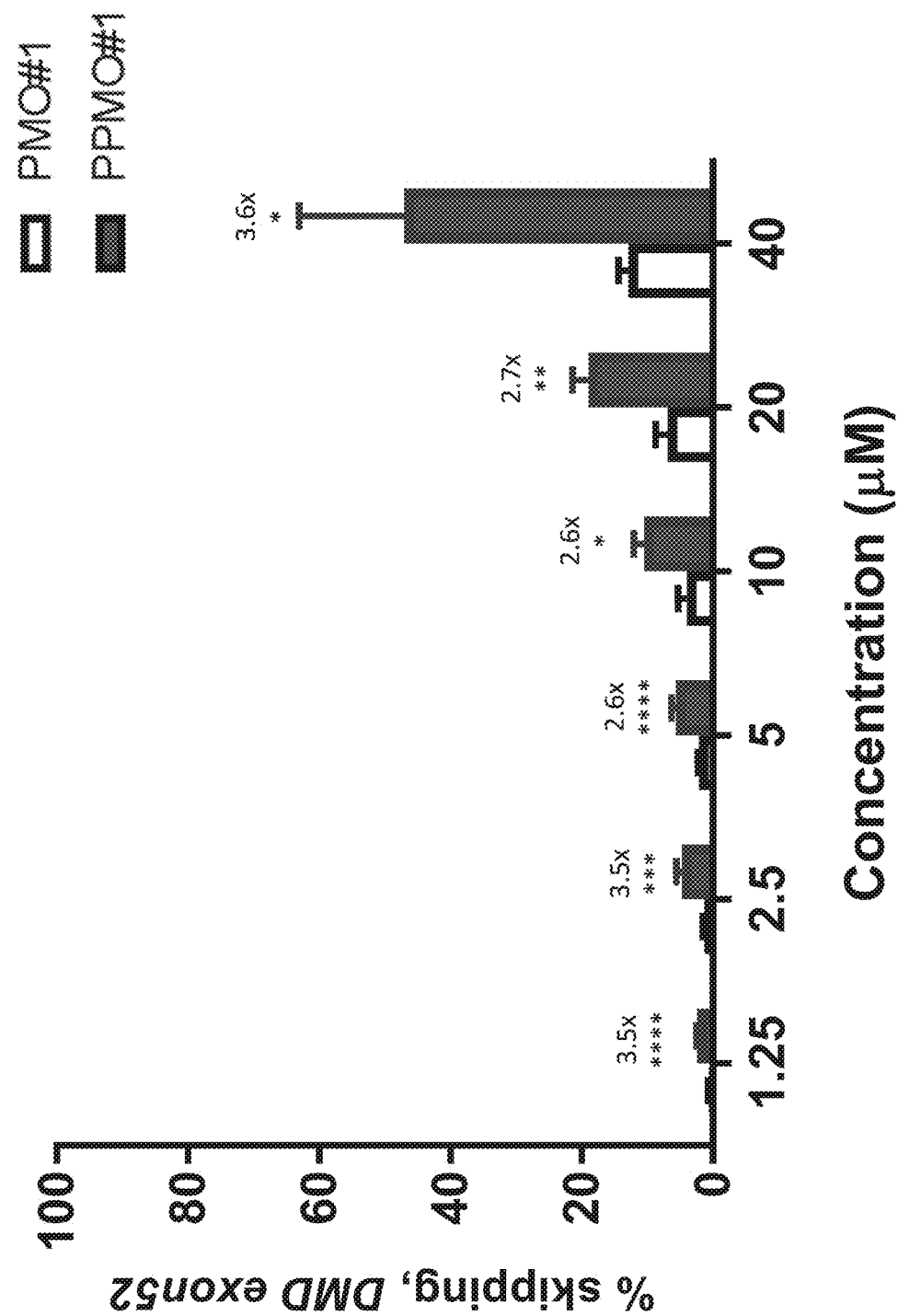
FIG. 4 provides a bar graph of the percentage of exon 52 skipping in healthy human myoblasts by PMO #1 and PPMO #1 at various concentrations 96 hours after treatment, as measured by RT-PCR. Error bars represent mean±SD.

The results are presented in the table below and in FIG. 4. In FIG. 4, error bars presents mean±SD, "[Number] x" above the bars denotes relative fold-change in percentage of exon skipping by PPMO #1 compared to PMO #1 at each concentration, and "*" indicates significant difference between PMO #1 and PPMO #1 with p-value <0.05.

| Percentage of DMD exon 52 skipping by PMO#1 and PPMO#1 in human myoblasts. | | | | | | |
|---|---|---|---|---|---|---|
| Compound/ | Percent Exon Skipping (mean ± SD) | | | | | |
| Dose (μm) | 1.25 | 2.5 | 5 | 10 | 20 | 40 |
| PMO#1 | 0.7 ± 0.089 | 1.36 ± 0.25 | 2.19 ± 0.21 | 4.05 ± 1.30 | 6.94 ± 1.85 | 12.94 ± 1.21 |
| PPMO#1 | 2.46 ± 0.07 | 4.75 ± 0.89 | 5.72 ± 0.66 | 10.54 ± 1.60 | 19.02 ± 2.45 | 47.11 ± 16.02 |

The data in the table above and in FIG. 4 surprisingly show that significantly higher exon 52 skipping results in myoblasts when the cells are treated with PPMO #1 as compared to PMO #1 at all concentrations, the degree of which is unexpected. This significant improvement is likely to be further demonstrated in an in vivo comparative test such as the non-human primate (NHP) study of Example 5 where NHPs are treated with PPMO #1 or PMO #1 and exon 52 skipping is measured in various relevant muscle tissues (see Example 5 for details).

Example 4: MDX Mouse Study

The mdx mouse is an accepted and well-characterized animal model for Duchene muscular dystrophy (DMD) containing a mutation in exon 23 of the dystrophin gene. The M23D antisense sequence (SEQ ID NO: 2) is known to induce exon 23 skipping and restore of functional dystrophin expression. MDX mice at 6-7 weeks of age were given a single injection into the tail vein of either a PPMO4225 or PMO 4225 of the table below at a dose of 40 mg/kg, or with saline.

| Name | Targeting Sequence (TS) | TS SEQ ID NO. | 5' | 3' |
|---|---|---|---|---|
| PMO4225 | GGCCAAACCTCGGCTTACCTGAAAT | 2 | EG3 | H |
| PPMO4225 | GGCCAAACCTCGGCTTACCTGAAAT | 2 | EG3 | -G-$R_6$ |

PMO4225 and PPMO4225 were each prepared by PMO Method A and CPP conjugation methods described above.

Treated mice were sacrificed at 7, 30, 60 and 90 days post single dose injection (n=6 per group). The diaphragm, heart and right quadriceps were processed for western blot analysis to measure production of dystrophin protein and RT-PCR analysis to measure percentage of exon skipping, and the left quadriceps was processed for immunohistochemistry and H/E staining as described above.

Dystrophin protein restoration was quantified by western blot, and percentage of exon 23 skipping was measured by RT-PCR each as described above.

RT-PCR and Western Blot results are shown in FIGS. 5A-10B and in the tables below. Surprisingly, PPMO4225 induced significantly higher and sustained levels of dystrophin restoration and exon 23 skipping compared to PMO4225, with highest levels occurring at 30-days post injection. Even more surprising, PPMO4225 increased dystrophin levels in the heart when PMO4225 did not; dystrophin and exon skipping were not observed in the heart at all time points with PMO4225.

| Quantification of Dystrophin Protein as Percentage of Wild Type Protein (% WT) by Western Blot | | | | | | | | |
|---|---|---|---|---|---|---|---|---|
| | Compound | | | | | | | |
| | PMO4225 | | | | PPMO4225 | | | |
| | Day | | | | | | | |
| Tissue | 7 | 30 | 60 | 90 | 7 | 30 | 60 | 90 |
| Quadriceps | 1.1 | 2.3 | 1.6 | 0.7 | 20.7 | 28.1 | 20.8 | 8.2 |
| Diaphragm | 1.4 | 1.9 | 1.3 | 0.6 | 14.5 | 15.2 | 9.8 | 2.3 |
| Heart | 0 | 0 | 0 | 0 | 2.0 | 1.0 | 0.9 | 0.1 |

| Percent Exon Skipping as Measured by RT-PCR | | | | | | | | |
|---|---|---|---|---|---|---|---|---|
| | Compound | | | | | | | |
| | PMO4225 | | | | PPMO4225 | | | |
| | Day | | | | | | | |
| Tissue | 7 | 30 | 60 | 90 | 7 | 30 | 60 | 90 |
| Quadriceps | 21.2 | 5.5 | 7.9 | 2.8 | 61.5 | 42.02 | 28.8 | 6.9 |
| Diaphragm | 29.9 | 2.6 | 0.5 | 0 | 51.6 | 36.76 | 3.05 | 0 |
| Heart | 0 | 0 | 0 | 0 | 13.15 | 2.64 | 0 | 0 |

Figure 11:
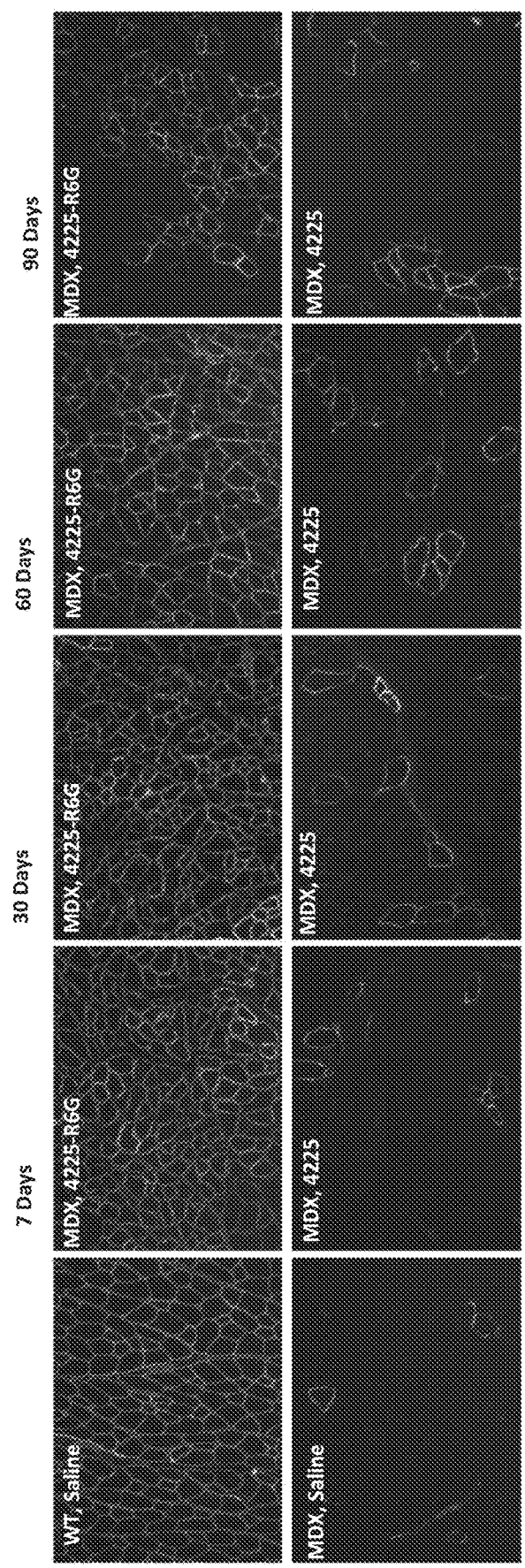
FIG. 11 provides immunohistochemistry analysis showing dystrophin in mdx mouse left quadriceps induced by PMO (PMO 4225) or PPMO (PPMO4225).
Figure 12A:
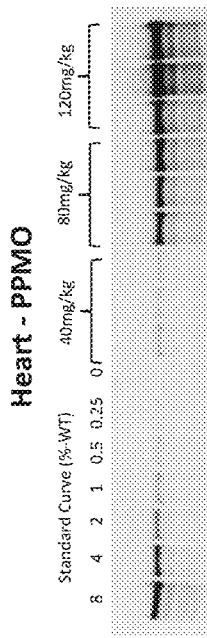
FIG. 12A-B provide representative images of Western Blot analysis measuring dystrophin protein in the heart of mdx mice treated with PMO (PMO 4225) or PPMO (PPMO4225) for different doses: 40 mg/kg, 80 mg/kg, and 120 mg/kg.
Figure 12B:
Figure 13:
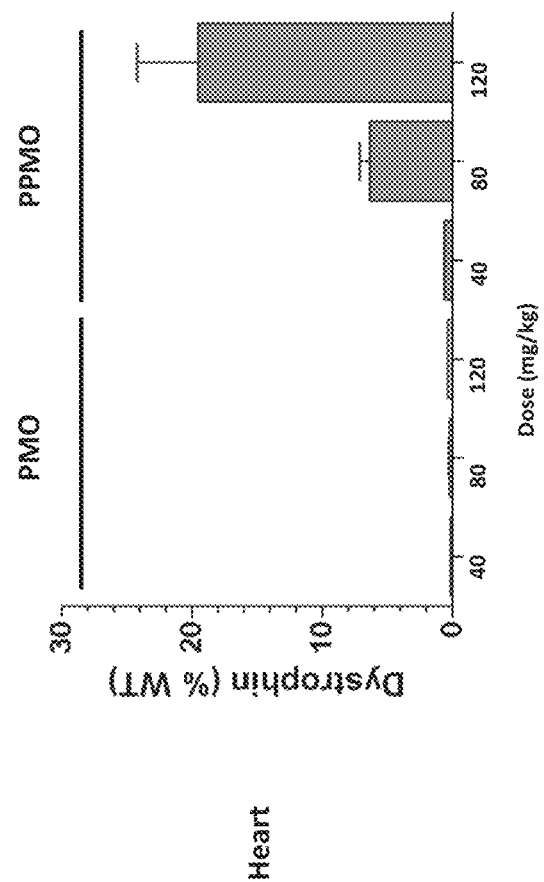
FIG. 13 provides a bar graph depicting the percentage of wild-type dystrophin induced by PMO (PMO 4225) or PPMO (PPM4225) in the heart of mdx mice as determined by Western Blot analysis 30 days post-injection at different doses: 40 mg/kg, 80 mg/kg, and 120 mg/kg.
Figure 14A:
FIG. 14A-B provide representative images of Western Blot analysis measuring dystrophin protein in the diaphragm of mdx mice treated with PMO (PMO 4225) or PPMO (PPMO4225) for different doses 40 mg/kg, 80 mg/kg, and 120 mg/kg.
Figure 14B:
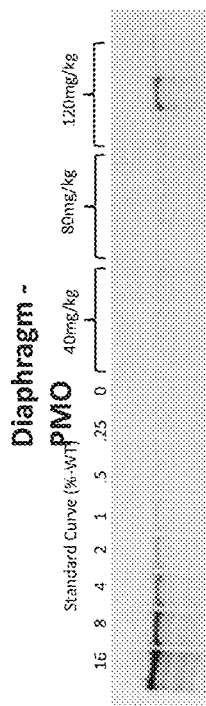
Figure 15:
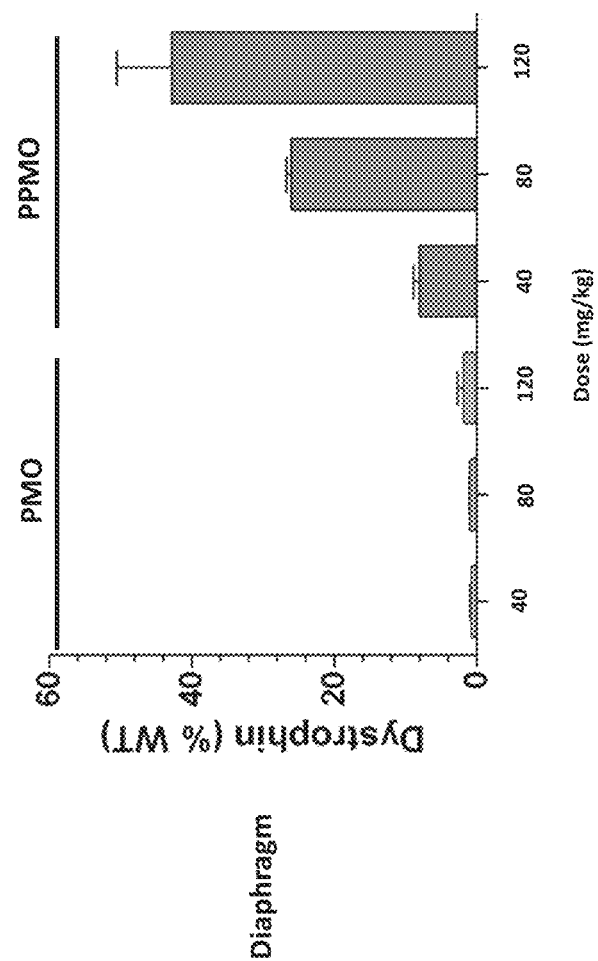
FIG. 15 provides a bar graph depicting the percentage of wild-type dystrophin induced by PMO (PMO 4225) or PPMO (PPMO4225) in the diaphragm of mdx mice as determined by Western Blot analysis 30 days post-injection at different doses: 40 mg/kg, 80 mg/kg, and 120 mg/kg.
Figure 16B:
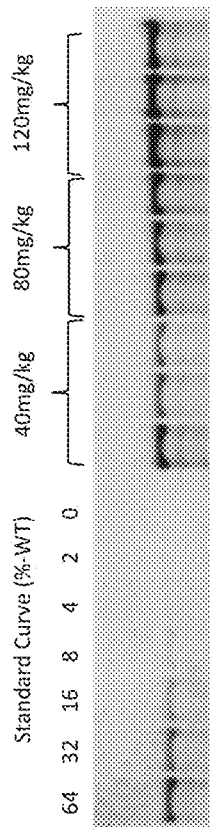
FIG. 16A-B provide representative images of Western Blot analysis measuring dystrophin protein in the quadriceps of mdx mice treated with PMO (PMO 4225) or PPMO (PPMO4225) at different doses: 40 mg/kg, 80 mg/kg, and 120 mg/kg.
Figure 16A:
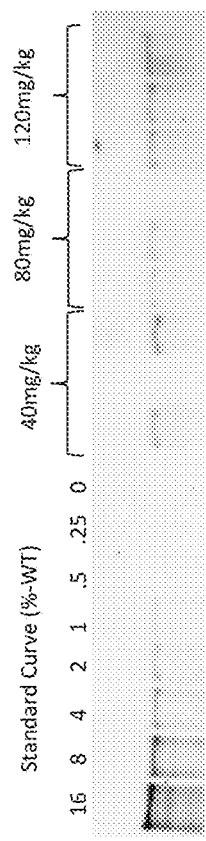
Figure 17:
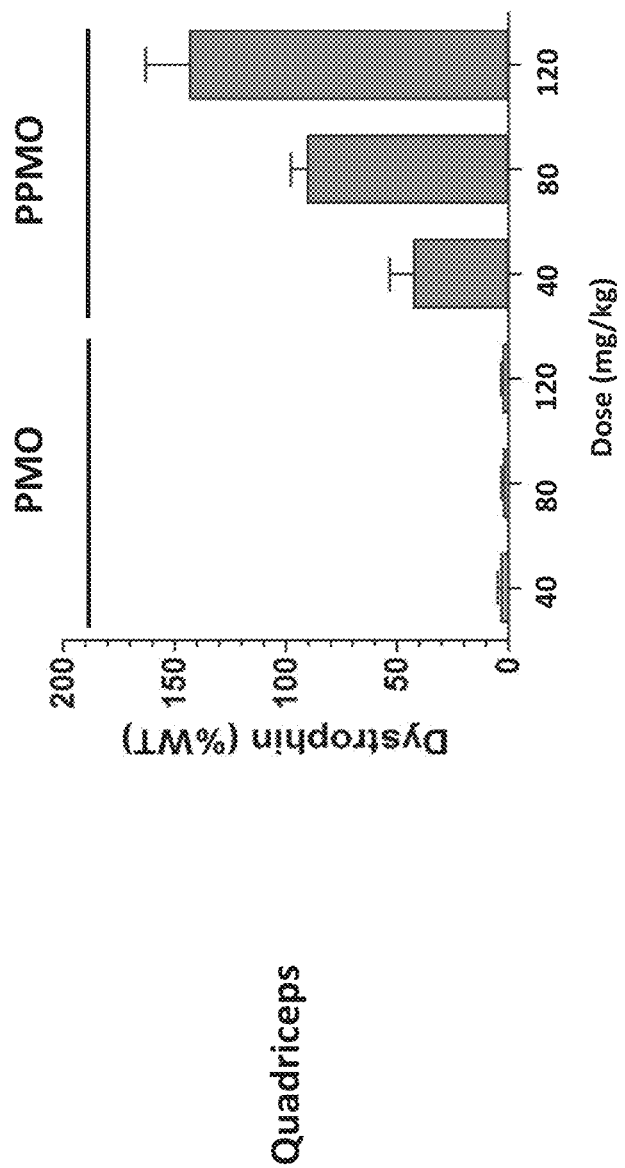
FIG. 17 provides a bar graph depicting the percentage of wild-type dystrophin induced by PMO (PMO 4225) or PPMO (PPMO4225) in the quadriceps of mdx mice as determined by Western Blot analysis 30 days post-injection at different doses: 40 mg/kg, 80 mg/kg, and 120 mg/kg.

Immunohistochemistry results are shown in FIG. 11. Here, PPMO4225 restores dystrophin throughout the quadriceps, whereas 4225 produces a 'patchy-like' pattern of expression. The uniform distribution of dystrophin with PPMO4225 treatment indicates that widespread targeting of skeletal muscle is achievable. PPMO4225 has significantly improved delivery over PMO4225 in vivo.

Example 5: Exon 52 Skipping in NHP

To further demonstrate the efficacy of exon skipping of PPMO antisense oligomers, non-human primates are utilized. Specifically, cynomolgus monkeys having intact muscle tissues are injected intravenously, with PPMO #1, PMO #1 (from Example 3), or saline according to the dosing schedule presented in FIG. 20.

Animals will be observed throughout the study, including clinical observations (e.g., evaluation of skin and fur, respiratory effects) and body weight measurements. Blood and urine samples will be taken at least before testing begins, and 24 hours after the first dose and last dose (where applicable).

At each scheduled necropsy, or euthanized in extremis, sections of diaphragm, smooth muscle of the duodenum, esophagus, and aorta, quadriceps, deltoid, bicep, and heart are collected and snap frozen. Percent exon 52 skipping is determined using RT-PCR as described above.

Example 6: MDX Mouse Dose Response Study

MDX mice at 6-7 weeks of age were given a single injection into the tail vein of either a PPMO4225 or PMO 4225 described above at a dose of 40 mg/kg, 80 mg/kg, or 120 mg/kg (n=6 per group).

Treated mice were sacrificed at 30 days post injection. The diaphragm, quadriceps, and heart were processed for western blot analysis to measure production of dystrophin protein based on the above-described western blot protocol (used, for example, in Example 4) with the following modifications:

| Parameter | Western Blot Protocol of Example 4 | Western Blot Protocol modifications |
|---|---|---|
| Protein quantification | RC DC Protein Assay Kit | BCA method |
| Blocking Step | Overnight at 4° C. | 1 Hour at RT |
| Primary Antibody Incubation | 1 hour at RT | Overnight at 4° C. |
| Primary Antibody Concentration | 1:20 | 1:500 |

Dystrophin protein restoration as % wild type is presented in the table below and in FIGS. 12-15.

| | Quantification of Dystrophin Protein as Percentage of Wild Type Protein (% WT) by Western Blot | | | | | |
|---|---|---|---|---|---|---|
| | Compound | | | | | |
| | PMO4225 | | | PPMO4225 | | |
| | Dose (mg/kg) | | | | | |
| Tissue | 40 | 80 | 120 | 40 | 80 | 120 |
| Diaphragm | 0.80 | 0.97 | 1.83 | 8.02 | 26.03 | 42.77 |
| Heart | 0.13 | 0.24 | 0.34 | 0.61 | 6.34 | 19.48 |
| Quadriceps | 3.5 | 2.6 | 3.0 | 43 | 90 | 144 |

Surprisingly, the data shows that a single dose of PPMO4225 increases dystrophin levels in a dose-dependent manner in mdx mice to significantly and substantially greater extent than PMO 4225.

Example 7: MDX Mouse IHC Study of Diaphragm and Heart

Figure 19:
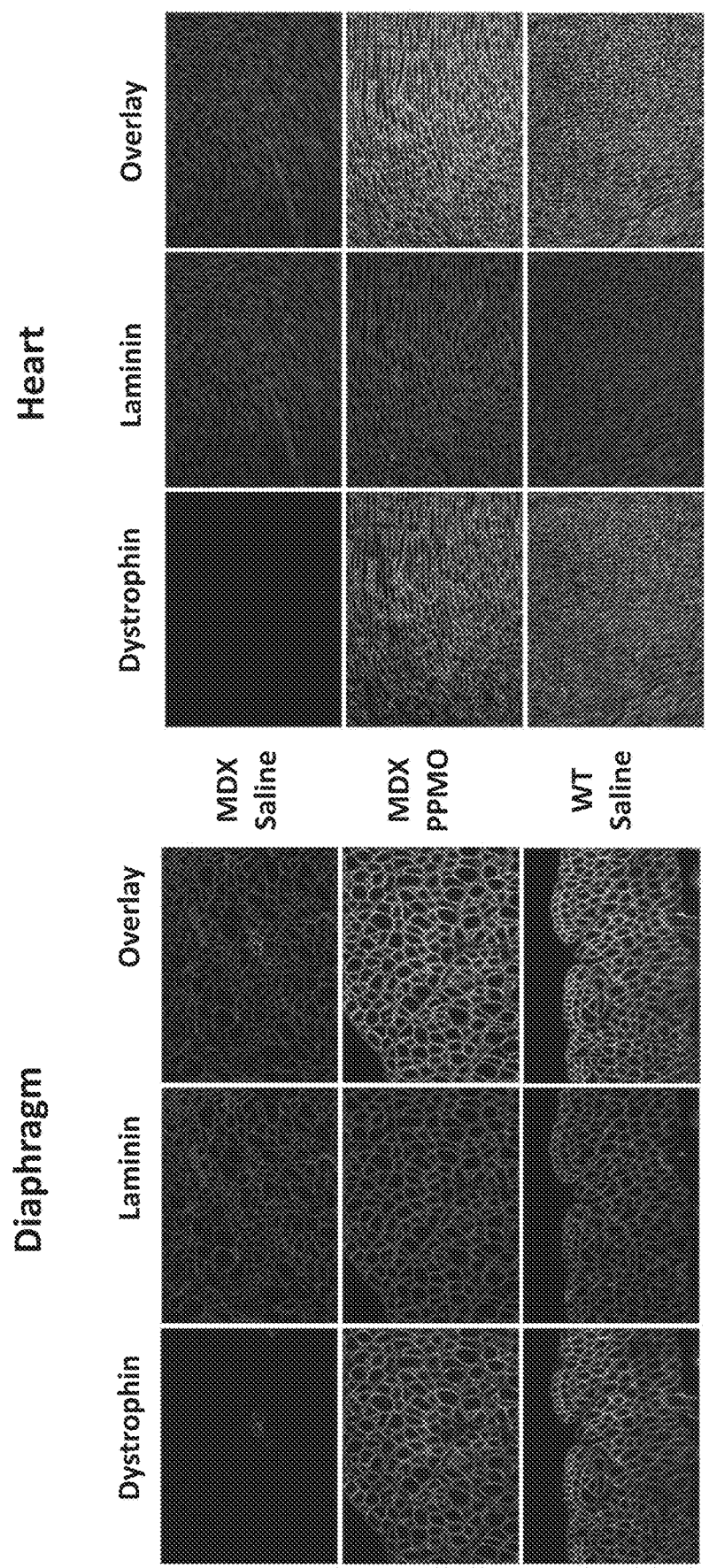
FIG. 19 provides immunohistochemistry analysis showing dystrophin and laminin in mdx mouse diaphragm and heart induced by PPMO (PPMO4225) compared to saline in mdx mice and wild type mice.

MDX mice at 6-7 weeks of age were given a single injection into the tail vein of PPMO4225 at a dose of 80 mg/kg or saline, and wild type mice at 6-7 weeks of age where given a single injection of saline. The treated mdx mice, saline mdx mice, and wild type mice were sacrificed at 30 days post single dose injection (n=4 per group). Immunohistochemistry results are shown in FIG. 19. Here, the results show uniform increase in dystrophin in tissues associated with morbidity and mortality in DMD in mdx mice treated with PPMO4225.

All publications and patent applications cited in this specification are herein incorporated by reference as if each individual publication or patent application were specifically and individually indicated to be incorporated by reference.

REFERENCES

Aartsma-Rus, A., A. A. Janson, et al. (2004). "Antisense-induced multiexon skipping for Duchenne muscular dystrophy makes more sense." Am J Hum Genet 74(1): 83-92.

Abes, R., et al. (2008). "Arginine-rich cell penetrating peptides: design, structure-activity, and applications to alter pre-mRNA splicing by steric-block oligonucleotides." J Pept. Sci. 14: 455-460.

Alter, J., et al. (2006). "Systemic delivery of morpholino oligonucleotide restores dystrophin expression bodywide and improves dystrophic pathology." Nat. Med. 12(2): 175-177.

Bestas, B., et al. (2014). "Splice-correcting ligonucleotides restore BTK function in X-linked agammaglobulinemia model." J. Clin. Invest.

Cirak, S., V. Arechavala-Gomeza, et al. (2011). "Exon skipping and dystrophin restoration in patients with Duchenne muscular dystrophy after systemic phosphorodiamidate morpholino oligomer treatment: an open-label, phase 2, dose-escalation study." Lancet 378(9791): 595-605.

Dunckley, M. G., I. C. Eperon, et al. (1997). "Modulation of splicing in the DMD gene by antisense oligoribonucleotides." Nucleosides & Nucleotides 16(7-9): 1665-1668.

Dunckley, M. G., M. Manoharan, et al. (1998). "Modification of splicing in the dystrophin gene in cultured Mdx muscle cells by antisense oligoribonucleotides." Hum Mol Genet 7(7): 1083-90.

Errington, S. J., C. J. Mann, et al. (2003). "Target selection for antisense oligonucleotide induced exon skipping in the dystrophin gene." J Gene Med 5(6): 518-27.

Goemans, N. M., M. Tulinius, et al. (2011). "Systemic Administration of PRO051 in Duchenne's Muscular Dystrophy." N Engl J Med.

Jearawiriyapaisarn, N., H. M. Moulton, et al. (2008). "Sustained Dystrophin Expression Induced by Peptide-conjugated Morpholino Oligomers in the Muscles of mdx Mice." Mol Ther.

Jearawiriyapaisarn, N., et al. (2010). "Long-term improvement in mdx cardiomyopathy after therapy with peptide-conjugated morpholino oligomers." Cardiovascular Research 85: 444-453.

Kinali, M., V. Arechavala-Gomeza, et al. (2009). "Local restoration of dystrophin expression with the morpholino oligomer AVI-4658 in Duchenne muscular dystrophy: a single-blind, placebo-controlled, dose-escalation, proof-of-concept study." Lancet Neurol 8(10): 918-28.

Leblue, B., et al. (2008). "Cell penetrating peptide conjugates of steric block oligonucleotides." Adv. Drug Deliv. Rev. 60: 517-529.

Lu, Q. L., C. J. Mann, et al. (2003). "Functional amounts of dystrophin produced by skipping the mutated exon in the mdx dystrophic mouse." Nat Med 9(8): 1009-14.

Mann, C. J., K. Honeyman, et al. (2002). "Improved antisense oligonucleotide induced exon skipping in the mdx mouse model of muscular dystrophy." *J Gene Med* 4(6): 644-54.

Marshall, N. B., S. K. Oda, et al. (2007). "Arginine-rich cell-penetrating peptides facilitate delivery of antisense oligomers into murine leukocytes and alter pre-mRNA splicing." *Journal of Immunological Methods* 325(1-2): 114-126.

Matsuo, M., T. Masumura, et al. (1991). "Exon skipping during splicing of dystrophin mRNA precursor due to an intraexon deletion in the dystrophin gene of Duchenne muscular dystrophy kobe." *J Clin Invest* 87(6): 2127-31.

McClory, G., et al. (2006). "Antisense oligonucleotide-induced exon skipping restored dystrophin expression in vitro in a canine model of DMD." *Gene Therap* 13: 1373-1381.

Monaco, A. P., C. J. Bertelson, et al. (1988). "An explanation for the phenotypic differences between patients bearing partial deletions of the DMD locus." *Genomics* 2(1): 90-5.

Moulton, H. M., (2007). "Cell-penetrating peptide-morpholino conjugates alter pre-mRNA splicing of DMD (Duchenne muscular dystrophy) and inhibit murine coronavirus replication in vivo." *Biochem. Society Trans* 35(4): 826-828.

Pramono, Z. A., Y. Takeshima, et al. (1996). "Induction of exon skipping of the dystrophin transcript in lymphoblastoid cells by transfecting an antisense oligodeoxynucleotide complementary to an exon recognition sequence." *Biochem Biophys Res Commun* 226(2): 445-9.

Sazani, P., R. Kole, et al. (2007). Splice switching oligomers for the TNF superfamily receptors and their use in treatment of disease. PCT WO2007058894, University of North Carolina Sierakowska, H., M. J. Sambade, et al. (1996). "Repair of thalassemic human beta-globin mRNA in mammalian cells by antisense oligonucleotides." *Proc Natl Acad Sci USA* 93(23): 12840-4.

Summerton, J. and D. Weller (1997). "Morpholino antisense oligomers: design, preparation, and properties." *Antisense Nucleic Acid Drug Dev* 7(3): 187-95.

Takeshima, Y., H. Nishio, et al. (1995). "Modulation of in vitro splicing of the upstream intron by modifying an intra-exon sequence which is deleted from the dystrophin gene in dystrophin Kobe." *J Clin Invest* 95(2): 515-20.

van Deutekom, J. C., M. Bremmer-Bout, et al. (2001). "Antisense-induced exon skipping restores dystrophin expression in DMD patient derived muscle cells." *Hum Mol Genet* 10(15): 1547-54.

van Deutekom, J. C., A. A. Janson, et al. (2007). "Local dystrophin restoration with antisense oligonucleotide PRO051." *N En2l J Med* 357(26): 2677-86.

Wilton, S. D., A. M. Fall, et al. (2007). "Antisense oligonucleotide-induced exon skipping across the human dystrophin gene transcript." *Mol Ther* 15(7): 1288-96.

Wilton, S. D., F. Lloyd, et al. (1999). "Specific removal of the nonsense mutation from the mdx dystrophin mRNA using antisense oligonucleotides." *Neuromuscul Disord* 9(5): 330-8.

Wu, B., H. M. Moulton, et al. (2008). "Effective rescue of dystrophin improves cardiac function in dystrophin-deficient mice by a modified morpholino oligomer." *Proc Natl Acad Sci USA* 105(39): 14814-9.

Wu, B., et al. (2012). "Long-term rescue of dystrophin expression and improvement in muscle pathology and function in dystrophic mdx mice by peptide-conjugated morpholino." *The Am. J. Pathol.* 181(2): 392-400.

Wu, P., et al. (2007) "Cell-penetrating peptides as transporters for morpholino oligomers: effects of amino acid composition on intracellular delivery and cytotoxicity." *Nucleic Acids Research* 35(15): 5182-5191.

Yin, H., H. M. Moulton, et al. (2008). "Cell-penetrating peptide-conjugated antisense oligonucleotides restore systemic muscle and cardiac dystrophin expression and function." *Hum Mol Genet* 17(24): 3909-18.

Yin, H., et al. (2011). "Pip5 transduction peptides direct high efficiency oligonucleotide-mediated dystrophin exon skipping in heart and phenotypic correction in mdx mice." *Mol. Ther* 19(7): 1295-1303.

Youngblood, D., et al. (2006). "Stability of cell-penetrating peptide-morpholino oligomer conjugates in human serum and in cells." *Am. Chem. Soc.*

SEQUENCE LISTING

| Description | Sequence 5' to 3' or N terminus to C terminus | SEQ ID NO |
|---|---|---|
| H52A-01+24) | CTGTTCCAAATCCTGCATTGTTGCC | 1 |
| mdx4225 | GGCCAAACCTCGGCTTACCTGAAAT | 2 |
| $R_6$ | RRRRRR | 3 |
| $R_6$-G | RRRRRRG | 4 |
| Human exon 50 binding forward primer | CTCTGAGTGGAAGGCGGTAA | 5 |
| Human exon 53 binding forward primer | ACCTGCTCAGCTTCTTCCTT | 6 |
| Mouse exon 23 binding forward primer | CACATCTTTGATGGTGTGAGG | 7 |
| Mouse exon 23 binding reverse primer | CAACTTCAGCCATCCATTTCTG | 8 |
| PMO-G | GTTGCCTCCGGTTCTGAAGGTGTTC | 9 |
| 4658 | CTCCAACATCAAGGAAGATGGCATTTCTAG | 10 |

The invention claimed is:

1. A method for treating Duchenne muscular dystrophy (DMD) in a subject in need thereof wherein the subject has a mutation of the dystrophin gene that is amenable to exon 52 skipping, the method comprising administering to the subject an antisense oligomer conjugate of Formula (IV):

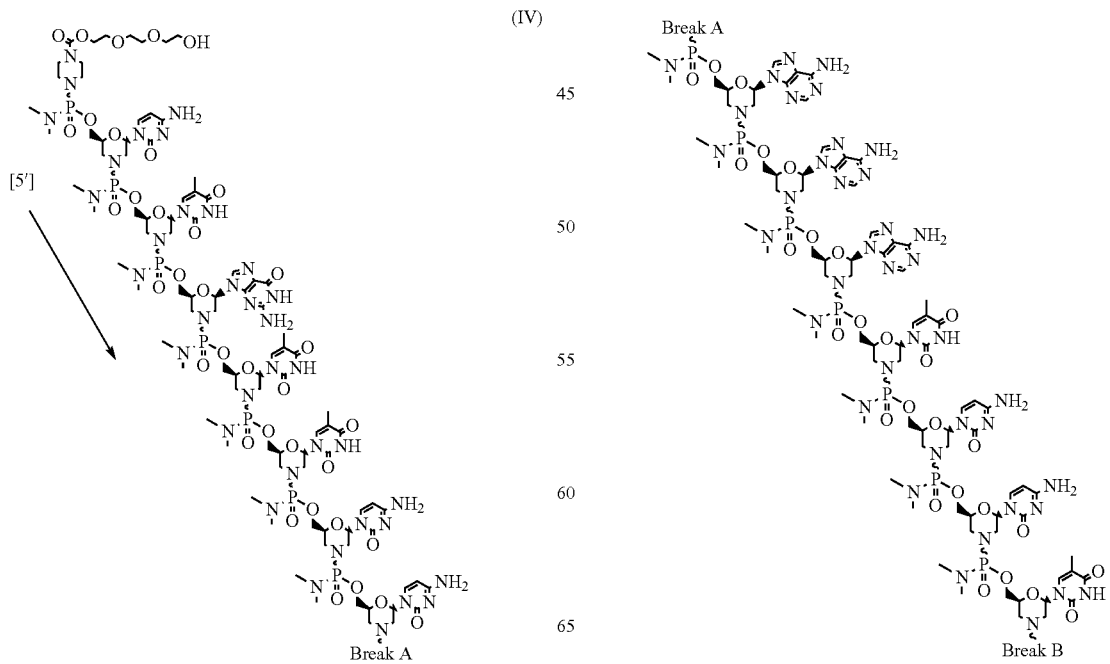

(IVA)
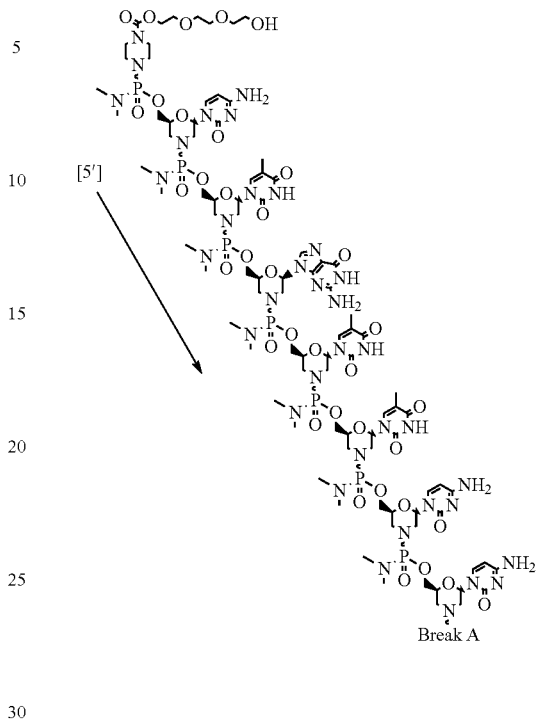
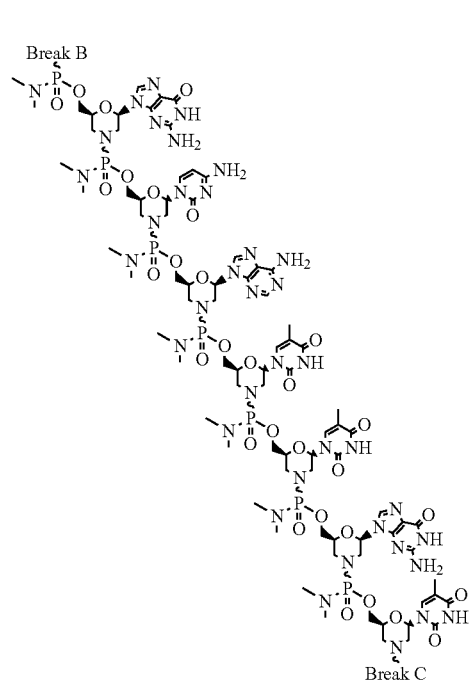
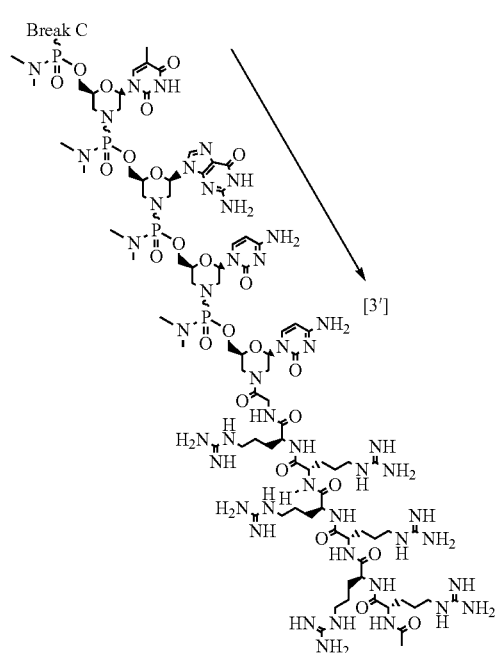
or a pharmaceutically acceptable salt thereof.
2. The method of claim 1, wherein the antisense oligomer conjugate is of Formula (IVA):

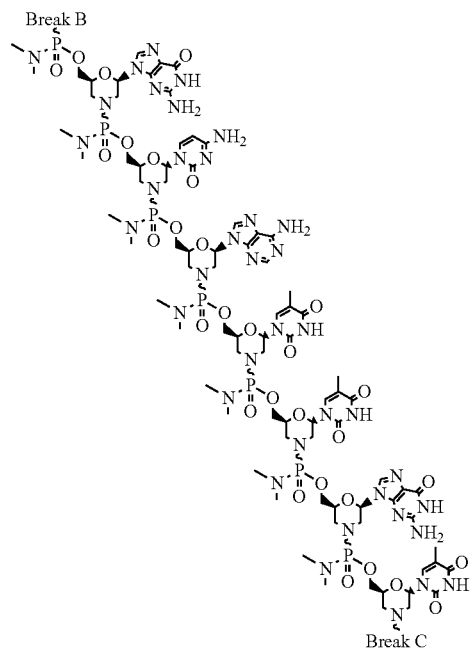
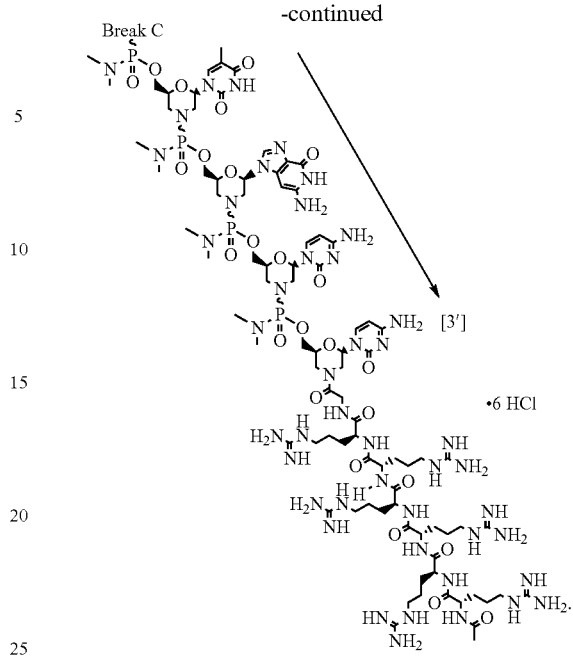
3. A method of restoring an mRNA reading frame to induce dystrophin production in a subject having a mutation of the dystrophin gene that is amenable to exon 52 skipping, the method comprising administering to the subject an antisense oligomer conjugate of Formula (IV):

(IV)
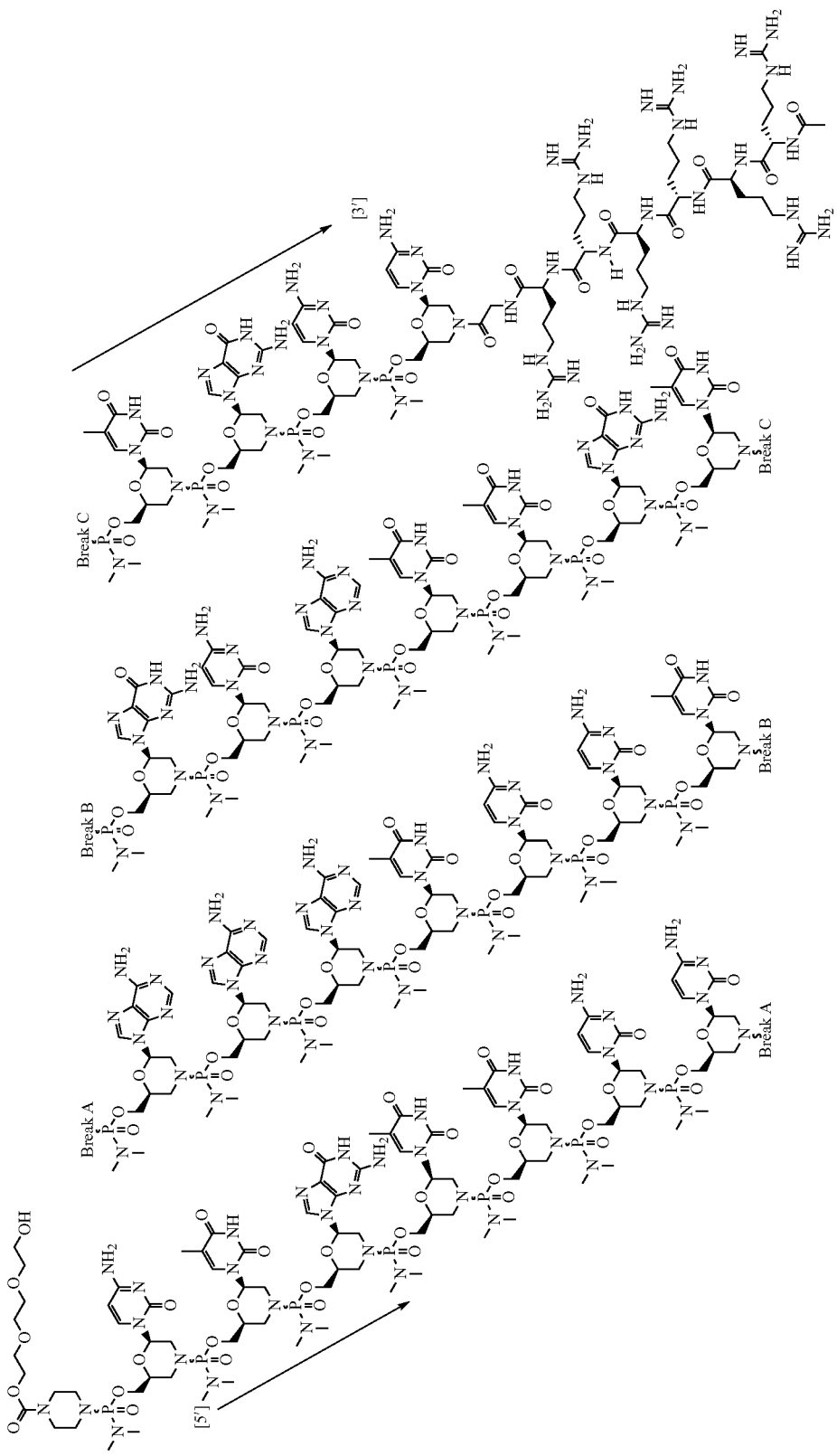

or a pharmaceutically acceptable salt thereof.

4. The method of claim 3, wherein the antisense oligomer conjugate is of Formula (IVA):

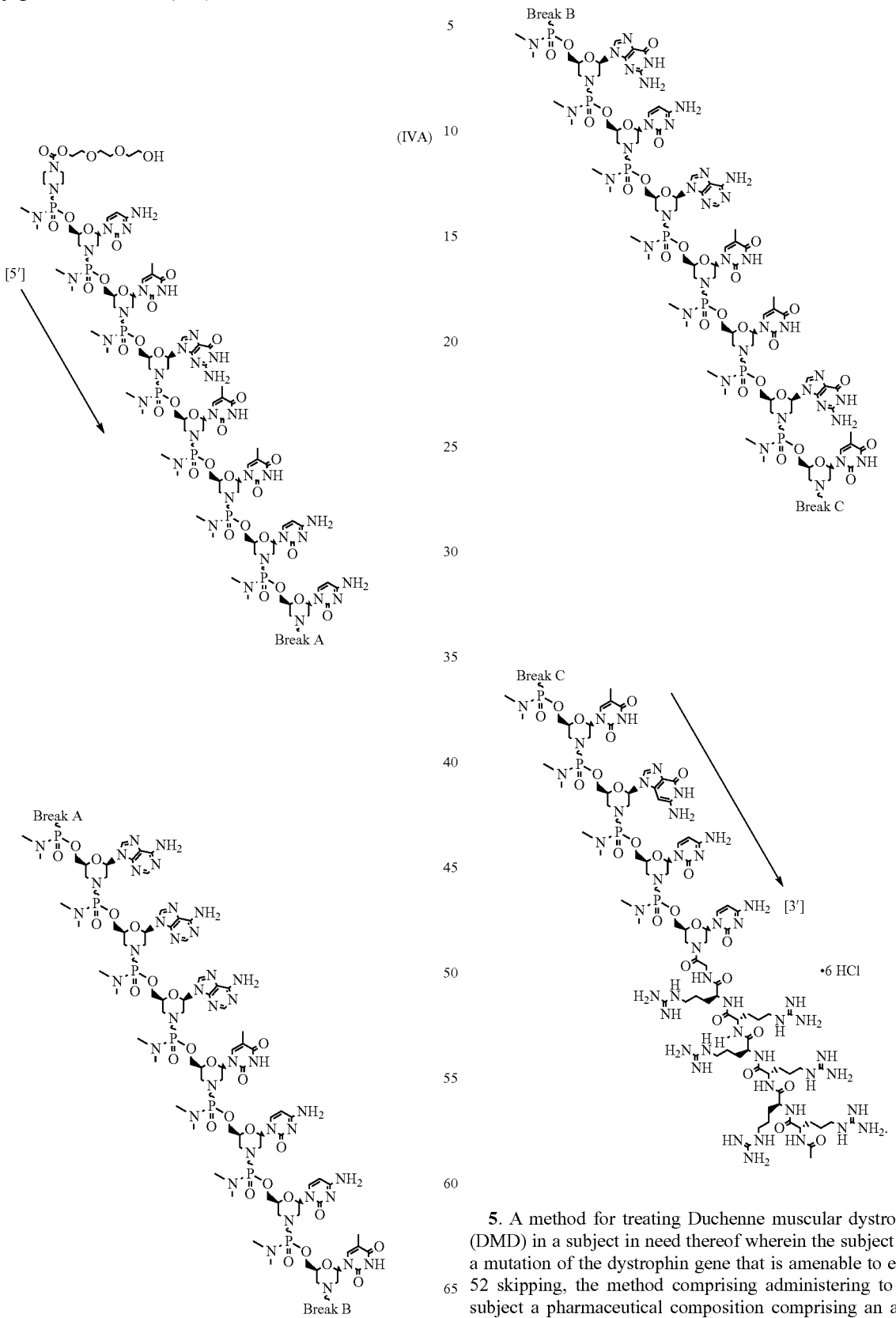

5. A method for treating Duchenne muscular dystrophy (DMD) in a subject in need thereof wherein the subject has a mutation of the dystrophin gene that is amenable to exon 52 skipping, the method comprising administering to the subject a pharmaceutical composition comprising an antisense oligomer conjugate of Formula (IV):

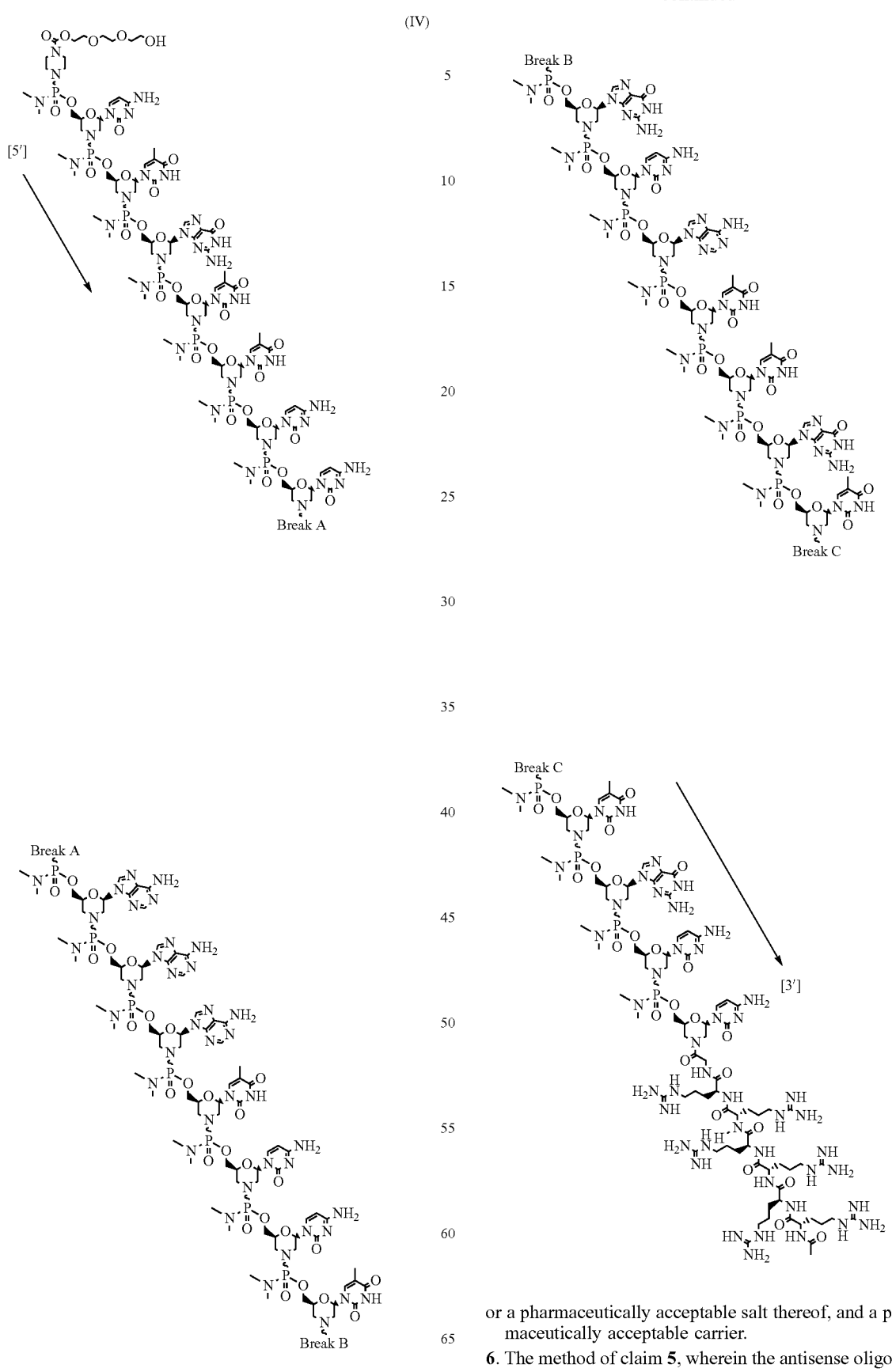
or a pharmaceutically acceptable salt thereof, and a pharmaceutically acceptable carrier.
6. The method of claim 5, wherein the antisense oligomer conjugate is of Formula (IVA):

(IVA)
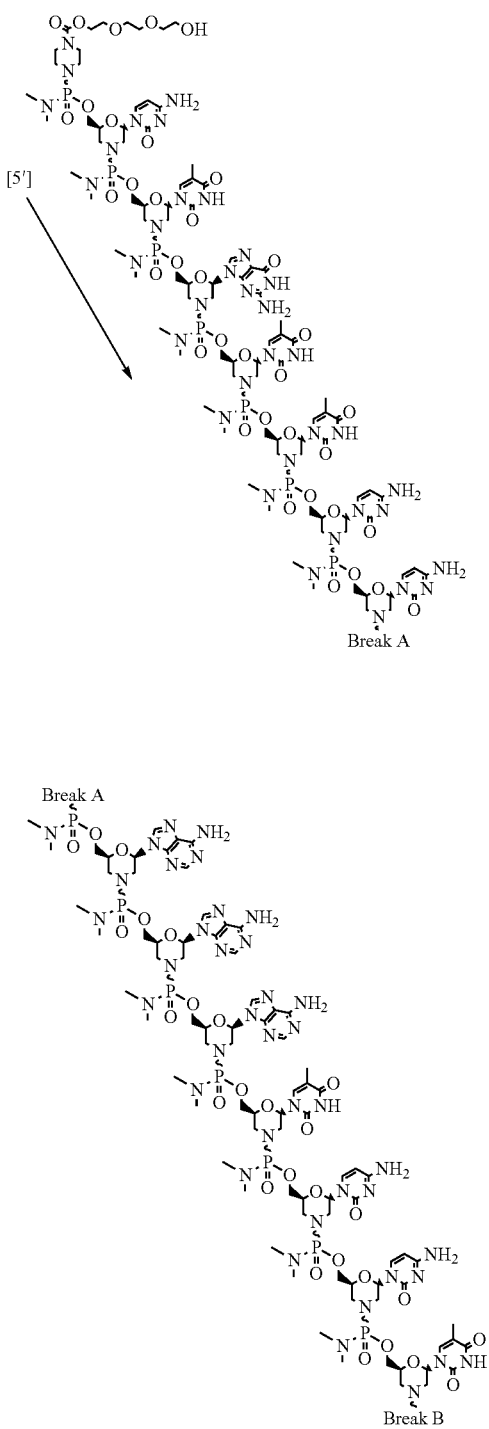
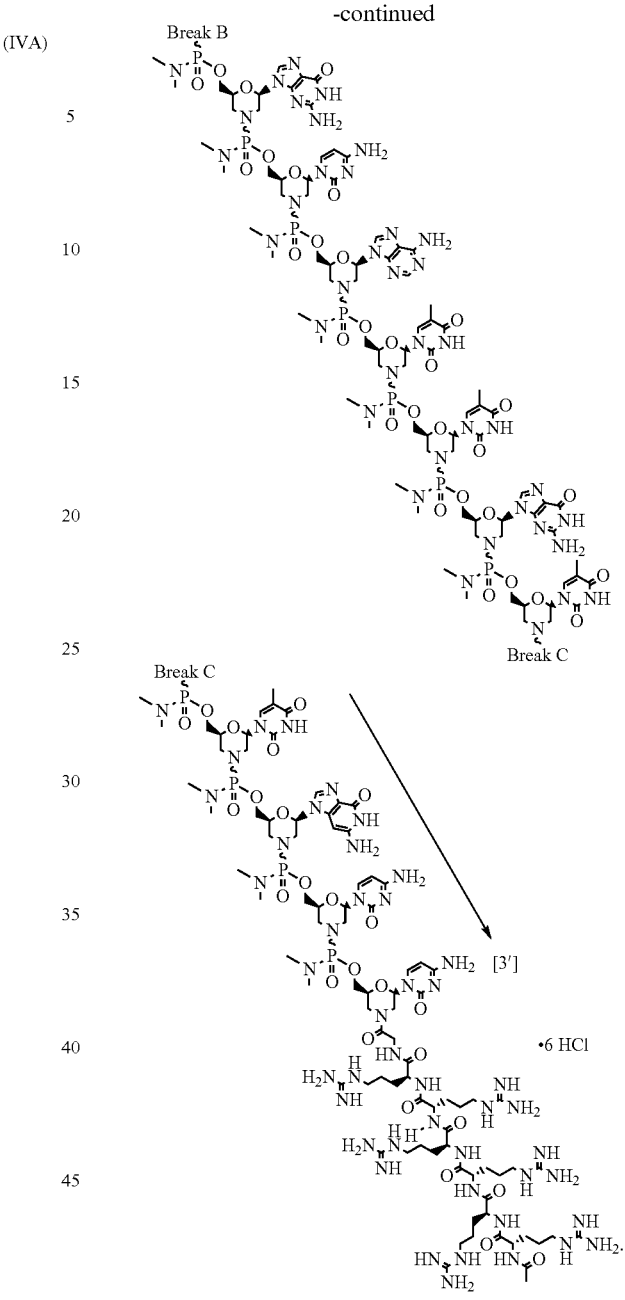
7. A method of restoring an mRNA reading frame to induce dystrophin production in a subject having a mutation of the dystrophin gene that is amenable to exon 52 skipping, the method comprising administering to the subject a pharmaceutical composition comprising an antisense oligomer conjugate of Formula (IV):

(IV)
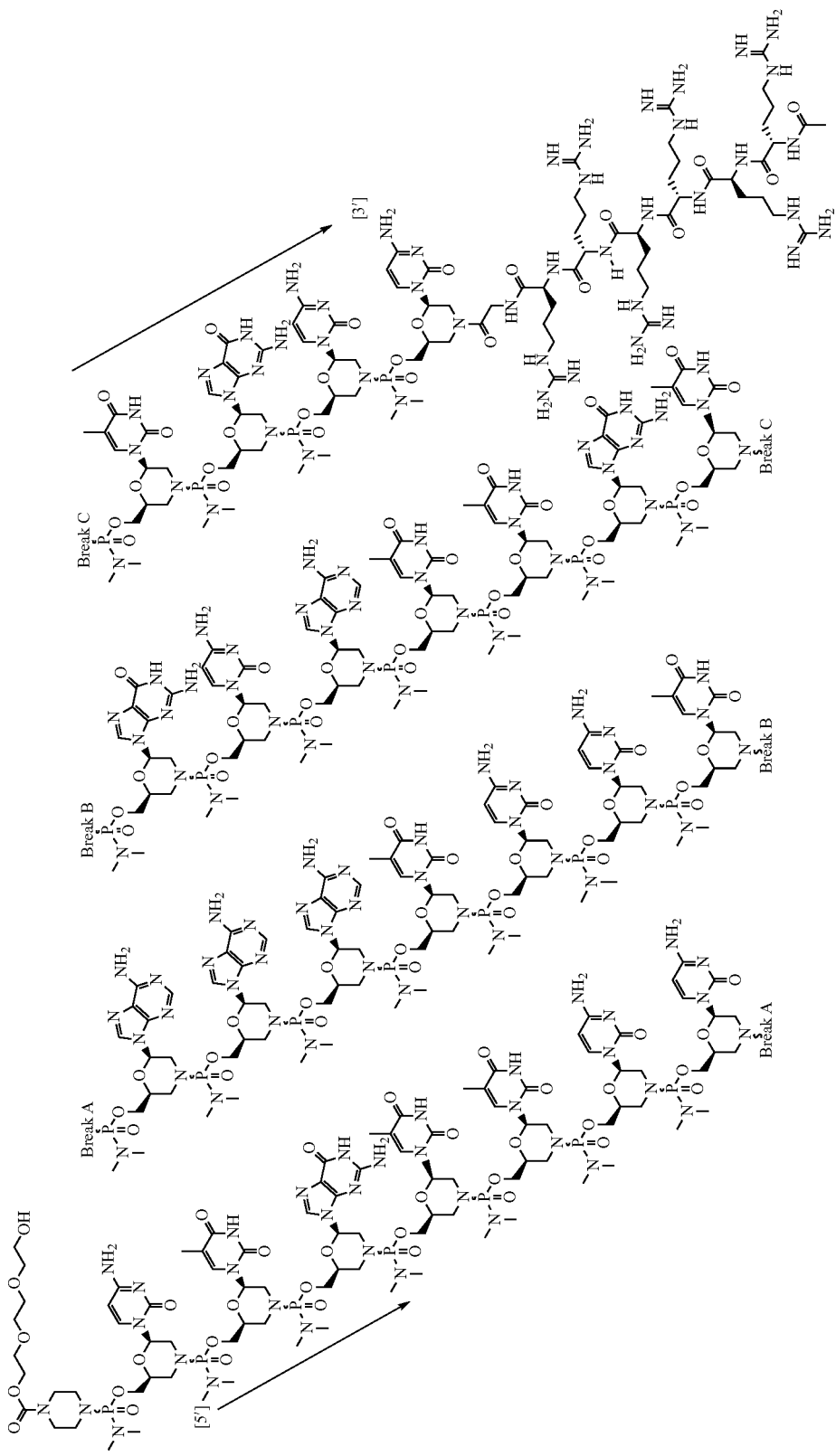

or a pharmaceutically acceptable salt thereof, and a pharmaceutically acceptable carrier.

8. The method of claim 7, wherein the antisense oligomer conjugate is of Formula (IVA):

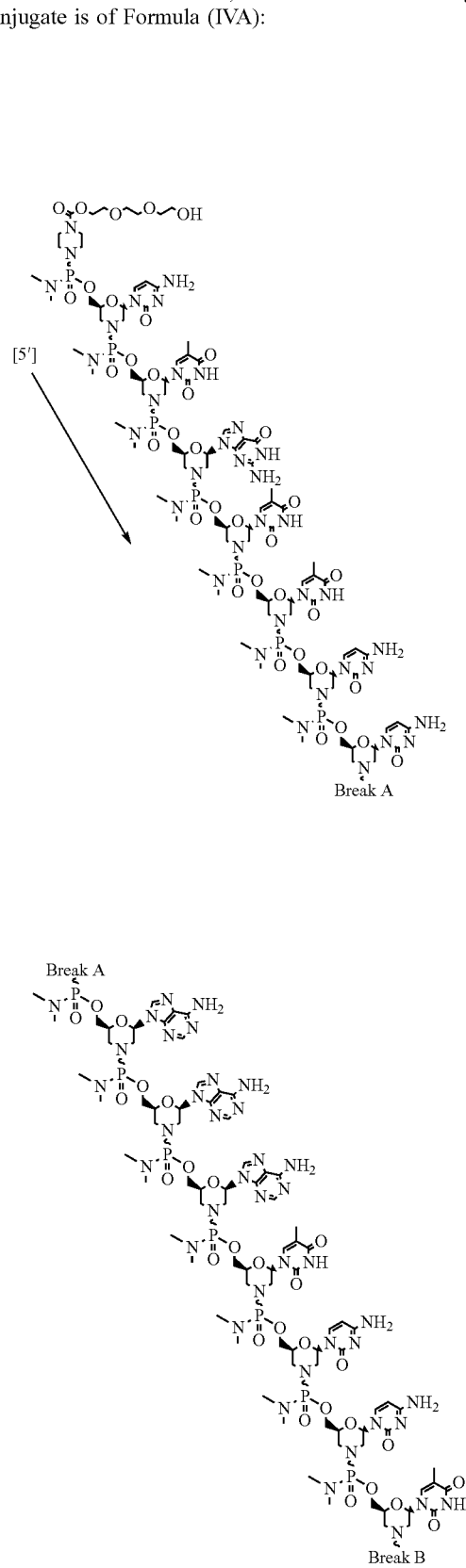

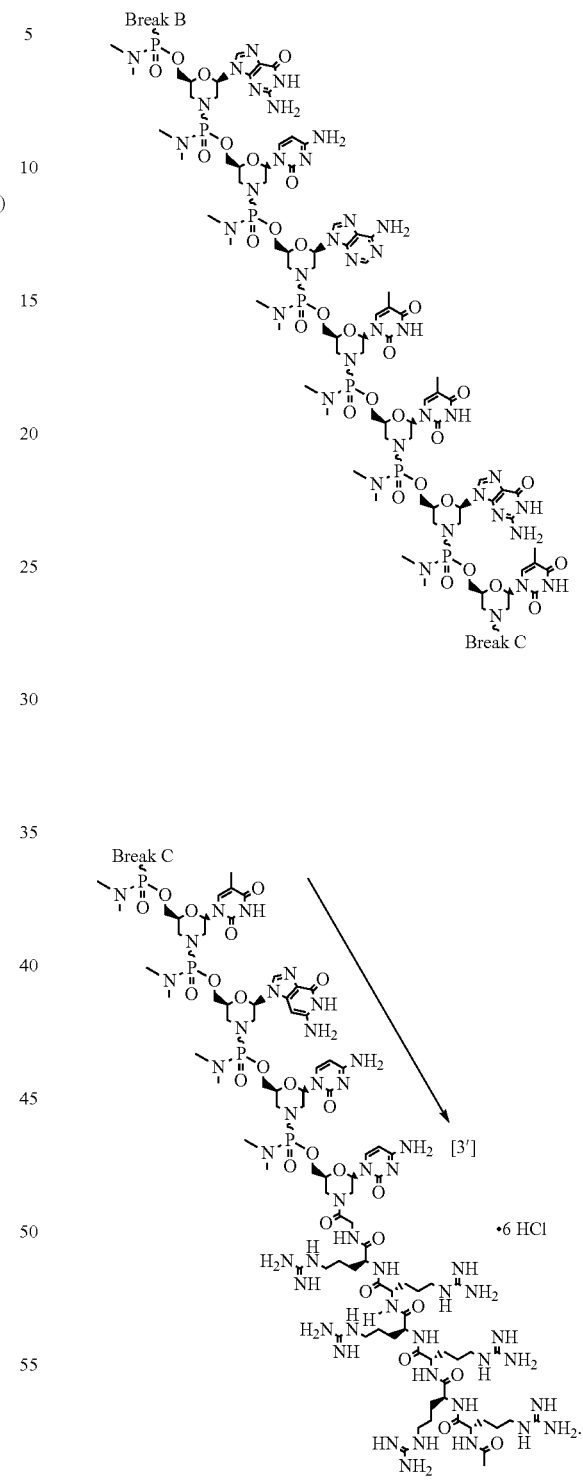

9. A method of excluding exon 52 from dystrophin pre-mRNA during mRNA processing in a subject having a mutation of the dystrophin gene that is amenable to exon 52 skipping, the method comprising administering to the subject a pharmaceutical composition comprising an antisense oligomer conjugate of Formula (IV):

(IV)
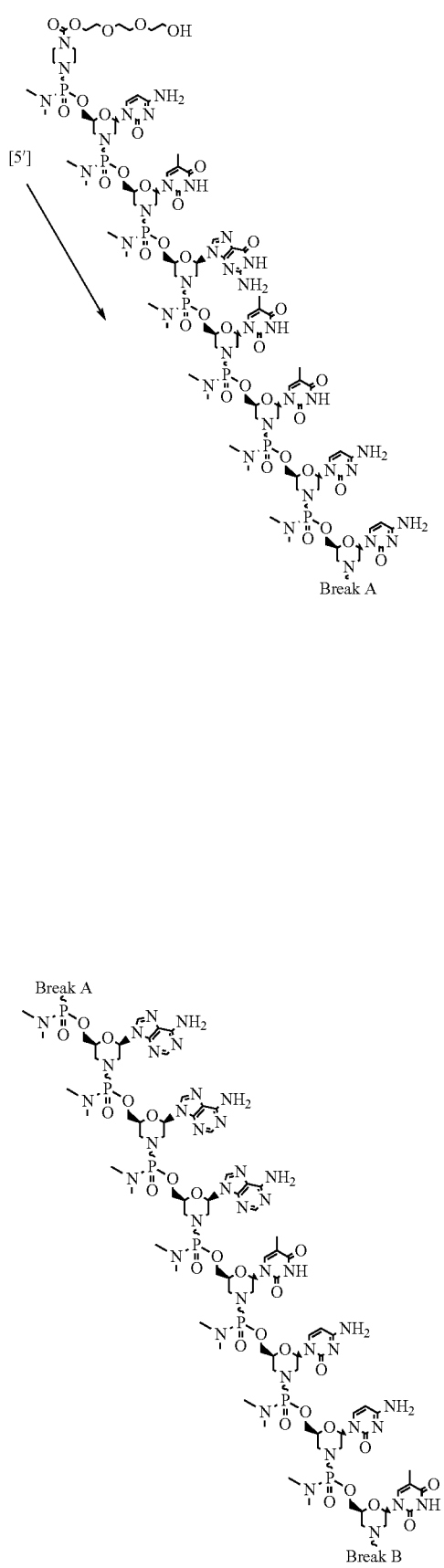
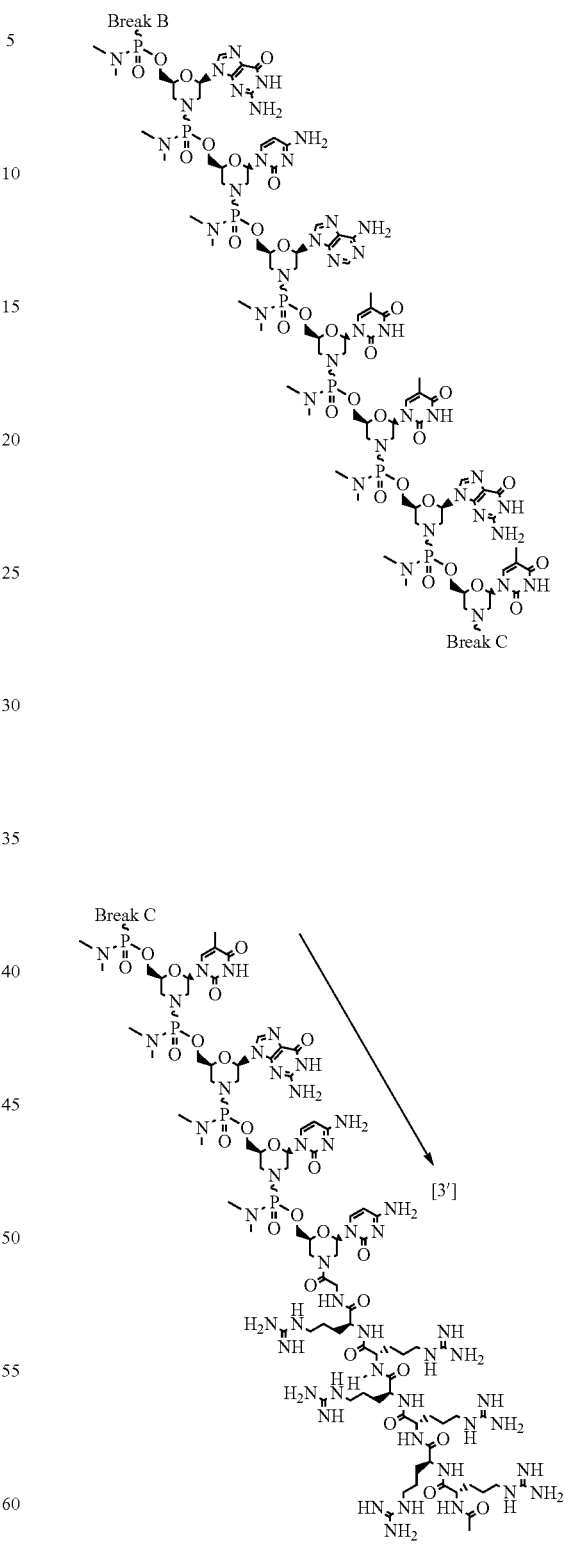
or a pharmaceutically acceptable salt thereof, and a pharmaceutically acceptable carrier.
10. The method of claim 9, wherein the antisense oligomer conjugate is of Formula (IVA):

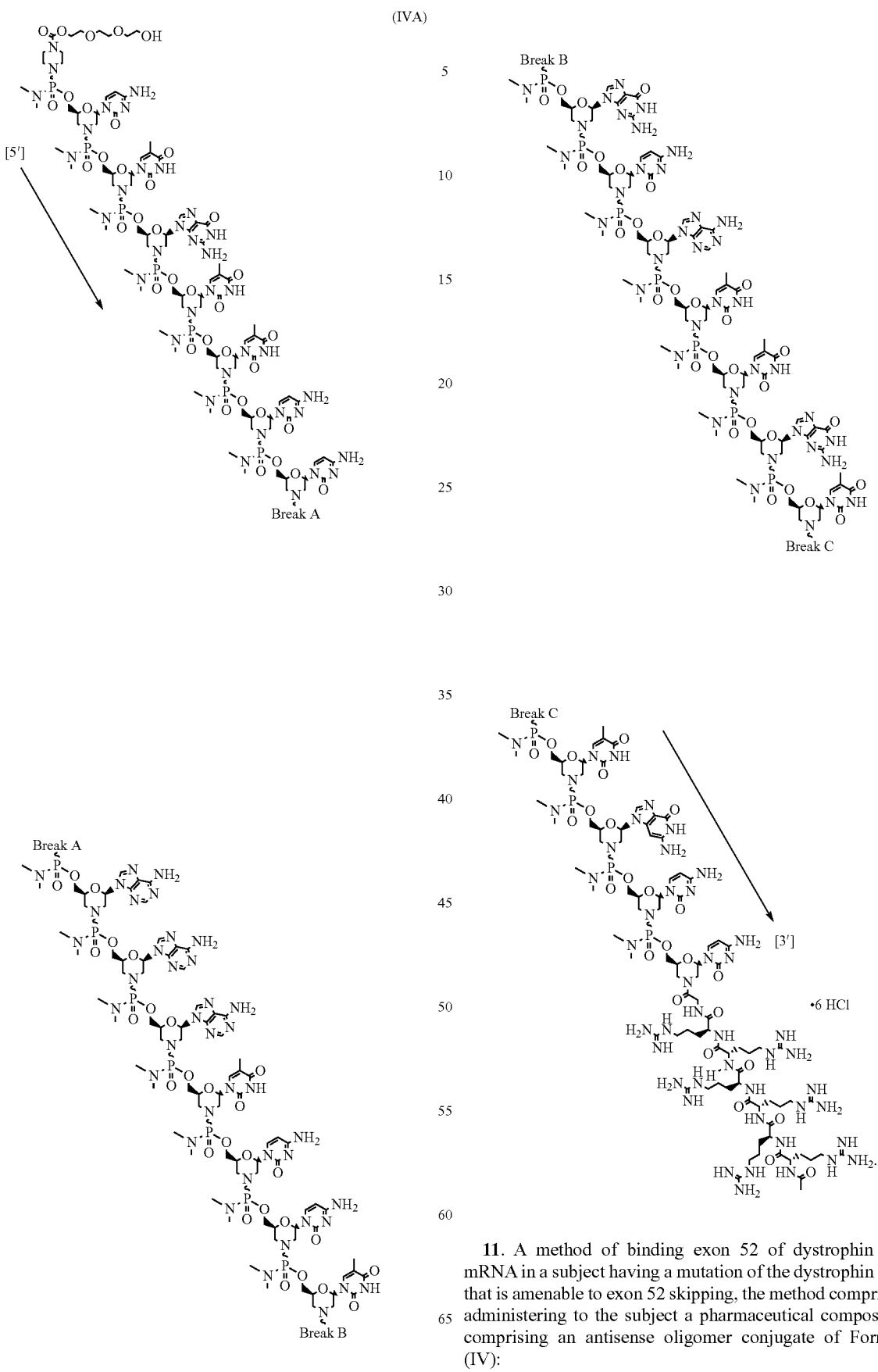
11. A method of binding exon 52 of dystrophin pre-mRNA in a subject having a mutation of the dystrophin gene that is amenable to exon 52 skipping, the method comprising administering to the subject a pharmaceutical composition comprising an antisense oligomer conjugate of Formula (IV):

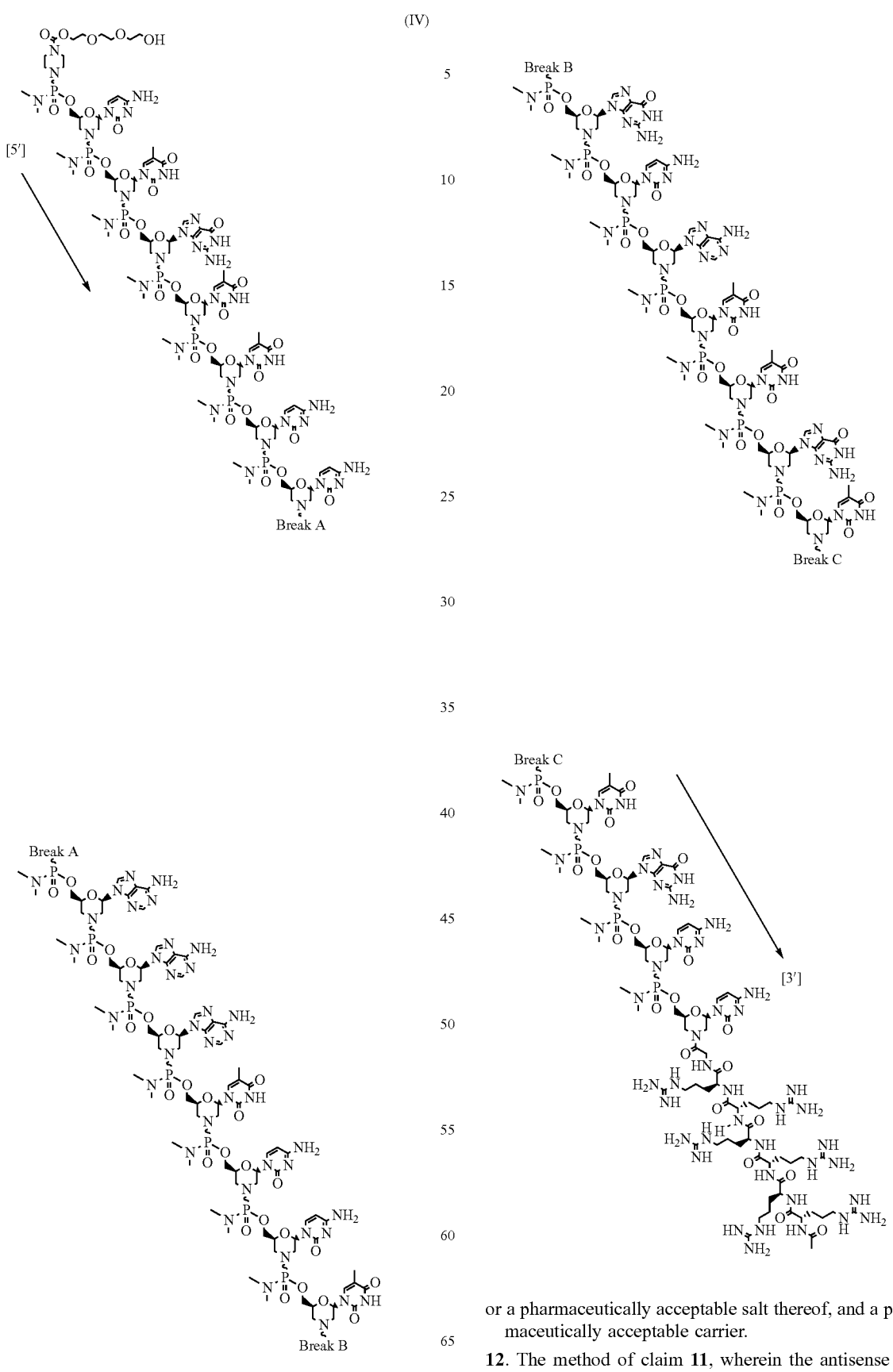
or a pharmaceutically acceptable salt thereof, and a pharmaceutically acceptable carrier.
12. The method of claim 11, wherein the antisense oligomer conjugate is of Formula (IVA):

(IVA)

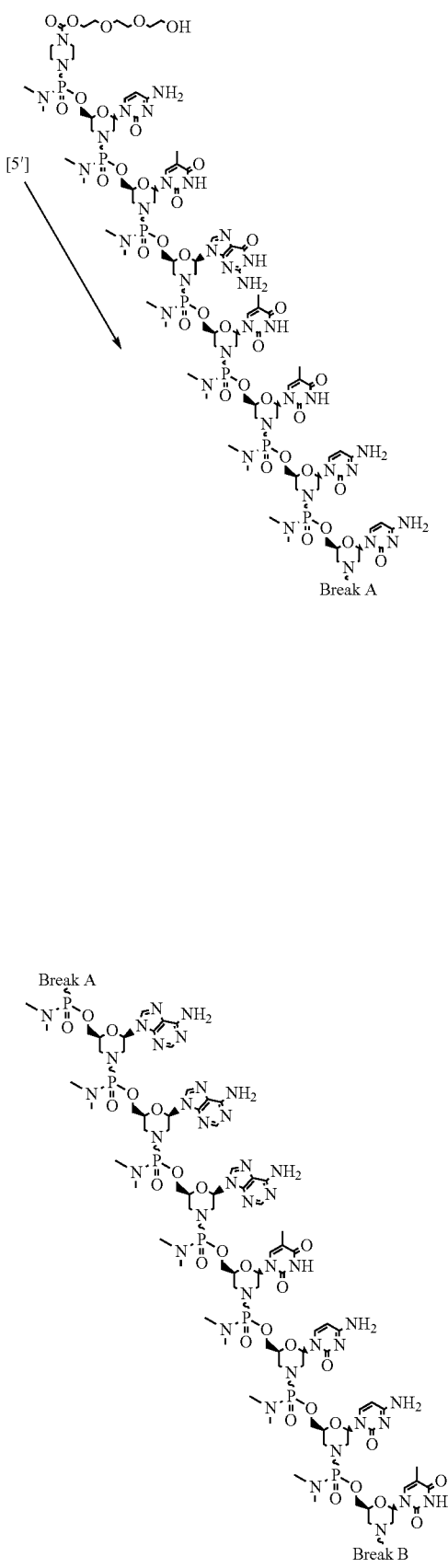

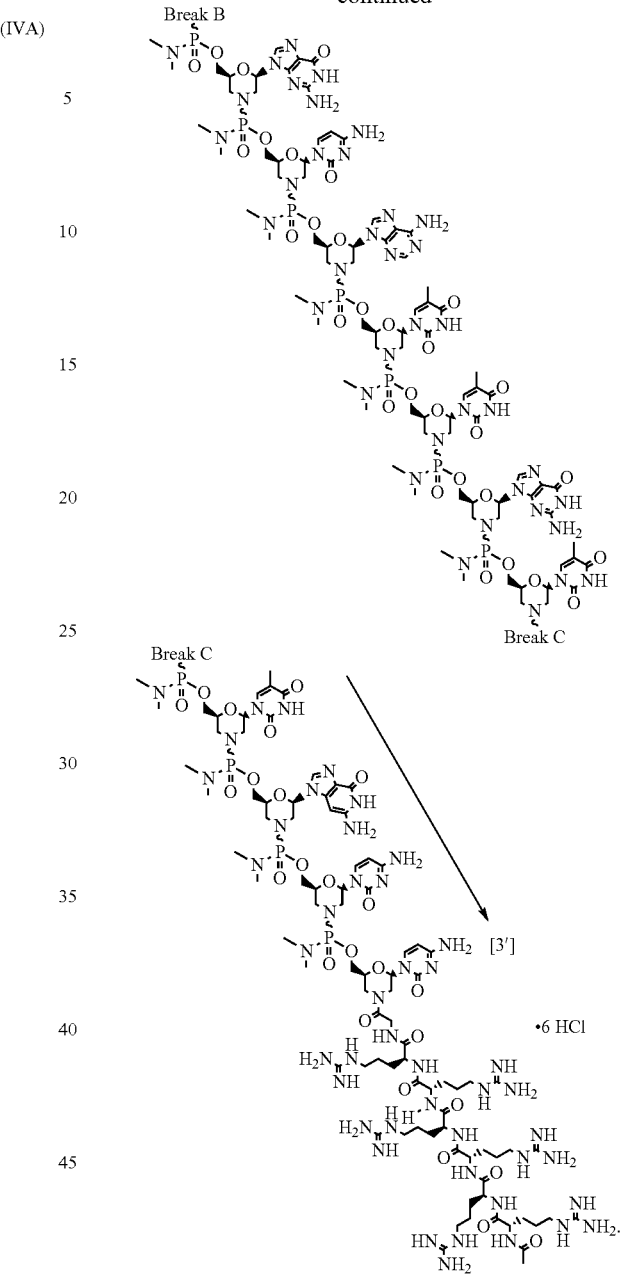

13. The method of claim 1, wherein the antisense oligomer conjugate is administered weekly.

14. The method of claim 1, wherein the antisense oligomer conjugate is administered biweekly.

15. The method of claim 1, wherein the antisense oligomer conjugate is administered every third week.

16. The method of claim 1, wherein the antisense oligomer conjugate is administered monthly.

17. The method of claim 1, wherein the antisense oligomer conjugate is administered at a dose selected from about 30 mg/kg, about 40 mg/kg, about 60 mg/kg, about 80 mg/kg, and about 160 mg/kg.

18. The method of claim 3, wherein the antisense oligomer conjugate is administered weekly.

19. The method of claim 3, wherein the antisense oligomer conjugate is administered biweekly.

20. The method of claim 3, wherein the antisense oligomer conjugate is administered every third week.

21. The method of claim 3, wherein the antisense oligomer conjugate is administered monthly.

22. The method of claim 3, wherein the antisense oligomer conjugate is administered at a dose selected from about 30 mg/kg, about 40 mg/kg, about 60 mg/kg, about 80 mg/kg, and about 160 mg/kg.

* * * * *